(12) United States Patent
Cheney

(10) Patent No.: US 11,066,471 B2
(45) Date of Patent: Jul. 20, 2021

(54) ANTIBODIES TO MICA AND MICB PROTEINS

(71) Applicant: Novelogics Biotechnology Inc., Vancouver (CA)

(72) Inventor: Ian Wayne Cheney, Port Coquitlam (CA)

(73) Assignee: Novelogics Biotechnology Inc., Vancouver (CA)

(*) Notice: Subject to any disclaimer, the term of this patent is extended or adjusted under 35 U.S.C. 154(b) by 84 days.

(21) Appl. No.: 16/343,664

(22) PCT Filed: Oct. 19, 2017

(86) PCT No.: PCT/IB2017/001444
§ 371 (c)(1),
(2) Date: Apr. 19, 2019

(87) PCT Pub. No.: WO2018/073648
PCT Pub. Date: Apr. 26, 2018

(65) Prior Publication Data
US 2019/0248901 A1    Aug. 15, 2019

Related U.S. Application Data

(60) Provisional application No. 62/410,282, filed on Oct. 19, 2016.

(51) Int. Cl.
*A61K 39/00* (2006.01)
*A61P 35/00* (2006.01)
*C07K 16/28* (2006.01)

(52) U.S. Cl.
CPC ......... *C07K 16/2833* (2013.01); *A61P 35/00* (2018.01); *A61K 2039/505* (2013.01); *C07K 2317/24* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,563,450 B2 | 7/2009 | Cosman | |
| 7,666,417 B2 | 2/2010 | Spies | |
| 7,771,718 B2 | 8/2010 | Spies | |
| 7,959,916 B2 | 6/2011 | Spies | |
| 8,182,809 B1 | 5/2012 | Wu | |
| 10,851,148 B2 | 12/2020 | Cheney | |
| 2003/0195337 A1 | 10/2003 | Cosman | |
| 2005/0233391 A1 | 10/2005 | Spies | |
| 2009/0274699 A1 | 11/2009 | Cosman | |
| 2010/0111973 A1 | 5/2010 | Dranoff | |
| 2010/0316650 A1 | 12/2010 | Spies | |
| 2011/0311561 A1 | 10/2011 | Martin | |
| 2011/0311535 A1 | 12/2011 | Dranoff | |
| 2012/0295288 A1 | 11/2012 | Yu | |
| 2014/0004112 A1 | 2/2014 | Wucherpfennig | |
| 2014/0037630 A1 | 2/2014 | Dranoff | |
| 2016/0030659 A1 | 2/2016 | Cheney | |
| 2016/0046689 A1 | 2/2016 | Cheney | |

FOREIGN PATENT DOCUMENTS

| | | |
|---|---|---|
| EP | 01949915 A2 | 7/2008 |
| WO | 1998019167 A2 | 6/1998 |
| WO | 2003089616 A2 | 10/2003 |
| WO | 2006024367 A2 | 3/2006 |
| WO | 2008036981 A1 | 3/2008 |
| WO | 2013049517 A2 | 4/2013 |
| WO | 2013117614 A2 | 8/2013 |
| WO | 2013117647 A1 | 8/2013 |
| WO | 2014140884 A2 | 9/2014 |
| WO | 2014140904 A2 | 9/2014 |
| WO | 2015085210 A1 | 6/2015 |

OTHER PUBLICATIONS

Weiss-Steider et al. J. Experimental Clin. Cancer Res. 30: 1-8, 2011.*
Arreygue-Garcia et al., "Augmented serum level of major histocompatibility complex class I-related chain A (MICA) protein and reduced NKG2D expression on NK and T cells in patients with cervical cancer and precursor lesions," BMC Cancer 8:16 (2008).
Ashiru et al., "Natural Killer Cell Cytotoxicity Is Suppressed by Exposure to the Human NKG2D Ligand MICA*008 That Is Shed by Tumor Cells in Exosomes," Cancer Res 70(2):481-9 (2010).
Bahram et al., "A second lineage of mammalian major histocompatibility complex class I genes," Proc Nat'l Acad Sci USA 91:6259-63 (1994).
Bahram et al., "Nucleotide sequence of the human MHC class I MCA gene," Immunogenetics 44:80-81 (1996).
Bahram et al., "Nucleotide sequence of a human MHC class I MICB cDNA," Immunogenetics 43:230-233 (1996).
Barlow et al., "Continuous and discontinuous antigenic determinants," Nature 322:747-748 (1986).
Bauer et al., "Expression and purification, crystallization and crystallographic characterization of the human MHC class 1 related protein MICA," Acta Cryst D54:451-453 (1998).
Bauer et al., "Activation of NK Cells and T Cells by NKG2D, a Receptor for Stress-Inducible MICA," Science 285 (5428):727-9 (1999).
Boissel et al., "BCR/ABL Oncogene Directly Controls MHC Class I Chain-Related Molecule A Expression in Chronic Myelogenous Leukemia," J Immunol 176(8):5108-5116 (2006).
Bonnafous et al., "Targeting MICA with therapeutic antibodies for the treatment of cancer," J ImmunoTher Cancer 1 (Suppl 1):P41 (2013).

(Continued)

*Primary Examiner* — Sarvamangala Devi
(74) *Attorney, Agent, or Firm* — Dechert LLP

(57) ABSTRACT

This present disclosure relates to antibodies which bind to soluble forms of MICA and/or MICB protein, compositions comprising the antibodies, and use of the antibodies for diagnostics and in treatment of diseases characterized by elevated level of a MIC protein.

16 Claims, 18 Drawing Sheets

Specification includes a Sequence Listing.

(56) References Cited

OTHER PUBLICATIONS

Bonnafous et al., "Targeting MICA with therapeutic antibodies for the treatment of cancer," Innate Pharma Poster Presentation (2013) (1 page).
Cao et al., "RAET1E2, a Soluble Isoform of the UL16-binding Protein RAET1E Produced by Tumor Cells, Inhibits NKG2D-mediated NK," Cytotoxicity, J Biol Chem 282(26):18922-18928 (2007).
Chai, J-G., "Mechanisms of endogenous MHC class II presentation by tumor cells," Immunotherapy 4(8):777-779 (2012).
Chalupny et al., "Down-regulation of the NKG2D ligand MICA by the human cytomegalovirus glycoprotein UL142," Biochem Biophys Res Commun 346(1):175-81 (2006).
Chang et al., "Secretome-Based Identification of ULBP2 as a Novel Serum Marker for Pancreatic Cancer Detection," PLoS One 6(5):e20029 (2011).
Chen et al., "Soluble TNF-a Receptors Are Constitutively Shed and Downregulates Adhresion Molecule Expression in Malignant Gliomas," J Neuropathol Exp Neurol 56(5):541-550 (1997).
Doubrovina et al., "Evasion from NK Cell Immunity by MHC Class I Chain-Related Molecules Expressing Colon Adenocarcinoma," J Immunol 171:6891-6899 (2003).
Champsaur et al., "Effect of NKG2D ligand expression on host immune responses," Immunol Rev 235(1): 267-285 (2010).
Eisele et al., "TGF-☐ and metalloproteinases differentially suppress NKG2D ligand surface expression on malignant glioma cells," Brain 129:2416-2425 (2006).
Fodil et al., "Allelic repertoire of the human MHC class I MICA gene," Immunogenetics 44:351-357 (1996).
Frigoul et al., "MICA: Standardized IMGT allele nomenclature, polymorphisms and diseases," Recent Res Devel Human Genet 3:95-145 (2005).
Gatanaga et al., "Purification and characterization of an inhibitor (soluble necrosis factor receptor) for tumor necrosis factor and lymphotoxin obtained from the serum ultrafiltrates of human cancer patients," Proc Natl Acad Sci USA 87:8781-8784 (1990).
Groh et al., "Broad tumor-associated expression and recognition by tumor-derived T cells of MICA and MICB," Proc Nat'l Acad Sci USA. 96:6879-6884 (1999).
Groh et al., "Fas-ligand-mediated paracrine T cell regulation by the receptor NKG2D in tumor immunity," Nat Immunol 7:755-62 (2006).
Hilpert et al., "Comprehensive Analysis of NKG2D Ligand Expression and Release in Leukemia: Implications for NKG2D-Mediated NK Cell Responses," J Immunol 1360-1371 (2012).
Holdenreider et al, "Soluble MICA in malignant diseases," Int'l J Cancer 118:684-687 (2005).
Holmes et al., "Structural Studies of Allelic Diversity of the MHC Class I Homolog MIC-B, a Stress-Inducible Ligand for the Activating Immunoreceptor NKG2D," J Immunol 169:1395-400 (2002).
Hue et al, "Potential Role of NKG2D/MHC Class I-Related Chain A Interaction in Intrathymic Maturation of Single-Positive CD8 T Cells," J Immunol 171:1909-1917 (2003).
Hue S, et al., "A Direct Role for NKG2D/MICA Interaction in Villous Atrophy during Celiac Disease," Immunity 21:367-377 (2004).
Jimenez-Perez et al., "Cervical cancer cell lines expressing NKG2Dligands are able to down-modulate the NKG2D receptor on NKL cells with functional implications," BMC Immunology 13:7 (2012).
Jinushi et al., "Therapy-induced antibodies to MHC class I chain-related protein A antagonize immune suppression and stimulate antitumor cytotoxicity," Proc Natl Acad Sci USA 103(24):9190-9195 (2006).
Jinushi et al., "MHC class I chain-related protein A antibodies and shedding are associated with the progression of multiple myeloma," Proc Natl Acad Sci USA 105(4): 1285-1290 (2008).
Jonjic et al., "Immune evasion of natural killer cells by viruses," Curr Opin Immunol 20(1):30-8 (2008).

Kaiser et al., "Disulphide-isomerase-enabled shedding of tumour-associated NKG2D ligands," Nature 447 (7143):482-6 (2007).
Kong et al., "The NKG2D ligand ULBP4 binds to TCRγ9/δ2 and induces cytotoxicity to tumor cells through both TCRγδ and NKG2D," Blood 114(2):310-17 (2009).
Kringelum et al., "Reliable B Cell Epitope Predictions: Impacts of Method Development and Improved Benchmarking," PLoS Computational Biol 8(12):e1002829 (2012).
Kumar et al., Soluble MICA and a MICA Variation as Possible Prognostic Biomarkers for HBV-Induced Hepatocellular Carcinoma, , PLoS One 7(9)1-6 e44743 (2012).
Leelayuwat et al., "A new polymorphic and multicopy MHC gene family related to nonmammalian class I," Immunogenetics 40:339-351 (1994).
Li et al., "Crystal Structure of the MHC Class I Homolog MIC-A, a γδ T Cell Ligand," Immunity 10(5):577-84 (1999).
Li et al., "Complex structure of the activating immunoreceptor NKG2D and its MHC class I—like ligand MICA," Nature Immunol 2(5):443-451 (2001).
Li et al., "Clinical significance of the NKG2D ligands, MICA/B and ULBP2 in ovarian cancer: high expression of ULBP2 is an indicator of poor prognosis," Cancer Immunol Immunother 58(5):641-52 (2009).
Liu, et al. "Perturbation of NK cell peripheral homeostasis accelerates prostate carcinoma metastasis," J Clin Invest 123(10):4410-4422 (2013).
Matusali et al., "Soluble ligands for the NKG2D receptor are released during HIV-1 infection and impair NKG2D expression and cytotoxicity of NK cells," FASEB J 27(6):2440-50 (2013).
McFarland et al., "Symmetry Recognizing Asymmetry: Analysis of the Interactions between the C-Type Lectin-like Immunoreceptor NKG2D and MHC Class I-like Ligands," Structure 11:411-422 (2003).
Muller et al., "Structure of the HCMV UL16-MICB Complex Elucidates Select Binding of a Viral Immunoevasin to Diverse NKG2D Ligands," PLoS Pathogens 6(1):e1000723 (2010).
Nolting et al., "MHC class I chain-related protein A shedding in chronic HIV-1 infection is associated with profound NK cell dysfunction," Virology 406:12-20 (2010).
Ohashi et al., "Post-translational Modification of the NKG2D Ligand RAET1G Leads to Cell Surface Expression of a Glycosylphosphatidylinositol-linked Isoform," J Biol Chem 285(22):16408-16415 (2010).
Onda et al., "A novel secreted tumor antigen with a glycosylphosphatidylinositol anchored structure ubiquitously expressed in human cancers," Biochem Biophys Res Commun 285(2):235-43 (2001).
Panter et al., "Dynamics of Major Histocompatibility Complex Class I Association with the Human Peptide-loading Complex," J Biol Chem 287(37):31172-31184 (2012).
Paschen et al., "Differential Clinical Significance of Individual NKG2D Ligands in Melanoma: Soluble ULBP2 as an Indicator of Poor Prognosis Superior to S100B," Clin Cancer Res 15(16):5208-5215 (2009).
Groh et al., 2002 "Tumour-derived soluble MIC ligands impair expression of NKG2D and T-cell activation," Nature 419(6908):734-738.
Raffaghello et al., "Downregulation and/or Release of NKG2D Ligands as Immune Evasion Strategy of Human Neuroblastoma," Neoplasia 6(5):558-568 (2004).
Rebmann et al., "Soluble MICA as an independent prognostic factor for the overall survival and progression-free survival of multiple myeloma patients," Clin Immunol 123(1):114-20 (2007).
Radosavljevic et al., "A cluster of ten novel MHC class I related genes on human chromosome 6q24.2-q25.3," Genomics 79:114-23 (2002).
Robinson et al., "IMGT/HLA and IMGT/MHC: Sequence databases for the study of the major histocompatibility complex," Nucleic Acids Res 31:311-314 (2003).
Salih et al., "Functional expression and release of ligands for the activating immunoreceptor NKG2D in leukemia," Blood 102(4):1389-96 (2003).

(56) References Cited

OTHER PUBLICATIONS

Salih et al., "Cutting Edge: Down-Regulation of MICA on Human Tumors by Proteolytic Shedding," J Immunol 169:4098-102 (2002).
Schneider et al., "The Human Herpesvirus-7 (HHV-7) U21 Immunoevasin Subverts NK-Mediated Cytoxicity through Modulation of MICA and MICB," PLoS Pathogens, 7(11):e1002362 (2011).
Song et al., "Soluble ULBP suppresses natural killer cell activity via down-regulating NKG2D expression," Cell Immunol 239(1):22-30 (2006).
Steinle et al., "Diversification, expression, and γδ T cell recognition of evolutionarily distant members of the MIC family of major histocompatibility complex class I-related molecules," Proc Natl Acad Sci USA 95:12510-12515 (1998).
Steinle et al., "Interactions of human NKG2D with its ligands MICA, MICB, and homologs of the mouse RAE-1protein family," Immunogenetics 53:279-287, (2001).
Sutherland et al., "The UL16-binding proteins, a novel family of MHC class I-related ligands for NKG2D, activate natural killer cell functions," Immunol Rev 181:185-92 (2001).
Testa et al., "MHC Class I-Presented T Cell Epitopes Identified by Immunoproteomics Analysis Are Targets for a Cross Reactive Influenza-Specific T Cell Response," PLoS One 7(11):e48484 (2012).
Thibodeau et al., "Targeting the MHC Class II antigen presentation pathway in cancer immunotherapy," Oncoimmunology 1(6):908-916 (2012).
Waldhauer et al., "Tumor-Associated MICA Is Shed by ADAM Proteases," Cancer Res 68(15): 6368-6376 (2008).
Wang et al., "An Six-Amino Acid Motif in the α3 domain of MICA Is the Cancer Therapeutic Target to Inhibit Shedding," Biochem Biophys Res Commun 387(3): 476-481 (2009).
Welte et al., "Selective intracellular retention of virally induced NKG2D ligands by the human cytomegalovirus UL16 glycoprotein," Eur J Immunol 33:194-203 (2003).
Wu et al., "Prevalent expression of the immunostimulatory MHC class I chain—related molecule is counteracted by shedding in prostate cancer," J Clin Invest 114:560-8 (2004).
Wu et al., "Obstructing Shedding of the Immune Stimulatory MICB Prevents Tumor Formation: Implication for Targeted Cancer Therapy," Clin Cancer Res 15(2): 632-640 (2009).
Zhou et al., "MICA is a Target for Complement-Dependent Cytotoxicity With Mouse Monoclonal Antibodies and Human Alloantibodies," Hum Immunol 63:30-39 (2002).
Zdrenghea et al., "RSV infection modulates IL-15 production and MICA levels in respiratory epithelial cells," Immunogenetics 47:139-41 (1998).
Zwirner et al., "Identification of MICA as a New Polymorphic Alloantigen Recognized by Antibodies in Sera of Organ Transplant Recipients." Hum Immunol 61:917-924 (2000).
Zwirner et al., "Immunobiology of the human MHC class I chain-related gene A (MICA): from transplantation Immunology to tumor immune escape." Eur Respir J 39:712-20 (2012).
International Preliminary Report on Patentability for PCT/IB2014/001157, dated Sep. 15, 2015 (8 pages).
International Search Report by the International Searching Authority for PCT/IB2014/001157 dated Oct. 15, 2014 (7 pages).
Abcam Antibody Catalog No. ab137847 (accessed Mar. 2013) (3 pages).
Abcam Antibody Catalog No. ab61282 (accessed Mar. 2013) (4 pages).
Abcam Antibody Catalog No. ab62540 (accessed Mar. 2013) (4 pages).
Abcam Antibody Catalog No. ab63709 (accessed Mar. 2013) (4 pages).
Abcam Antibody Catalog No. ab93170 (accessed Mar. 2013) (5 pages).
Abcam Antibody Catalog No. EPR6568-ab150355 (accessed Mar. 2013) (4 pages).
BamOMab Antibody Catalog No. BMO2 (accessed Mar. 2013) (1 page).
BioSUSA Antibody Catalog No. bs-0832R (accessed Mar. 2013) (2 pages).
GeneTex Antibody Catalog No. GTX105052 (accessed Mar. 2013) (2 pages).
GeneWayBio Antibody Catalog No. GWB-MP766A (accessed Mar. 2013) (2 pages).
LifeSpan Antibody Catalog No. LS-B9176 (accessed Mar. 2013) (3 pages).
Novus Antibody Catalog No. NBP1-32830 (accessed Mar. 2013) (3 pages).
Sigma Aldrich Antibody Catalog No. SAB1100065 (3 pages).
ThermoFisher Scientific Antibody Catalog No. PA-528181 (2 pages).
Edwards et al., "The remarkable flexibility of the human antibody repertoire; isolation of over one thousand different antibodies to a single protein, BLγS," J Mol Biol 334(1):103-118 (2003).
Lloyd et al., "Modelling the human immune response: performance of a 1011 human antibody repertoire against a broad panel of therapeutically relevant antigens," Protein Eng Des Sel 22(3):159-168 (2009).
Goel et al., "Plasticity within the Antigen-Combining Site May Manifest as Molecular Mimicry in the Humoral Immune Response," J Immunol 172(12):7358-7367 (2004).
Khan and Salunke, "Adjustable Locks and Flexible Keys: Plasticity of Epitope—Paratope Interactions in Germline Antibodies," J Immunol 192(11):5398-5405 (2014).
Poosaria et al., "Computational de novo design of antibodies binding to a peptide with high affinity," Biotechnol Bioeng 114(6):1331-1342 (2017).
Torres and Casadevall, "The immunoglobulin constant region contributes to affinity and specificity," Trend Immunol 29(2):91-97 (2008).
Rudikoff et al., "Single amino acid substitution altering antigen-binding specificity," Proc Natl Acad Sci USA 79 (6):1979-1983 (1982).
Vajdos et al., "Comprehensive functional maps of the antigen-binding site of an anti-ErbB2 antibody obtained with shotgun scanning mutagenesis," J Mol Biol 320(2):415-428 (2002).
Holm et al., "Functional mapping and single chain construction of the anti-cytokeratin 8 monoclonal antibody TS1," Mol Immunol 44(6):1075-1084 (2007).
De Pascalis et al., Grafting of "Abbreviated" Complementarity-Determining Regions Containing Specificity-Determining Residues Essential for Ligand Contact to Engineer a Less Immunogenic 0Humanized Monoclonal Antibody, J Immunol 169:3076-3084 (2002).
Wu et al., "Humanization of a murine monoclonal antibody by simultaneous optimization of framework and CDR residues," J Mol Biol 294(1):151-162 (1999).
Groh et al., "Tumour-derived soluble MIC ligands impair expression of NKG2D and T-cell activation," Nature 419:734-738 (2002).
International Preliminary Report on Patentability for PCT/IB2017/001444, dated Apr. 23, 2019 (7 pages).
International Search Report by the International Searching Authority for PCT/IB2017/001444 dated Mar. 15, 2018 (5 pages).

* cited by examiner

```
  1 MGLGPVFLLL AGIFPFAPPG AAAEPHSLRY NLTVLSWDGS VQSGFLTEVH LDGQPFLRCD
 61 RQKCRAKPQG QWAEDVLGNK TWDRETRDLT GNGKDLRMTL AHIKDQKEGL HSLQEIRVCE
121 IHEDNSTRSS QHFYYDGELF LSQNLETKEW TMPQSSRAQT LAMNVRNFLK EDAMKTKTHY
181 HAMHADCLQE LRRYLKSGVV LRRTVPPMVN VTRSEASEGN ITVTCRASGF YPWNITLSWR
241 QDGVSLSHDT QQWGDVLPDG NGTYQTWVAT RICQGEEQRF TCYMEHSGNH STHPVPSGKV
301 LVLQSHWQTF HVSAVAAAAI FVIIIFYVRC CKKKTSAAEG PELVSLQVLD QHPVGTSDHR
361 DATQLGFQPL MSDLGSTGST EGA   (SEQ ID NO:1)
```

FIG._1A

```
  1 MGLGRVLLFL AVAFPFAPPA AAAEPHSLRY NLMVLSQDES VQSGFLAEGH LDGQPFLRYD
 61 RQKRRAKPQG QWAEDVLGAK TWDTETEDLT ENGQDLRRTL THIKDQKGGL HSLQEIRVCE
121 IHEDSSTRGS RHFYYDGELF LSQNLETQES TVPQSSRAQT LAMNVTNFWK EDAMKTKTHY
181 RAMQADCLQK LQRYLKSGVA IRRTVPPMVN VTCSEVSEGN ITVTCRASSF YPRNITLTWR
241 QDGVSLSHNT QQWGDVLPDG NGTYQTWVAT RIRQGEEQRF TCYMEHSGNH GTHPVPSGKV
301 LVLQSQRTDF PYVSAAMPCF VIIIILCVPC CKKKTSAAEG PELVSLQVLD QHPVGTGDHR
361 DAAQLGFQPL MSATGSTGST EGA   (SEQ ID NO:2)
```

FIG._1B

MICA alpha-3 domain: residues 205-297

205_VPPMVNVTRSEASEGNITVTCRASGFYPWNITLSWRQDGVSLSHDTQQWGDVLPDGNGTYQT
WVATRICQGEEQRFTCYMEHSGNHSTHPVPS_297 (SEQ ID NO:3)

FIG._1C

MICB alpha-3 domain: residues 205-297

205_VPPMVNVTCSEVSEGNITVTCRASSFYPRNITLTWRQDGVSLSHNTQQWGDVLPDGNGTYQT
WVATRIRQGEEQRFTCYMEHSGNHGTHPVPS_297 (SEQ ID NO:4)

FIG._1D

Human MICA cDNA

```
   1 cactgcttga gccgctgaga gggtggcgac gtcggggcca tggggctggg cccggtcttc
  61 ctgcttctgg ctggcatctt ccctttttgca cctccgggag ctgctgctga gccccacagt
 121 cttcgttata acctcacggt gctgtcctgg gatggatctg tgcagtcagg gtttctcact
 181 gaggtacatc tggatggtca gcccttcctg cgctgtgaca ggcagaaatg cagggcaaag
 241 ccccagggac agtgggcaga agatgtcctg ggaaataaga catgggacag agagaccaga
 301 gacttgacag ggaacggaaa ggacctcagg atgacctgg ctcatatcaa ggaccagaaa
 361 gaaggcttgc attccctcca ggagattagg gtctgtgaga tccatgaaga caacagcacc
 421 aggagctccc agcatttcta ctacgatggg gagctcttcc tctcccaaaa cctggagact
 481 aaggaatgga caatgcccca gtcctccaga gctcagacct tggccatgaa cgtcaggaat
 541 ttcttgaagg aagatgccat gaagaccaag acacactatc acgctatgca tgcagactgc
 601 ctgcaggaac tacggcgata tctaaaatcc ggcgtagtcc tgaggagaac agtgcccccc
 661 atggtgaatg tcacccgcag cgaggcctca gagggcaaca ttaccgtgac atgcagggct
 721 tctggcttct atcctggaa tatcacactg agctggcgtc aggatggggt atctttgagc
 781 cacgacaccc agcagtgggg ggatgtcctg cctgatggga atggaaccta ccagacctgg
 841 gtggccacca ggatttgcca aggagaggag cagaggttca cctgctacat ggaacacagc
 901 gggaatcaca gcactcaccc tgtgcctct gggaaagtgc tggtgcttca gagtcattgg
 961 cagacattcc atgtttctgc tgttgctgct gctgctattt ttgttattat tattttctat
1021 gtccgttgtt gtaagaagaa aacatcagct gcagagggtc cagagctcgt gagcctgcag
1081 gtcctggatc aacacccagt tgggacgagt gaccacaggg atgccacaca gctcggattt
1141 cagcctctga tgtcagatct tgggtccact ggctccactg agggcgccta gactctacag
1201 ccaggcagct gggattcaat tccctgcctg gatctcacga gcacttccc tcttggtgcc
1261 tcagtttcct gacctatgaa acagagaaaa taaaagcact tatttatgt tgttggaggc
1321 tgcaaaatgt tagtagatat gaggcgtttg cagctgtacc atatt           (SEQ ID NO:5)
```

*FIG. 2*

Human MICB cDNA

```
   1 gggccatggg gctgggccgg gtcctgctgt ttctggccgt cgccttccct tttgcacccc
  61 cggcagccgc cgctgagccc cacagtcttc gttacaacct catggtgctg tcccaggatg
 121 aatctgtgca gtcagggttt ctcgctgagg gacatctgga tggtcagccc ttcctgcgct
 181 atgacaggca gaaacgcagg gcaaagcccc agggacagtg ggcagaagat gtcctgggag
 241 ctaagacctg ggacacagag accgaggact tgacagagaa tgggcaagac tcaggaggga
 301 ccctgactca tatcaaggac cagaaaggag gcttgcattc cctccaggag attagggtct
 361 gtgagatcca tgaagacagc agcaccaggg gctcccggca tttctactac gatggggagc
 421 tcttcctctc ccaaaacctg gagactcaag aatcgacagt gccccagtcc tccagagctc
 481 agaccttggc tatgaacgtc acaaatttct ggaaggaaga tgccatgaag accaagacac
 541 actatcgcgc tatgcaggca gactgcctgc agaaactaca gcgatatctg aaatccgggg
 601 tggccatcag gagaacagtg ccccccatgg tgaatgtcac ctgcagcgag gtctcagagg
 661 gcaacatcac cgtgacatgc agggcttcca gcttctatcc ccggaatatc acactgacct
 721 ggcgtcagga tggggtatct ttgagccaca acacccagca gtgggggat gtcctgcctg
 781 atgggaatgg aacctaccag acctgggtgg ccaccaggat cgccaagga gaggagcaga
 841 ggttcacctg ctacatggaa cacagcggga atcacggcac tcaccctgtg ccctctggga
 901 aggtgctggt gcttcagagt caacggacag actttccata tgtttctgct gctatgccat
 961 gttttgttat tattattatt ctctgtgtcc cttgttgcaa gaagaaaaca tcagcggcag
1021 agggtccaga gcttgtgagc ctgcaggtcc tggatcaaca cccagttggg acaggagacc
1081 acagggatgc agcacagctg ggatttcagc ctctgatgtc agctactggg tccactggtt
1141 ccactgaggg cgcctagact ctacagccag gcggccagga ttcaactccc tgcctggatc
1201 tcaccagcac tttccctctg tttcctgacc tatgaaacag aaaataacat cacttattta
1261 ttgttgttgg atgctgcaaa gtgttagtag gtatgaggtg tttgctgctc tgccacgtag
1321 agagccagca aagggatcat gaccaactca acattccatt ggaggctata tgatcaaaca
1381 gcaaattgtt tatcatgaat gcaggatgtg ggcaaactca cgactgctcc tgccaacaga
1441 aggtttgctg agggcattca ctccatggtg ctcattggag ttatctactg ggtcatctag
1501 agcctattgt ttgaggaatg cagtcttaca agcctactct ggacccagca gctgactcct
1561 tcttccaccc ctcttcttgc tatctcctat accaataaat acgaagggct gtggaagatc
1621 agagcccttg ttcacgagaa gcaagaagcc cctgaccccc ttgttccaaa tatactcttt
1681 tgtctttctc tttattccca cgttcgccct tgttcagtc caatacaggg ttgtggggcc
1741 cttaacagtg ccatattaat tggtatcatt atttctgttg tttttgtttt tgtttttgtt
1801 tttgttttg agacagagtc tcactcgtca cccaggctgc agttcactgg tgtgatctca
1861 gctcactgca acctctgcct cccaggttca agcacttctc gtacctcaga ctcccgatag
1921 ctgggattac agacaggcac caccacaccc agctaatttt tgtattttt gtagagacgg
1981 ggtttcgcca agttgaccag cccagtttca aactcctgac ctcaggtgat ctgcctgcct
2041 tggcatccca agtgctggg attacaagaa tgagccaccg tgcctggcct attttattat
2101 attgtaatat attttattat attagccacc atgcctgtcc tatttctta tgttttaata
```

FIG._3

```
2161 tattttaata tattacatgt gcagtaatta gattatcatg ggtgaacttt atgagtgagt
2221 atcttggtga tgactcctcc tgaccagccc aggaccagct ttcttgtcac cttgaggtcc
2281 cctcgccccg tcacaccgtt atcgattact ctgtgtctac tattatgtgt gcataattta
2341 taccgtaaat gtttactctt taaataaaaa aaaaaaaaaa (SEQ ID NO:6)
```

```
  1  EPHSLRYNLT VLSWDGSVQS GFLTEVHLDG QPFLRCDRQK CRAKPQGQWA EDVLGNKTWD
 61  RETRDLTGNG KDLRMTLAHI KDQKEGLHSL QEIRVCEIHE DNSTRSSQHF YYDGELFLSQ
121  NLETKEWTMP QSSRAQTLAM NVRNFLKEDA MKTKTHYHAM HADCLQELRR YLKSGVVLRR
181  TVPPMVNVTR SEASEGNITV TCRASGFYPW NITLSWRQDG VSLSHDTQQW GDVLPDGNGT
241  YQTWVATRIC QGEEQRFTCY MEHSGNHSTH PVPS
```
(SEQ ID NO:7)

B.

```
  1  EPHSLRYNLT VLSWDGSVQS GFLTEVHLDG QPFLRCDRQK CRAKPQGQWA EDVLGNKTWD
 61  RETRDLTGNG KDLRMTLAHI KDQKEGLHSL QEIRVCEIHE DNSTRSSQHF YYDGELFLSQ
121  NLETEEWTMP QSSRAQTLAM NVRNFLKEDA MKTKTLYHAM HADCLQELRR YLKSGVVLRR
181  TVPPMVNVTR SEASEGNITV TCRASGFYPW NITLSWRQDG VSLSHDTQQW GDVLPDGNGT
241  YQTWVATRIC QGEEQRFTCY MEHSGNHSTH PVPS
```
(SEQ ID NO:8)

C.

```
  1  EPHSLRYNLT VLSWDGSVQS GFLAEVHLDG QPFLRCDRQK CRAKPQGQWA EDVLGNKTWD
061  RETRDLTGNG KDLRMTLAHI KDQKEGLHSL QEIRVCEIHE DNSTRSSQHF YYDGELFLSQ
121  NLETEEWTMP QSSRAQTLAM NIRNFLKEDA MKTKTHYHAM HADCLQELRR YLKSGVVLRR
161  TVPPMVNVTR SEASEGNITV TCRASGFYPW NITLSWRQDG VSLSHDTQQW GDVLPDGNGT
241  YQTWVATRIC QGEEQRFTCY MEHSGNHSTH PVPS
```
(SEQ ID NO:9)

D.

```
  1  EPHSLPYNLT VLSWDGSVQS GFLAEVHLDG QPFLRYDRQK CRAKPQGQWA EDVLGNKTWD
 61  RETRDLTGNG KDLRMTLAHI KDQKEGLHSL QEIRVCEIHE DNSTRSSQHF YYDGELFLSQ
121  NLETEEWTMP QSSRAQTLAM NVRNFLKEDA MKTKTHYHAM HADCLQELRR YLKSGVVLRR
181  TVPPMVNVTR SEASEGNITV TCRASGFYPW NITLSWRQDG VSLSHDTQQW GDVLPDGNGT
241  YQTWVATRIC QGEEQRFTCY MEHSGNHSTH PVPS
```
(SEQ ID NO:10)

E.

```
  1  EPHSLRYNLT VLSWDGSVQS GFLAEVHLDG QPFLRYDRQK CRAKPQGQWA EDVLGNKTWD
 61  RETRDLTGNG KDLRMTLAHI KDQKEGLHSL QEIRVCEIHE DNSTRSSQHF YYDGELFLSQ
121  NLETEEWTMP QSSRAQTLAM NVRNFLKEDA MKTKTHYHAM HADCLQELRR YLESGVVLRR
181  TVPPMVNVTR SEASEGNITV TCRASSFYPR NITLTWRQDG VSLSHDTQQW GDVLPDGNGT
241  YQTWVATRIC QGEEQRFTCY MEHSGNHSTH PVPS
```
(SEQ ID NO:11)

F.

```
  1  EPHSLRYNLT VLSWDGSVQS GFLTEVHLDG QPFLRCDRQK CRAKPQGQWA EDVLGNKTWD
 61  RETRDLTGNG KDLRMTLAHI KDQKEGLHSL QEIRVCEIHE DNSTRSSQHF YYDGELFLSQ
121  NLETEEWTMP QSSRAQTLAM NVRNFLKEDA MKTKTHYHAM HADCLQELRR YLKSGVVLRR
181  TVPPMVNVTR SEASEGNITV TCRASGFYPW NITLSWRQDG VSLSHDTQQW GDVLPDGNGT
241  YQTWVATRIC QGEEQRFTCY MEHSGNHSTH PVPS
```
(SEQ ID NO:12)

```
  1    EPHSLRYNLT VLSWDGSVQS GFLAEVHLDG QPFLRCDRQK CRAKPQGQWA EDVLGNKTWD
 61    RETRDLTGNG KDLRMTLAHI KDQKEGLHSL QEIRVCEIHE DNSTRSSQHF YYDGELFLSQ
121    NLETEEWTMP QSSRAQTLAM NVRNFLKEDA MKTKTHYHAM HADCLQELRR YLKSGVVLRR
181    TVPPMVNVTR SEASEGNITV TCRASGFYPW NITLSWRQDG VSLSHDTQQW GDVLPDGNGT
241    YQTWVATRIC QGEEQRFTCY MEHSGNHSTH PVPS  (SEQ ID NO:13)
```

H.

```
  1    EPHSLRYNLT VLSWDGSVQS GFLTEVHLDG QPFLRCDRQK CRAKPQGQWA EDVLGNKTWD
 61    RETRDLTGNG KDLRMTLAHI KDQKEGLHSL QEIRVCEIHE DNSTRSSQHF YYDGELFLSQ
121    NLETKEWTMP QSSRAQTLAM NVRNFLKEDA MKTKTHYHAM HADCLQELRR YLKSGVVLRR
181    TVPPMVNVTR SEASEGNITV TCRASGFYPW NITLSWRQDG VSLSHDTQQW GDVLPDGNGT
241    YQTWVATRIC QGEEQRFTCY MEHSGNHSTH PVPSGK  (SEQ ID NO:14)
```

```
  1   EPHSLRYNLM VLSQDESVQS GFLAEGHLDG QPFLRYDRQK RRAKPQGQWA EDVLGAKTWD
 61   TETEDLTENG QDLRRTLTHI KDQKGGLHSL QEIRVCEIHE DSSTRGSRHF YYDGELFLSQ
121   NLETQESTVP QSSRAQTLAM NVTNFWKEDA MKTKTHYRAM QADCLQKLQR YLKSGVAIRR
181   TVPPMVNVTC SEVSEGNITV TCRASSFYPR NITLTWRQDG VSLSHNTQQW GDVLPDGNGT
241   YQTWVATRIR QGEEQRFTCY MEHSGNHGTH PVPS  (SEQ ID NO:15)
```

B.

```
  1   PHSLRYNLMV LSQDGSVQSG FLAEGHLDGQ PFLRYDRQKR RAKPQGQWAE DVLGAKTWDT
 61   ETEDLTENGQ DLRRTLTHIK DQKGGLHSLQ EIRVCEIHED SSTRGSRHFY YDGELFLSQN
121   LETQESTVPQ SSRAQTLAMN VTNFWKEDAM KTKTHYRAMQ ADCLQKLQLP PMVNVICSEV
181   SEGNITVTCR ASSFYPRNIT LTWRQDGVSL SHNTQQWGDV LPDGNGTYQT WVATRIRQGE
241   EQRFTCYMEH SGNHGTHPVP SGKALVLQSQ RTDFP  (SEQ ID NO:16)
```

C.

```
  1   PHSLRYNLMV LSQDGSVQSG FLAEGHLDGQ PFLRYDRQKR RAKPQGQWAE DVLGAETWDT
 61   ETEDLTENGQ DLRRTLTHIK DQKGGLHSLQ EIRVCEMHED SSTRGSRHFY YNGELFLSQN
121   LETQESTVPQ SSRAQTLAMN VTNFWKEDAM KTKTHYRAMQ ADCLQKLQRY LKSGVAIRRT
181   VPPMVNVTCS EVSEGNITVT CRASSFYPRN ITLTWRQDGV SLSHNTQQWG DVLPDGNGTY
241   QTWVATRIRQ GEEQRFTCYM EHSGNHGTHP VPS  (SEQ ID NO:17)
```

D.

```
  1   PHSLRYNLMV LSQDGSVQSG FLAEGHLDGQ PFLRYDRQKR RAKPQGQWAE DVLGAKTWDT
 61   ETEDLTENGQ DLRRTLTHIK DQKGGLHSLQ EIRVCEIHED SSTRGSRHFY YDGELFLSQN
121   LETQESTVPQ SSRAQTLAMN VTNFWKEDAM KTKTHYRAMQ ADCLQKLQRY LKSGVAIRRT
181   VPPMVNVICS EVSEGNITVT CRASSFYPRN ITLTWRQDGV SLSHNTQQWG DVLPDGNGTY
241   QTWVATRIRQ GEEQRFTCYM EHSGNHGTHP VPS  (SEQ ID NO:18)
```

E.

```
  1   PHSLRYNLMV LSQDGSVQSG FLAEGHLDGQ PFLRYDRQKR RAKPQGQWAE NVLGAKTWDT
 61   ETEDLTENGQ DLRRTLTHIK DQKGGLHSLQ EIRVCEIHED SSTRGSRHFY YDGELFLSQN
121   LETQESTVPQ SSRAQTLAMN VTNFWKEDAM KTKTHYRAMQ ADCLQKLQRY LKSGVAIRRT
181   VPPMVNVTCS EVSEGNITVT CRASSFYPRN ITLTWRQDGV SLSHNTQQWG DVLPDGNGTY
241   QTWVATRIRQ GEEQRFTCYM EHSGNHGTHP VPS  (SEQ ID NO:19)
```

```
  1  PHSLRYNLMV LSQDGSVQSG FLAEGHLDGQ PFLRYDRQKR RAKPQGQWAE DVLGAETWDT
 61  ETEDLTENGQ DLRRTLTHIK DQKGGLHSLQ EIRVCEIHED SSTRGSRHFY YNGELFLSQN
121  LETQESTVPQ SSRAQTLAMN VTNFWKEDAM KTKTHYRAMQ ADCLQKLQRY LKSGVAIRRT
181  VPPMVNVTCS EVSEGNITVT CRASSFYPRN ITLTWRQDGV SLSHNTQQWG DVLPDGNGTY
241  QTWVATRIRQ GEEQKFTCYM EHSGNHGTHP VPS
```
(SEQ ID NO:20)

G.

```
  1  PHSLRYNLMV LSQDGSVQSG FLAEGHLDGQ PFLRYDRQKR RAKPQGQWAE DVLGAETWDT
 61  ETEDLTENGQ DLRRTLTHIK DQKGGLHSLQ EIRVCEIHED SSTRGSRHFY YNGELFLSQN
121  LETQESTVPQ SSRAQTLAMN VTNFWKEDAM KTKTHYRAMQ ADCLQKLQRY LKSGVAIRRT
181  VPPMVNVTCS EVSEGNITVT CRASSFYPRN ITLTWRQDGV SLSHNTQQWG DVLPDGNGTY
241  QTWVATRIRQ GEEQRFTCYM EHSGNHGTHP VPS
```
(SEQ ID NO:21)

*FIG._5 (cont'd)*

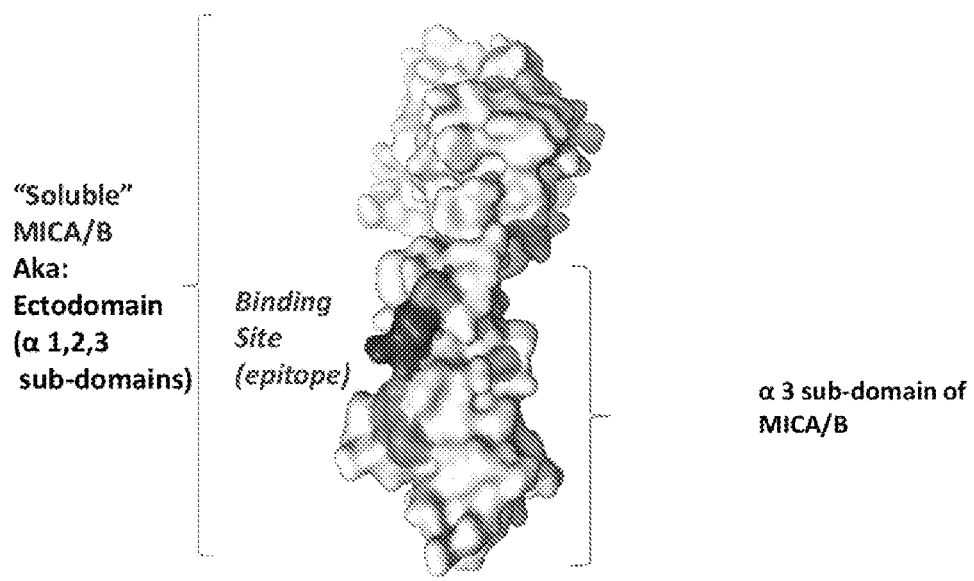
MICA/B α3 Epitope Sequence QQWGDVLP
*FIG._6*

A.

MKLPVRLLVLMFWIPASSSDVL**MTQTPLSLPVSLGDQASISCRSSQSIVHSNGNTYLEWYLQKPGQ
SPKLLIYKVSNRFSGVPDRFSGSGSGTDFTLKISRVEAEDLGVYYCFQGSHVPFTFGSGTKLEIK**R
ADAAPTVS
(SEQ ID NO:24)

B.

```
                        CDR L1                              CDR L2
MTQTPLSLPVSLGDQASISCRSSQSIVHSNGNTYLEWYLQKPGQSPKLLIYKVSNRFSGVPDRFSG

CDR L3
SGSGTDFTLKISRVEAEDLGVYYCFQGSHVPFTFGSGTKLEIK  (SEQ ID NO:25)
```

C.

```
ATGAAGTTGC CTGTTAGGCT GTTGGTGCTG ATGTTCTGGA TTCCTGCTTC CAGCAGTGAT
GTTTTGATGA CCCAAACTCC ACTCTCCCTG CCTGTCAGTC TTGGAGATCA AGCCTCCATC
TCTTGCAGAT CTAGTCAGAG CATTGTACAT AGTAATGGAA ACACCTATTT AGAATGGTAC
CTGCAGAAAC AGGCCAGTC TCCAAAGCTC CTGATCTACA AGTTTCCAA CCGATTTTCT
GGGGTCCCAG ACAGGTTCAG TGGCAGTGGA TCAGGACAG ATTTCACACT CAAGATCAGC
AGAGTGGAGG CTGAGGATCT GGGAGTTTAT TACTGCTTTC AAGGTTCACA TGTTCCATTC
ACGTTCGGCT CGGGGACAAA GTTGGAAATA AAA
```
(SEQ ID NO:26)

D.

```
ATGACCCAAA CTCCACTCTC CCTGCCTGTC AGTCTTGGAG ATCAAGCCTC CATCTCTTGC
AGATCTAGTC AGAGCATTGT ACATAGTAAT GGAAACACCT ATTTAGAATG GTACCTGCAG
AAACCAGGCC AGTCTCCAAA GCTCCTGATC TACAAAGTTT CCAACCGATT TTCTGGGGTC
CCAGACAGGT TCAGTGGCAG TGGATCAGGG ACAGATTTCA CACTCAAGAT CAGCAGAGTG
GAGGCTGAGG ATCTGGGAGT TTATTACTGC TTTCAAGGTT ACATGTTCC ATTCACGTTC
GGCTCGGGGA CAAAGTTGGA AATAAAA
```
(SEQ ID NO:27)

*MEWSGVFIFLLSVTAGVHS*QVQLQQSGAELVRPGTSVKVSCKASGYAFTNYLIEWVKQRPGQGLEW
IGLIYPGSGGTNYNEKFKGKATLTADKSSSTAYMQLSSLTSDDSAVYFCARIYYGNRDYGMDYWGQ
GTSVTVSSAK*TTPPSVYPLAPGCGDTTG*
(SEQ ID NO:28)

F.

```
                              CDR H1                    CDR H2
QVQLQQSGAELVRPGTSVKVSCKASGYAFTNYLIEWVKQRPGQGLEWIGLIYPGSGGTNYNEKFKG

CDR H3
KATLTADKSSSTAYMQLSSLTSDDSAVYFCARIYYGNRDYGMDYWGQGTSVTVSSAK
```
(SEQ ID NO:29)

G.

ATGGAATGGAGCGGAGTCTTTATCTTTCTCCTGTCAGTAACTGCAGGTGTTCACTCCCAG
GTCCAGCTGCAGCAGTCTGGAGCTGAGCTGGTAAGGCCTGGGACTTCAGTGAAGGTGTCC
TGCAAGGCTTCTGGATACGCCTTCACTAATTACTTGATAGAGTGGGTAAAGCAGAGGCCT
GGACAGGGCCTTGAGTGGATTGGACTGATTTATCCTGGAAGTGGTGGTACTAACTACAAT
GAGAAATTCAAGGGCAAGGCAACACTGACTGCAGACAAATCCTCCAGCACTGCCTACATG
CAGCTCAGCAGCCTGACATCTGATGACTCTGCGGTTTATTTCTGTGCAAGAATCTACTAT
GGTAACAGGGACTATGGTATGGACTACTGGGGTCAAGGAACCTCAGTCACCGTCTCCTCA
GCCAAA
(SEQ ID NO:30)

H.

CAGGTCCAGC TGCAGCAGTC TGGAGCTGAG CTGGTAAGGC CTGGGACTTC AGTGAAGGTG
TCCTGCAAGG CTTCTGGATA CGCCTTCACT AATTACTTGA TAGAGTGGGT AAAGCAGAGG
CCTGGACAGG GCCTTGAGTG GATTGGACTG ATTTATCCTG GAAGTGGTGG TACTAACTAC
AATGAGAAAT TCAAGGGCAA GGCAACACTG ACTGCAGACA AATCCTCCAG CACTGCCTAC
ATGCAGCTCA GCAGCCTGAC ATCTGATGAC TCTGCGGTTT ATTTCTGTGC AAGAATCTAC
TATGGTAACA GGGACTATGG TATGGACTAC TGGGGTCAAG GAACCTCAGT CACCGTCTCC
TCAGCCAAA
(SEQ ID NO:31)

*FIG._7 (cont'd)*

QVQLVQSGAEVKKPGASVKVSCKASGYTFT CDR H1 WVRQAPGQGLEWMG CDR H2 RVTITADTSTSTAYMELSSLRSEDTAVYYCAR CDR H3 WGQGTLVTVSS (SEQ ID NO: 32)

QVQLQESGPGLVKPSQTLSLTCTVSGGSVS CDR H1 WIRQPPGKGLEWIG CDR H2 RVTISVDTSKNQFSLKLSSVTAADTAVYYCAR CDR H3 WGQGTLVTVSS (SEQ ID NO: 33)

EVQLVESGGGLVQPGGSLRLSCAASGFTFS CDR H1 WVRQAPGKGLEWVS CDR H2 RFTISRDNSKNTLYLQMNSLRAEDTAVYYCAR CDR H3 WGQGTLVTVSS (SEQ ID NO: 34)

QVQLVQSGSELKKPGASVKVSCKASGYTFT CDR H1 WVRQAPGQGLEWMG CDR H2 RFVFSLDTSVSTAYLQISSLKAEDTAVYYCAR CDR H3 WGQGTSLTVSS (SEQ ID NO: 35)

DIQMTQSPSSLSASVGDRVTITC CDR L1 WYQQKPGKAPKLLIY CDR L2 GVPSRFSGSGSGTDFTLTISSLQPEDFATYYC CDR L3 FGQGTKVEIK (SEQ ID NO: 36)

DIVMTQSPLSLPVTPGEPASISC CDR L1 WYLQKPGQSPQLLIY CDR L2 GVPDRFSGSGSGTDFTLKISRVEAEDVGVYYC CDR L3 FGQGTKVEIK (SEQ ID NO: 37)

EIVLTQSPGTLSLSPGERATLSC CDR L1 WYQQKPGQAPRLLIY CDR L2 GIPDRFSGSGSGTDFTLTISRLEPEDFAVYYC CDR L3 FGQGTKVEIK (SEQ ID NO: 38)

DIVMTQSPDSLAVSLGERATINC CDR L1 WYQQKPGQPPKLLIY CDR L2 GVPDRFSGSGSGTDFTLTISSLQAEDVAVYYC CDR L3 FGQGTKVEI (SEQ ID NO: 39)

FIG._8

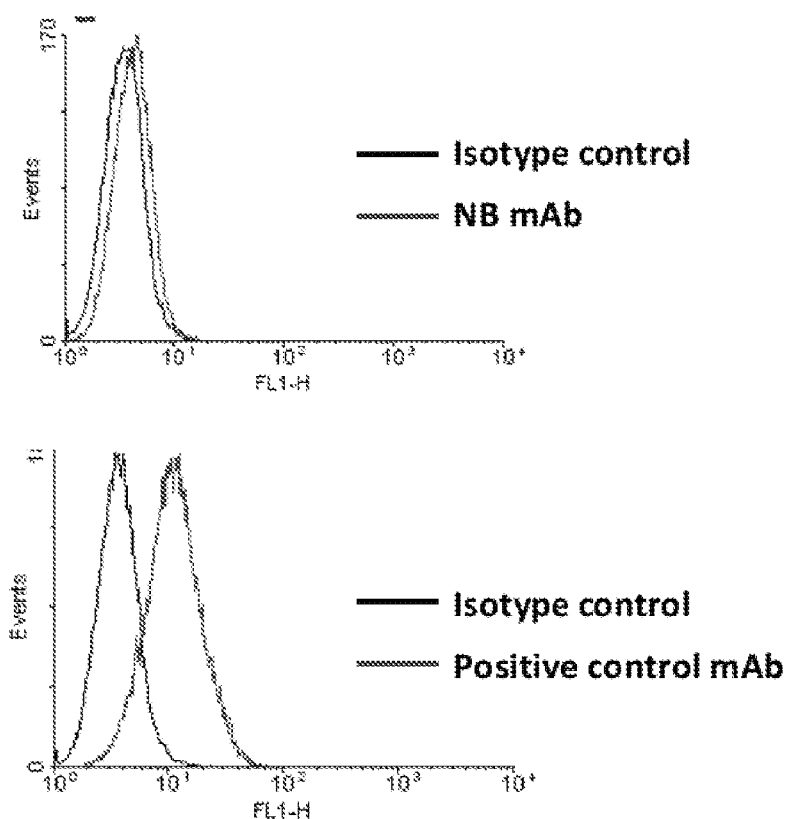
FIG._9
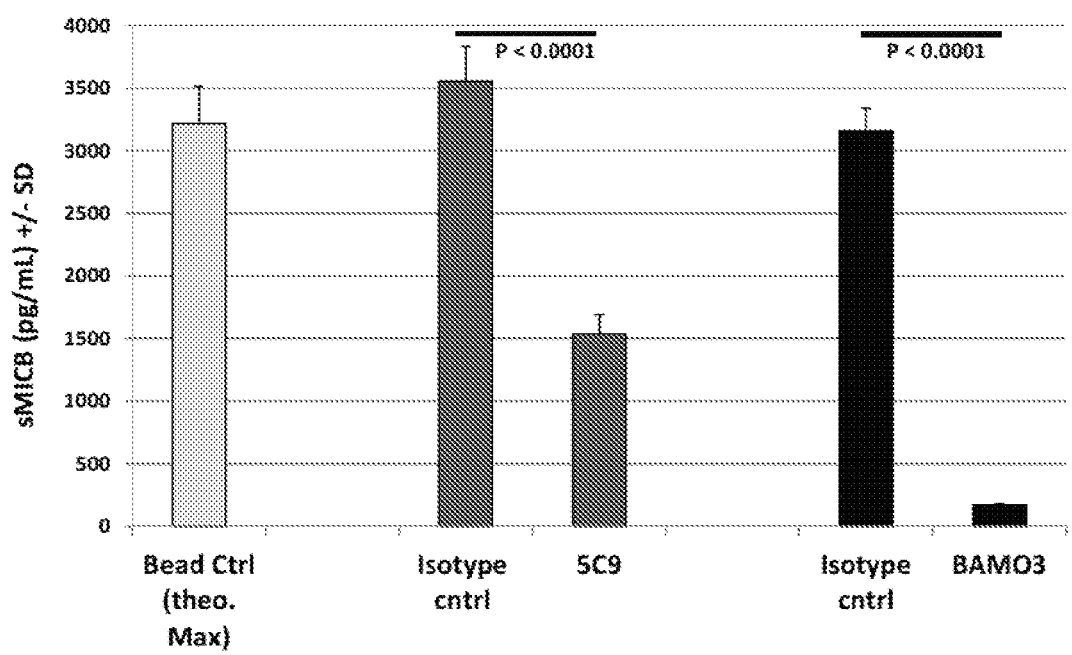
FIG._10

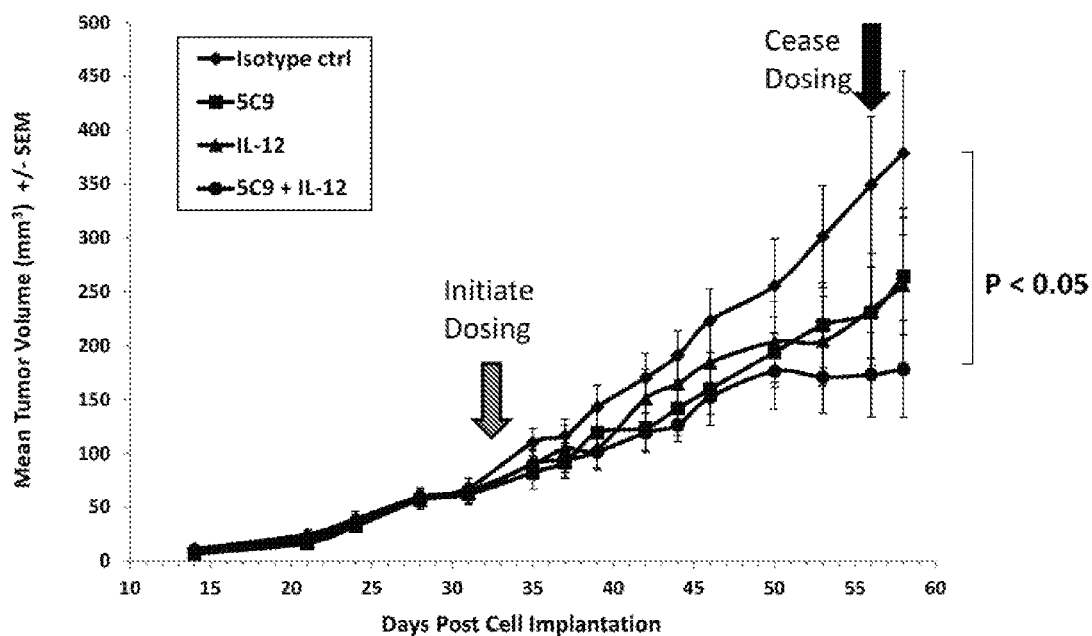
FIG._11
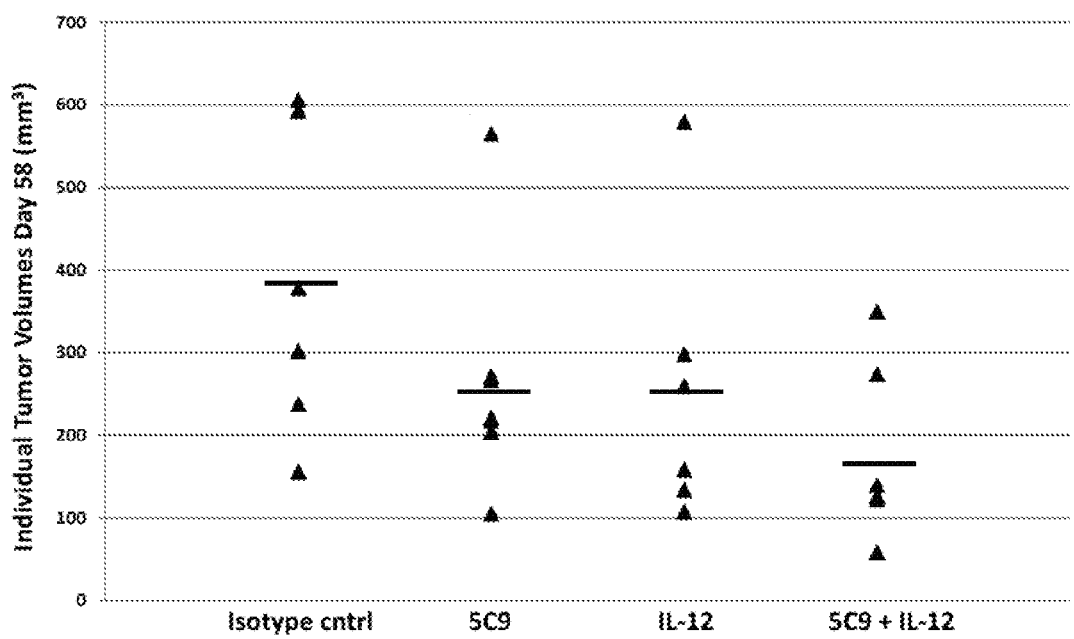
FIG._12

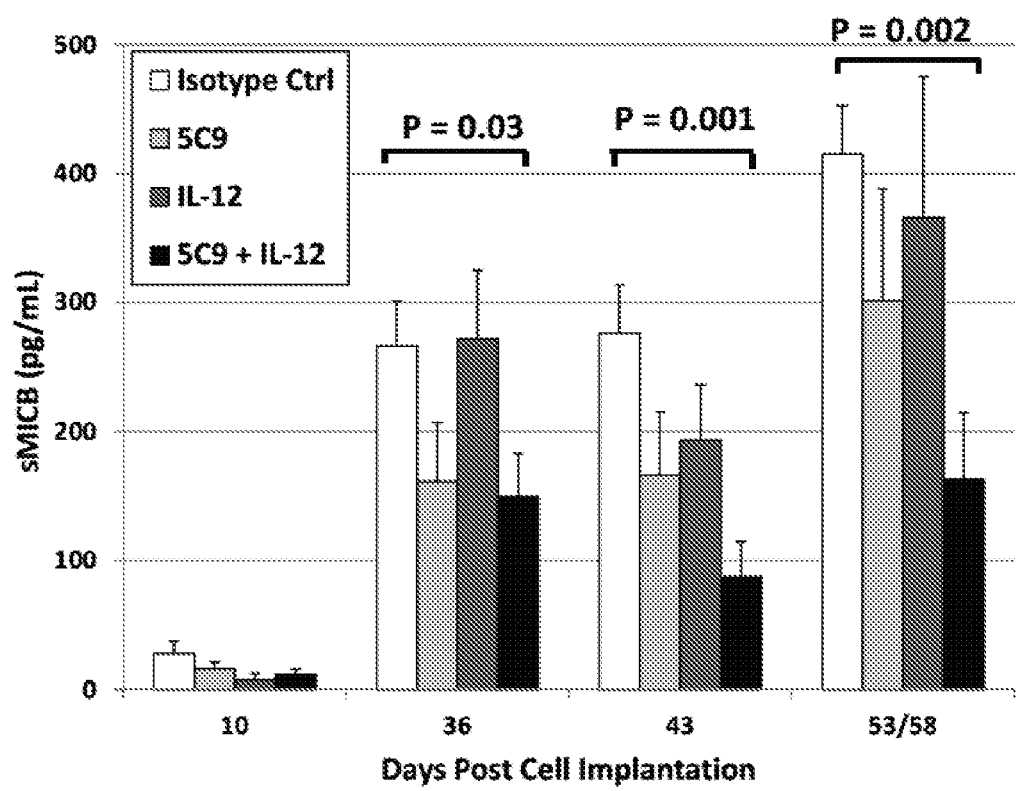
FIG._13

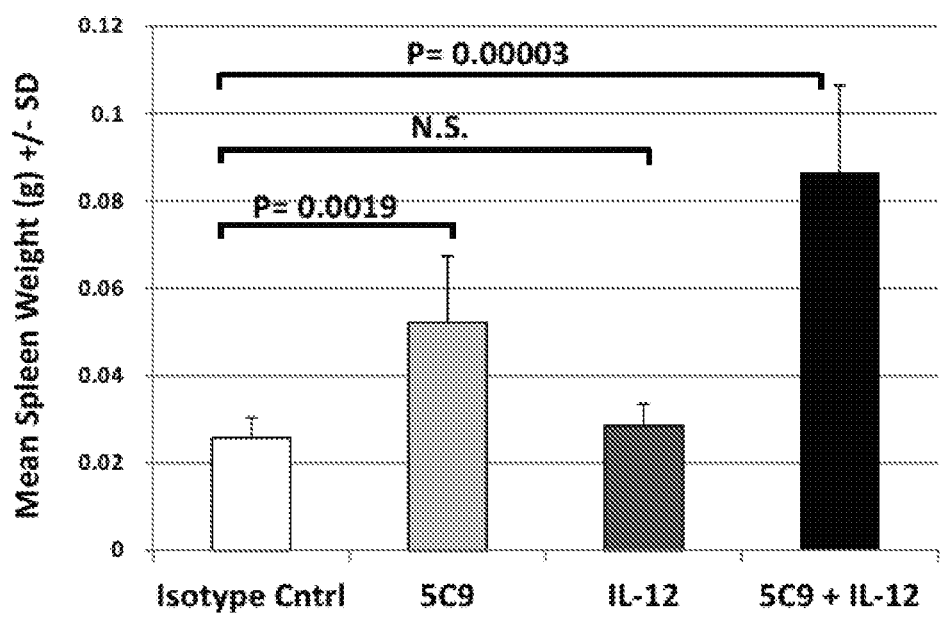
FIG._14

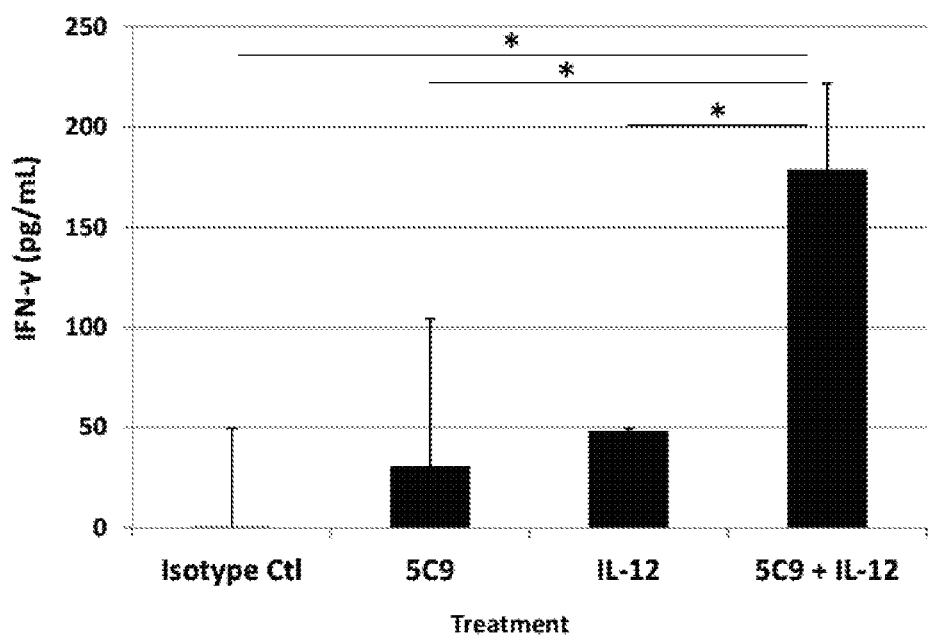
FIG._15

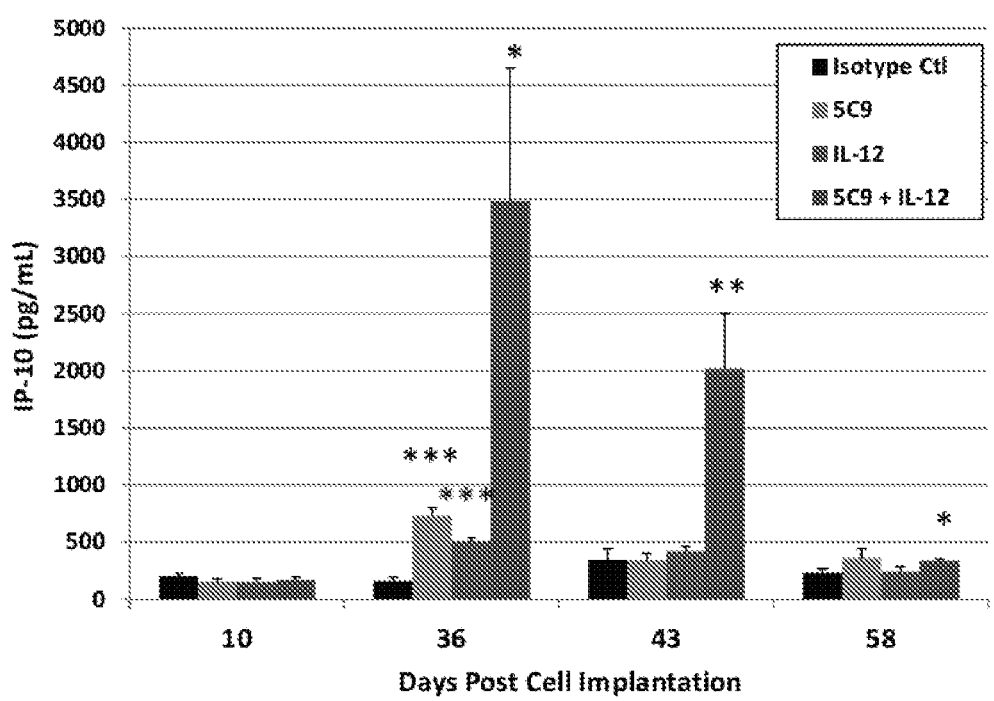
FIG._16

ANTIBODIES TO MICA AND MICB PROTEINS

1. CROSS-REFERENCE TO RELATED APPLICATIONS

This application claims the benefit under 35 U.S.C. § 119(e) of U.S. provisional application No. 62/410,282, filed Oct. 19, 2016, the entire contents of which is incorporated herein by reference.

2. REFERENCE TO SEQUENCE LISTING, TABLE OR COMPUTER PROGRAM

The official copy of the Sequence Listing is submitted concurrently with the specification as an ASCII formatted text file via EFS-Web, with a file name of "NBI-003_ST25.txt", a creation date of Oct. 19, 2017, and a size of 72 kilobytes. The Sequence Listing filed via EFS-Web is part of the specification and is hereby incorporated in its entirety by reference herein.

3. BACKGROUND

Immunotherapy approaches to treatment of cancer attempts to induce, stimulate, and/or derepress the immune response to attack and destroy abnormally proliferating cells. Strategies for immunotherapy have included use of immune activating cytokines, activating antigen presenting cells (e.g., dendritic cells), adoptive cell transfer, targeted antibody dependent cell cytotoxicity (ADCC), immune checkpoint inhibitors, and combinations thereof.

Cytokine-based immunotherapy involves use of cytokines that activate various arms of the immune system to provoke an effective immune response. In this form of immunotherapy, the cytokine is either administered directly into a subject or used ex vivo to activate isolated immune system cells which are then transfused back into the subject (see, e.g., Antony et al, 2010, Curr Med Chem 17(29):3297-302; Ochoa et al., 2013, Curr Gene Ther. 13(1):15-30).

Dendritic cell-based immunotherapy involves harvesting antigen presenting dendritic cells from the subject to be treated and then pulsing the cells with an antigen, tumor lysate, or vector expressing a tumor antigen and then transfusing the treated dendritic cells to a subject to stimulate an immune response against tumor cells expressing the target antigen (see, e.g., Morse et al., 2003, Mol Biotechnol. 25(1):95-9; Palucka et al., 2012, Nature Rev. Cancer 12:265-277).

Adoptive cell therapy is analogous to dendritic cell therapy in that T-cells are obtained from a patient or a donor and then activated, for example with an immune activating cytokine, exposure to cancer antigen, and/or transfection with recombinant genes, and then transfused into a patient. A variant of adoptive T-cell therapy is engineering T-cells to express chimeric antigen receptors (CART). In CART-based therapy, the recombinant chimeric receptor has an antigen binding domain which binds to an antigen on the target cell, and an intracellular domain that can modulate the engineered T cell, such as activation and/or proliferation of T cells directed against the target cancer cells (see, e.g., Grupp et al., 2011, Curr Top Microbiol Immunol. 344:149-72; Lipowska-Bhalla, 2012, Cancer Immunol Immunother. 61(7):953-62).

Immunotherapy can also employ antibody dependent cytotoxicity (ADCC) functions in effector immune cells, such as natural killer (NK) cells, macrophages, neutrophils, and eosinophils, to target proliferating cells. ADCC mediated therapies typically use antibodies directed against an antigen expressed on the target cell surface, where the antibody Fc region binds Fc receptors present on the ADCC immune effector cells. ADCC is generally limited by the antigens expressed by the target cell and the development of therapeutic antibodies against such target antigens.

Another form of immunotherapy involves inhibiting mechanisms that suppress immune cell activation, sometimes referred to as "checkpoint" inhibitors, to restore immune system activity. Exemplary checkpoint inhibitors include antibodies directed against programmed cell death 1 protein, PD-1, and one of its ligands PD-L1. Binding of PD-L1 to PD-1 can lead to inhibition of T-cell activities, and antibodies that block the interaction of PD-L1 and PD-1 can limit this T-cell suppression, allowing the activated T cells to attack cancer cells. Another type of checkpoint inhibitor is an antibody against CTLA-4, a ligand which normally binds its cognate receptor CD80/86 and prevents activating interactions between CD80/86 and CD28. The anti-CTLA antibody disrupts this suppressive interaction of CTLA-4 with CD80/86, thereby allowing activating interactions between CD80/86 and CD28.

While the various immunotherapeutic approaches have been successful in targeting cancer cells, it is not effective in many patients. For example, responses to checkpoint inhibitor therapies, such as anti-PD-1, anti-PD-L1 and anti-CTLA, can be around 20% to 30% of the treated patients, and some cancers do not show clinically meaningful responses to treatment with certain checkpoint inhibitors. Response rates to ADCC based antibody therapy also vary in that a significant percentage of the patients are non-responsive. Higher response rates are observed for CART-based therapy but the studies have largely targeted hematological cancers, and some patients on CART therapy have experienced serious adverse reactions, such as cytokine-release syndrome. In addition, both ADCC and CART-immunotherapies require targeting of an antigen uniquely or preferentially expressed on the target cancer cells, a condition that may limit their application to certain types of cancers.

4. SUMMARY

In one aspect, the present disclosure provides antibodies capable of discriminating between soluble and cell membrane-bound forms of MHC Class I-related chain (MIC) proteins. In various embodiments, the MIC protein is MHC class I chain-related gene A protein (MICA) protein or MHC class I chain-related gene B protein (MICB) protein. The antibodies of the disclosure bind specifically to soluble MIC (sMIC) but do not bind specifically to the extracellular domain of cell membrane-bound MIC. In some embodiments, the epitope bound by the antibodies resides in the alpha-3 domain of MIC protein and is exposed to the antibody when the extracellular domain containing the alpha-3 domain is detached from the transmembrane domain.

In some embodiments, the antibody is capable of binding sMICB produced by human prostate cancer cell line DU-145 with an equilibrium dissociation constant $K_D$ which is at about or lower than the $K_D$ of a reference monoclonal antibody or an equilibrium association constant $K_A$ which is at about or greater than the $K_A$ of a reference monoclonal antibody, where the reference monoclonal antibody is 5C9. In some embodiments, the antibody is capable of attenuating the level of human sMICB in Rag2$^{-/-}$ mice inoculated with xenograft of human prostate cancer cell line DU-145. In some embodiments, the antibody is capable of attenuating growth of xenograft of human prostate cancer cell line DU-145 in Rag2$^{-/-}$ mice.

In some embodiments, the antibody having the characteristics above comprises one or more of the CDRs in the light chain variable region VL comprising the amino acid sequence of SEQ ID NO:25, and/or one or more of the CDRs in the heavy chain variable region VH comprising the amino acid sequence of SEQ ID NO:29.

In some embodiments, the antibody having characteristics above comprises 1, 2, or 3 of the following complementary determining regions (CDR) in the variable light chain: CDR L1 comprising an amino acid sequence RSSQSIVHSNGNTYLE (SEQ ID NO:40); CDR L2 comprising an amino acid sequence KVSNRFS (SEQ ID NO:41); and CDR L3 comprising an amino acid sequence FQGSHVPFT (SEQ ID NO:42). In some embodiments, the antibody having characteristics above comprises 1, 2, or 3 of the following complementary determining regions (CDR) in the variable heavy chain: CDR H1 comprising an amino acid sequence NYLIE (SEQ ID NO:43); CDR H2 comprising an amino acid sequence LIYPGSGGTNYNEKFKG (SEQ ID NO:44); and CDR H3 comprising an amino acid sequence IYYGNRDYGMDY (SEQ ID NO:45).

In some embodiments, the antibody having characteristics above comprises 1, 2, 3, 4, 5 or all 6 of the following complementary determining regions (CDR): CDR L1 comprising an amino acid sequence RSSQSIVHSNGNTYLE (SEQ ID NO:40); CDR L2 comprising an amino acid sequence KVSNRFS (SEQ ID NO:41); CDR L3 comprising an amino acid sequence FQGSHVPFT (SEQ ID NO:42); CDR H1 comprising an amino acid sequence NYLIE (SEQ ID NO:43); CDR H2 comprising an amino acid sequence LIYPGSGGTNYNEKFKG (SEQ ID NO:44); and CDR H3 comprising an amino acid sequence IYYGNRDYGMDY (SEQ ID NO:45).

In some embodiments, the antibody having the characteristics above has a light chain variable region VL comprising an amino acid sequence of SEQ ID NO:24, more particularly SEQ ID NO:25, and a heavy chain variable region VH comprising an amino acid sequence of SEQ ID NO:28, more particularly SEQ ID NO:29.

In another aspect, the antibodies can be applied to various uses, for example in diagnostics and therapeutic treatments. In some embodiments, the antibodies can be used in diagnostic assays to determine the presence of sMIC, e.g., sMICA and/or sMICB, in biological samples, particularly samples obtained from subjects suspected of or diagnosed with a disease or disorder characterized by elevated levels of sMIC, such as certain cancers and viral infections. In some embodiments, the antibodies can be used to determine the level of sMICA and/or sMICB for assessing the prognosis of a subject afflicted with cancer or for assessing the effectiveness of cancer treatment in the subject.

In some embodiments, the antibodies can be used in a method to reduce the levels of sMIC, e.g., sMICA and/or sMICB, in a subject by administering to a subject in need thereof an effective amount of the antibody described herein. In some embodiments, the antibody can be used to treat a subject afflicted with a disease or disorder characterized by elevated levels of a MIC protein. In some embodiments, the disease or disorder is a MIC$^+$ tumor or cancer. In some embodiments, the MIC$^+$ tumor or cancer is characterized by an elevated level of sMIC protein, such as sMICA and/or sMICB.

In some embodiments, the MIC$^+$ tumor or cancer to be treated includes, among others, tumors or cancers of the lung, breast, stomach, colon, pancreas, ovary, kidney, prostate, liver, or skin (e.g., melanoma). In some embodiments, the MIC$^+$ tumor or cancer to be treated is a hematologic malignancy, which includes, among others, Acute Lymphoblastic Leukemia (ALL), Acute Myelogenous Leukemia (AML), Chronic Lymphocytic Leukemia (CLL), Chronic Myelogenous Leukemia (CML), Acute Monocytic Leukemia (AMol); lymphomas such as Hodgkin's lymphoma, and Non-Hodgkin's lymphoma; and Multiple Myeloma.

In some embodiments, the antibodies are administered to treat a subject with a viral infection characterized by elevated expression of a MIC protein. Exemplary viral infections include Respiratory Syncytial Virus (RSV), human Rhinovirus (HRV) and human Immunodeficiency Virus 1 (HIV-1) infections.

In some embodiments, the therapeutic application can be used in combination with other therapeutic agents used to treat the particular disorder associated with elevated levels of MIC, including combinations with chemotherapeutic agents, biologic agents, and cancer vaccines, as further described in the detailed description that follow.

5. BRIEF DESCRIPTION OF THE FIGURES

FIG. 1A and FIG. 1B depict an exemplary amino acid sequence corresponding to a complete human MICA polypeptide (Allele *001: NCBI accession number NP_000238.1) (SEQ ID NO:1), and an exemplary amino acid sequence corresponding to a complete human MICB polypeptide (Allele *001: UniProtKB accession number Q29980.1) (SEQ ID NO:2), respectively.

FIG. 1C and FIG. 1D depict the amino acid sequence of the extracellular alpha-3 domain of MICA protein of the MICA*001 allele, amino acid residues 205-297 (SEQ ID NO:3); and the amino acid sequence of the extracellular alpha-3 domain of MICB protein of the MICB*001 allele, amino acid residues 205-297 (SEQ ID NO:4), respectively. Amino acid residue numbering is based on the unprocessed MICA and MICB proteins. Amino acid numbering based on the processed, mature MICA*001 and MICB*001 corresponds to amino acid residues 182 to 274 for MICA and amino acid residues 182 to 274 for MICB.

FIG. 2 depicts an exemplary nucleotide sequence corresponding to the human MICA cDNA (Allele *001: NCBI accession no. NM_000247.2) (SEQ ID NO:5). The coding region is underlined.

FIG. 3 depicts an exemplary nucleotide sequence corresponding to human MICB cDNA (Allele *001: GenBank accession no. X91625.1) (SEQ ID NO:6). The coding region is underlined.

FIG. 4 depicts exemplary amino acid sequences of putative soluble MICA polypeptides (A—SEQ ID NO:7; B—SEQ ID NO:8; C—SEQ ID NO:9; D—SEQ ID NO:10; E—SEQ ID NO:11; F—SEQ ID NO:12; G—SEQ ID NO:13; H—SEQ ID NO:14).

FIG. 5 depicts exemplary amino acid sequences of putative soluble MICB polypeptides (A—SEQ ID NO:15; B—SEQ ID NO:16; C—SEQ ID NO:17; D—SEQ ID NO:18; E—SEQ ID NO:19; F—SEQ ID NO:20; G—SEQ ID NO:21).

FIG. 6 depicts the putative structure of a sMICA/B containing alpha-1, alpha-2 and alpha-3 domains and the location of the sequence QQWGDVLP (SEQ ID NO:22) in the alpha-3 domain. Epitope mapping studies indicate that the internal sequence GDVL (SEQ ID NO:23) significantly affects binding of antibody 5C9.

FIG. 7A depicts the amino acid sequence of the variable light chain (bolded, underlined), along with the leader sequence (italics) and a portion of the constant region (shaded, italics) of monoclonal antibody 5C9; FIG. 7B depicts the variable light chain sequence for 5C9 and the corresponding CDR L1, CDR L2 and CDR L3; FIG. 7C and FIG. 7D depicts the nucleic acid sequence encoding the amino acid sequence of FIG. 7A and FIG. 7B, respectively; FIG. 7E depicts the amino acid sequence of the variable heavy chain (bolded, underlined), along with the leader sequence (italics) and a portion of the constant region (shaded, italics) of the heavy chain of monoclonal antibody 5C9; FIG. 7F depicts the variable heavy chain sequence for 5C9 and the corresponding CDR H1, CDR H2 and CDR H3; FIG. 7G and FIG. 7H depict the nucleic acid sequence encoding the amino acid sequence of FIG. 7E and FIG. 7F, respectively.

FIG. 8 depicts exemplary human framework regions for immunoglobulin heavy chain (SEQ ID NOS:32-35) and light chain sequences (SEQ ID NOS:36-39). Locations of corresponding CDR regions are shown in bold-underlining.

FIG. 9 provides FACS analysis results showing that monoclonal antibody 5C9 does not bind to cells expressing MIC protein (top panel) in contrast to a positive control monoclonal antibody (mAb) that binds to the extracellular domain of MIC expressed on the cell surface (bottom panel). Isotype control antibody is an antibody that does not bind to MICA and is in the same Ig class as antibody 5C9.

FIG. 10 provides ELISA-based analysis of binding of monoclonal antibody 5C9 to sMICB produced by prostate cancer cell line DU-145.

FIG. 11 shows effect of treatment with 5C9 antibody alone, mouse IL-12 alone, or a combination of 5C9 antibody and IL-12 on growth of prostate cancer cell line DU-145 xenografted into Rag2$^{-/-}$ (knockout) mice.

FIG. 12 shows comparative data on tumor volume measured at day 58 for the in vivo study with prostate cancer DU-145 xenograft shown in FIG. 11.

FIG. 13 shows measured levels of sMICB in Rag2$^{-/-}$ mice with xenografted prostate cancer DU-145 and treated with 5C9 antibody alone, IL-12 alone, and a combination of 5C9 antibody and IL-12 as shown in FIG. 11. sMICB levels were measured at Study Days 10, 36, 43, and 53-58 post cell transplantation. The P values of 0.03, 0.001 and 0.002 (Student's T-test, 2-tailed) on Study Days 36, 43 and 53-58, respectively, are for the combination treatment group of mAb 5C9 plus IL-12 with respect to the isotype control.

FIG. 14 shows measured volume of spleen in Rag2$^{-/-}$ mice inoculated with prostate cancer DU-145 xenograft and treated with 5C9 antibody alone, IL-12 alone, and a combination of 5C9 antibody and IL-12, as shown in FIG. 11. Spleen size was determined at the end of the in vivo studies described in Example 5.

FIG. 15 shows levels of interferon-γ (IFN-γ) in sera of male Rag2$^{-/-}$ mice inoculated with prostate cancer DU-145 xenograft and treated with 5C9 antibody alone, IL-12 alone, and a combination of 5C9 antibody and IL-12. IFN-γ levels were measured by ELISA on day 36. Mean IFN-g+/−SD are shown. The "*" is P<0.05, calculated using Student's T-test.

FIG. 16 shows levels of Interferon-γ inducible Protein 10 (IP-10) in sera of male Rag2$^{-/-}$ mice inoculated with prostate cancer DU-145 xenograft and treated with 5C9 antibody alone, IL-12 alone, and a combination of 5C9 antibody and IL-12. IP-10 levels were measured by ELISA on days 10, 36, 43 and 58. The designation "*" is P<0.05; "" is P<0.01; and "*" is P<0.001, compared to control, and calculated using Student's T-test.

6. DETAILED DESCRIPTION

The present disclosure provides antibodies which recognize soluble forms of MHC class I chain-related gene A protein (MICA) and/or MHC class I chain-related gene B protein (MICB), use of such antibodies to treat diseases characterized by presence of elevated levels of a MIC protein, and as diagnostic reagents for detecting the presence of soluble MIC proteins.

In the descriptions herein, the singular forms "a", "an", and "the" include plural referents unless the context clearly dictates otherwise. In addition, the use of "or" means "and/or" unless stated otherwise. Similarly, "comprise," "comprises," "comprising," "include," "includes," and "including" are interchangeable and not intended to be limiting. Where descriptions of various embodiments use the term "comprising," those skilled in the art would understand that in some specific instances, an embodiment can be alternatively described using language "consisting essentially of" or "consisting of."

Where a range of values is provided, it is understood that each intervening value, to the tenth of the unit of the lower limit unless the context clearly dictates otherwise, between the upper and lower limit of that range and any other stated or intervening value in that stated range, is encompassed within the embodiments. The upper and lower limits of these smaller ranges may independently be included in the smaller ranges and are also encompassed within the description, subject to any specifically excluded limit in the stated range. Where the stated range includes one or both of the limits, ranges excluding either or both of those included limits are also included as part of the embodiments.

6.1 Definitions

Unless defined otherwise, all technical and scientific terms used herein have the same meaning as commonly understood by one of ordinary skill in the art. Accordingly, the following terms are intended to have the following meanings.

"Antibody" is used in the broadest sense and refers to an immunoglobulin or fragment thereof, and encompasses any such polypeptide comprising an antigen-binding fragment or region of an antibody. The recognized immunoglobulin genes include the kappa, lambda, alpha, gamma, delta, epsilon and mu constant region genes, as well as myriad immunoglobulin variable region genes. Light chains are generally classified as either kappa or lambda. Heavy chains are classified as gamma, mu, alpha, delta, or epsilon, which in turn define the immunoglobulin classes, IgG, IgM, IgA, IgD and IgE, respectively. Immunoglobulin classes may also be further classified into subclasses, including IgG subclasses IgG$_1$, IgG$_2$, IgG$_3$, and IgG$_4$; and IgA subclasses IgA$_1$ and IgA$_2$. The term includes, but is not limited to, polyclonal, monoclonal, monospecific, multispecific (e.g., bispecific antibodies), natural, humanized, human, chimeric, synthetic, recombinant, hybrid, mutated, grafted, antibody fragments (e.g., a portion of a full-length antibody, generally the antigen binding or variable region thereof, e.g., Fab, Fab', F(ab')2, and Fv fragments), and in vitro generated antibodies so long as they exhibit the desired biological activity. The term also includes single chain antibodies, e.g., single chain Fv (sFv or scFv) antibodies, in which a variable heavy and a variable light chain are joined together (directly or through a peptide linker) to form a continuous polypeptide.

"Isolated" refers to a change from a natural state, that is, changed and/or removed from its original environment. For example, a polynucleotide or polypeptide (e.g., an antibody) is isolated when it is separated from material with which it is naturally associated in the natural environment. Thus, an "isolated antibody" is one which has been separated and/or recovered from a component of its natural environment.

"Purified antibody" refers to an antibody preparation in which the antibody is at least 80% or greater, at least 85% or greater, at least 90% or greater, at least 95% or greater by weight as compared to other contaminants (e.g., other proteins) in the preparation, such as by determination using SDS-polyacrylamide gel electrophoresis (PAGE) or capillary electrophoresis- (CE) SDS under reducing or nonreducing conditions.

"Extracellular domain" and "ectodomain" are used interchangeably when used in reference to a membrane bound protein and refer to the portion of the protein that is exposed on the extracellular side of a lipid membrane of a cell. In some embodiments, the extracellular domain of MICA is from amino acid residue at about 24 to about 299 of an unprocessed full length MICA protein, where the amino acid numbering is based on the reference MICA protein of the MICA*001 allele. In some embodiments, the extracellular domain of MICB is from amino acid residue at about 24 to about 299 of an unprocessed full length MICB protein, where the amino acid numbering is based on the reference MICB protein of the MICB*001 allele. It is to be understood that the polypeptide region defining the extracellular domain of MICA and MICB is approximate and, in some embodiments, may extend to about amino acid residue 307. An exemplary unprocessed full length MICA protein of the MICA*001 allele is presented in FIG. 1A (SEQ ID NO:1), and an exemplary unprocessed full length MICB protein of the MICB*001 allele is presented in FIG. 1B (SEQ ID NO:2).

"Binds specifically" in the context of any binding agent, e.g., an antibody, refers to a binding agent that binds specifically to an antigen or epitope, such as with a high affinity, and does not significantly bind other unrelated antigens or epitopes.

"Functional" refers to a form of a molecule which possesses either the native biological activity of the naturally existing molecule of its type, or any specific desired activity, for example as judged by its ability to bind to ligand molecules. Examples of "functional" polypeptides include an antibody binding specifically to an antigen through its antigen-binding region.

"Natural Killer Group 2D", "NKG2D" and "NKG2D receptor" refer to a cell surface molecule that is found on numerous types of immune cells, particularly NK cells, CD8+ T cells (e.g., γδ CD8+ T cells, and ca CD8+ T cells) and some CD4+ T cells. NKG2D is also referred to as killer cell lectin-like receptor, subfamily C, member 4, or as KLRC4. The terms "NKG2D" and "NKG2D receptor" includes variants, isoforms, and species homologs of human NKG2D receptor (see, e.g., the isoforms described in Diefenbach et al., 2002, Nat Immunol. 3(12):1142-9). NKG2D is a type II transmembrane protein with an extracellular C-type (i.e., $Ca^{2+}$-binding) lectin-like domain but lacking the $Ca^{2+}$ binding site. It can form heterodimers with adapter proteins such as DAP10 or DAP12, and recognizes protein ligands that include MICA, MICB, ULBP1, ULBP2, ULBP3, ULBP4, ULBP5, and ULBP6. It is to be understood that any activity attributed herein to NKG2D, e.g., cell activation, recognition by antibodies, etc., can also refer to NKG2D-including complexes such as NKG2D-DAP10 or NKG2D-DAP12 heterodimers. Interaction of a NKG2D-bearing immune effector cell, for example an NK cell, with stressed or diseased cells expressing a NKG2D ligand, such as MICA or MICB, enhances the cellular immune response against the stressed/diseased cell.

"MICA" refers to MHC class I chain-related gene A protein (MICA), including variants, isoforms, and species homologs of human MICA. Unlike HLA class I protein, the MICA protein is not known to associate with β2 microglobulin. MICA expression is generally stress induced, and MICA acts as a ligand for natural killer cell (NK) receptor NKG2D. MICA protein comprises three extracellular Ig-like domains, i.e., alpha-1, alpha-2 and alpha-3, a transmembrane domain, and an intracellular domain. The protein is expressed in cells of the gastric epithelium, endothelial cells, fibroblasts, keratinocytes and monocytes. Exemplary sequences of MICA are available as NCBI accession nos. NP_000238.1 (allele MICA*001), presented in FIG. 1A (SEQ ID NO:1) of the present disclosure, and NP_001170990.1 (allele MICA*008.01). Other exemplary MICA sequences can be found in U.S. patent publication 20110311561, incorporated herein by reference.

"MICB" refers to MHC class I chain-related gene B protein (MICB), including variants, isoforms, and species homologs of human MICB. Unlike HLA class I protein, the MICB protein is not known to associate with β2 microglobulin. MICB expression is generally stress induced, and MICB acts as a ligand for natural killer cell (NK) receptor NKG2D. MICB has about 84% sequence identity at the amino acid level to MICA. MICB protein comprises three extracellular Ig-like domains, i.e., alpha-1, alpha-2 and alpha-3, a transmembrane domain, and an intracellular domain. The protein is expressed in the gastric epithelium, endothelial cells, fibroblasts, keratinocytes and monocytes. An exemplary sequence of MICB is available as UniProtKB accession number Q29980.1, which is presented in FIG. 1B (SEQ ID NO:2) of the present disclosure. Other exemplary MICB sequences can be found in U.S. patent publication 20110311561, incorporated herein by reference.

"Soluble MICA" or "sMICA" refers to a MICA protein containing the alpha-1, alpha-2, and alpha-3 domains but which is not attached or tethered to a cell and thus exists extracellularly. Generally, soluble MICA lacks the transmembrane domain. In some embodiments, the sMICA is functional in binding to the NKG2D receptor. As used herein, sMICA encompasses forms released from cells by proteolysis, which forms can be variable because of non-specificity of the proteolytic process. Exemplary sMICA comprises a polypeptide containing amino acid residues from about 24 to about 297 of the unprocessed full length MICA presented in FIG. 1A (SEQ ID NO:1). Exemplary amino acid sequences of putative soluble MICA proteins are also presented in FIG. 4 (SEQ ID NOs:7-14).

"Soluble MICB" or "sMICB" refers to a MICB protein containing the alpha-1, alpha-2, and alpha-3 domains of the MICB protein but which is not attached or tethered to a cell and thus exists extracellularly. Generally, soluble MICB lacks the transmembrane domain. As used herein, sMICB encompasses forms released from cells by proteolysis, which forms can be variable because of non-specificity of the proteolytic process. Exemplary sMICB comprises a polypeptide of amino acid residues from about 24 to about 297 of the unprocessed full length MICB presented in FIG. 1B (SEQ ID NO:2). Exemplary amino acid sequences of putative soluble MICA proteins are also presented in FIG. 5 (SEQ ID NOs:15-21).

"Shedding" or "shed" in reference to a NKG2D ligand, such as MICA and MICB, refers to release of a soluble extracellular domain fragment of a NKG2D ligand from the cell surface of a cell that expresses the NKG2D ligand. Such shedding may be caused by proteolytic cleavage of cell surface NKG2D ligand resulting in release of an extracellular domain fragment from the cell surface. In some embodiments, the soluble extracellular domain or fragment thereof may be encoded by an alternate transcript.

"Full length MIC" refers to a MIC protein containing the alpha-1, alpha-2, and alpha-3 domains; the transmembrane domain; and the intracellular domain. "Unprocessed full length MIC protein" refers to a MIC protein that has not been processed following translation while a "full length mature MIC protein" or "full length processed MIC protein" refers to the processed form of the MIC protein, for example a MIC protein having a leader peptide removed. The full length unprocessed and the full length mature processed proteins can vary in length due to the existence of polymorphisms. In some embodiments, the total unprocessed length (containing a leader sequence) can range from about 332 to about 388 amino acids for MICA and, in some embodiments, is about 383 amino acids for MICB. In some embodiments, the unprocessed full length MIC protein can vary from about 332 to about 388 amino acids. A processed MIC protein (with leader sequences removed) can range from about 309 to about 365 amino acids for MICA and about 360 amino acids for MICB. Exemplary unprocessed full length MIC proteins are set forth in FIG. 1A (SEQ ID NO:1) for MICA and FIG. 1B (SEQ ID NO:2) for MICB. Other exemplary full length MICA and MICB sequences can be found in U.S. patent publication 20110311561 and International patent publication WO2013117647, incorporated herein by reference.

"Membrane bound" in the context of a protein or polypeptide refers to the protein or polypeptide containing the extracellular domain or portions thereof attached to at least the transmembrane domain or other membrane attachment domain. A membrane bound form may or may not include the intracellular domain.

"Alpha-1 domain" of a MIC protein (e.g., MICA and MICB) refers to amino terminal proximal Ig-like region (i.e., G-like domain) on the extracellular domain of MICA and MICB proteins (see, e.g., Frigoul and Lefranc, 2005, Recent Res Devel Human Genet. 3:95-145; incorporated herein by reference). An exemplary alpha-1 domain of MICA contains amino acid residues from about 24 to about 108 of unprocessed MICA protein of the MICA*001 allele. An exemplary alpha-1 domain of MICB contains amino acid residues from about 24 to about 108 of unprocessed MICB protein of the MICB*001 allele.

"Alpha-2 domain" of a MIC protein (e.g., MICA and MICB) refers to the second Ig-like region (i.e., G-like domain) on the extracellular domain of MICA and MICB proteins (see, e.g., Frigoul and Lefranc, 2005, Recent Res Devel Human Genet. 3:95-145, incorporated herein by reference). An exemplary alpha-2 domain of MICA contains amino acid residues from about 109 to about 201 of unprocessed MICA protein of the MICA*001 allele. An exemplary alpha-2 domain of MICB protein contains amino acid residues from about 109 to about 201 of unprocessed MICB protein of the MICB*001 allele.

"Alpha-3 domain" of a MIC protein (e.g., MICA and MICB) refers to the transmembrane proximal region, also referred to as the C-like region on the extracellular domain of MICA and MICB proteins (see, e.g., Frigoul and Lefranc, 2005, Recent Res Devel Human Genet. 3:95-145, incorporated herein by reference). In some embodiments, the alpha-3 domain contains the disulfide bond formed between two cysteine residues in the alpha-3 domain. An exemplary alpha-3 domain of MICA contains amino acid residues from about 205 to about 296 or from about 205 to about 297 of unprocessed MICA protein of the MICA*001 allele. An exemplary alpha-3 domain of MICB protein contains amino acid residues from about 205 to about 296 or from about 205 to about 297 of unprocessed MICB protein of the MICB*001 allele.

"Antigen" refers to a substance, such as, without limitation, a particular peptide, protein, nucleic acid, or carbohydrate which can bind to a specific antibody.

"Epitope" or "antigenic determinant" refers to that portion of an antigen capable of being recognized and specifically bound by a particular antibody. When the antigen is a polypeptide, epitopes can be formed from contiguous amino acids and/or noncontiguous amino acids juxtaposed by tertiary folding of a protein. Linear epitope is an epitope formed from contiguous amino acids on the linear sequence of amino acids. A linear epitope may be retained upon protein denaturing. Conformational or structural epitope is an epitope composed of amino acid residues that are not contiguous and thus comprised of separated parts of the linear sequence of amino acids that are brought into proximity to one another by folding of the molecule, such as through secondary, tertiary, and/or quaternary structures. A conformational or structural epitope may be lost upon protein denaturation. In some embodiments, an epitope can comprise at least 3, and more usually, at least 5 or 8-10 amino acids in a unique spatial conformation. Thus, an epitope as used herein encompasses a defined epitope in which an antibody binds only portions of the defined epitope. There are many methods known in the art for mapping and characterizing the location of epitopes on proteins, including solving the crystal structure of an antibody-antigen complex, competition assays, gene fragment expression assays, mutation assays, and synthetic peptide-based assays, as described, for example, in Using Antibodies: A Laboratory Manual, Chapter 11, Harlow and Lane, eds., Cold Spring Harbor Laboratory Press, Cold Spring Harbor, N.Y. (1999).

"Polymorphic" or "polymorphism" refers to the occurrence of two or more forms of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles. A polymorphic region can also be several nucleotides long. A polymorphic protein refers to occurrence of two or more forms of the protein due to polymorphisms in the encoding gene sequence.

"Allele" refers to the specific gene sequence at a locus, which is the position occupied by a segment of a specific sequence of base pairs along a gene sequence of DNA.

"Protein," "polypeptide," or "peptide" denotes a polymer of at least two amino acids covalently linked by an amide bond, regardless of length or post-translational modification (e.g., glycosylation, phosphorylation, lipidation, myristoylation, ubiquitination, etc.). Included within this definition are D- and L-amino acids, and mixtures of D- and L-amino acids. Unless specified otherwise, the amino acid sequences of a protein, polypeptide, or peptide are displayed herein in the conventional N-terminal to C-terminal orientation.

"Polynucleotide" and "nucleic acid" are used interchangeably herein and refer to two or more nucleosides that are covalently linked together. The polynucleotide may be wholly comprised of ribonucleosides (i.e., an RNA), wholly comprised of 2' deoxyribonucleotides (i.e., a DNA) or mixtures of ribo- and 2' deoxyribonucleosides. The nucleosides will typically be linked together by sugar-phosphate linkages (sugar-phosphate backbone), but the polynucleotides may include one or more non-standard linkages. Non-limiting example of such non-standard linkages include phosphoramidates, phosphorothioates, and amides (see, e.g., Eckstein, F., Oligonucleotides and Analogues: A Practical Approach, Oxford University Press (1992)).

"Operably linked" or "operably associated" refers to a situation in which two or more polynucleotide sequences are positioned to permit their ordinary functionality. For example, a promoter is operably linked to a coding sequence if it is capable of controlling the expression of the sequence. Other control sequences, such as enhancers, ribosome binding or entry sites, termination signals, polyadenylation sequences, and signal sequences are also operably linked to permit their proper function in transcription or translation.

"Amino acid position" and "amino acid residue" are used interchangeably to refer to the position of an amino acid in a polypeptide chain. In some embodiments, the amino acid residue can be represented as "XN", where X represents the amino acid and the N represents its position in the polypeptide chain. Where two or more variations, e.g., polymorphisms, occur at the same amino acid position, the variations can be represented with a "/" separating the variations. A substitution of one amino acid residue with another amino acid residue at a specified residue position can be represented by XNY, where X represents the original amino acid, N represents the position in the polypeptide chain, and Y represents the replacement or substitute amino acid. When the terms are used to describe a polypeptide or peptide portion in reference to a larger polypeptide or protein, the first number referenced describes the position where the polypeptide or peptide begins (i.e., amino end) and the second referenced number describes where the polypeptide or peptide ends (i.e., carboxy end). For example, a peptide from amino acid position 190 to 196 of a processed full length MICA refers to a peptide in which its amino end is at position 190 and its carboxy end is at position 196 of the processed full length MICA protein.

"Polyclonal" antibody refers to a composition of different antibody molecules which is capable of binding to or reacting with several different specific antigenic determinants on the same or on different antigens. A polyclonal antibody can also be considered to be a "cocktail of monoclonal antibodies." The polyclonal antibodies may be of any origin, e.g., chimeric, humanized, or fully human.

"Monoclonal antibody" refers to an antibody obtained from a population of substantially homogeneous antibodies, i.e., the individual antibodies comprising the population are identical except for possible naturally occurring mutations that may be present in minor amounts. Each monoclonal antibody is directed against a single determinant on the antigen. In some embodiments, monoclonal antibodies to be used in accordance with the present disclosure can be made by the hybridoma method described by Kohler et al., 1975, Nature 256:495-7, or by recombinant DNA methods. The monoclonal antibodies can also be isolated, e.g., from phage antibody libraries.

"Chimeric antibody" refers to an antibody made up of components from at least two different sources. A chimeric antibody can comprise a portion of an antibody derived from a first species fused to another molecule, e.g., a portion of an antibody derived from a second species. In some embodiments, a chimeric antibody comprises a portion of an antibody derived from a non-human animal, e.g., mouse or rat, fused to a portion of an antibody derived from a human. In some embodiments, a chimeric antibody comprises all or a portion of a variable region of an antibody derived from a non-human animal fused to a constant region of an antibody derived from a human.

"Humanized antibody" refers to an antibody that comprises a donor antibody binding specificity, e.g., the CDR regions of a donor antibody, such as a mouse monoclonal antibody, grafted onto human framework sequences. A "humanized antibody" typically binds to the same epitope as the donor antibody.

"Fully human antibody" or "human antibody" refers to an antibody that comprises human immunoglobulin protein sequences only. A fully human antibody may contain murine carbohydrate chains if produced in a non-human cell, e.g., a mouse, in a mouse cell, or in a hybridoma derived from a mouse cell.

"Antibody fragment" or "antigen-binding moiety" refers to a portion of a full length antibody, generally the antigen binding or variable domain thereof. Examples of antibody fragments include Fab, Fab', F(ab')2, and Fv fragments; diabodies; linear antibodies; single-chain antibodies; and multispecific antibodies formed from antibody fragments that bind two or more different antigens. Several examples of antibody fragments containing increased binding stoichiometries or variable valencies (2, 3 or 4) include triabodies, trivalent antibodies and trimerbodies, tetrabodies, tandAbs®, di-diabodies and $(sc(Fv)2)_2$ molecules, and all can be used as binding agents to bind with high affinity and avidity to soluble antigens (see, e.g., Cuesta et al., 2010, Trends Biotech. 28:355-62).

"Single-chain Fv" or "sFv" antibody fragment comprises the VH and VL domains of an antibody, where these domains are present in a single polypeptide chain. Generally, the Fv polypeptide further comprises a polypeptide linker between the VH and VL domains which enables the sFv to form the desired structure for antigen binding. For a review of sFv, see Pluckthun in The Pharmacology of Monoclonal Antibodies, Vol. 113, pp. 269-315, Rosenberg and Moore, eds., Springer-Verlag, New York (1994).

"Diabodies" refers to small antibody fragments with two antigen-binding sites, which comprise a heavy chain variable domain (VH) connected to a light chain variable domain (VL) in the same polypeptide chain (VH-VL). By using a linker that is short to allow pairing between the two domains on the same chain, the domains are forced to pair with the complementary domains of another chain and create two antigen-binding sites.

"Antigen binding domain" or "antigen binding portion" refers to the region or part of the antigen binding molecule that specifically binds to and complementary to part or all of an antigen. In some embodiments, an antigen binding domain may only bind to a particular part of the antigen (e.g., an epitope), particularly where the antigen is large. An antigen binding domain may comprise one or more antibody variable regions, particularly an antibody light chain variable region (VL) and an antibody heavy chain variable region (VH), and particularly the complementarity determining regions (CDRs) on each of the VH and VL chains.

"Variable region" and "variable domain" are used interchangeably to refer to the polypeptide region that confers the binding and specificity characteristics of each particular antibody. The variable region in the heavy chain of an antibody is referred to as "VH" while the variable region in the light chain of an antibody is referred to as "VL". The major variability in sequence is generally localized in three regions of the variable domain, denoted as "hypervariable regions" or "CDRs" in each of the VL region and VH region, and forms the antigen binding site. The more conserved portions of the variable domains are referred to as the framework region FR.

"Complementarity-determining region" and "CDR" are used interchangeably to refer to noncontiguous antigen binding regions found within the variable region of the heavy and light chain polypeptides of an antibody molecule. In some embodiments, the CDRs are also described as "hypervariable regions". Generally, naturally occurring antibodies comprise six CDRs, three in the VH (referred to as: CDR H1 or H1; CDR H2 or H2; and CDR H3 or H3) and three in the VL (referred to as: CDR L1 or L1; CDR L2 or L2; and CDR L3 or L3). The CDR domains have been delineated using various approaches, and it is to be understood that CDRs defined by the different approaches are to be encompassed herein. The "Kabat" approach for defining CDRs uses sequence variability and is the most commonly used (Kabat et al., 1991, "Sequences of Proteins of Immunological Interest, 5$^{th}$ Ed." NIH 1:688-96). "Chothia" uses the location of structural loops (Chothia and Lesk, 1987, J Mol Biol. 196:901-17). CDRs defined by "AbM" are a compromise between the Kabat and Chothia approach, and can be delineated using Oxford Molecular AbM antibody modeling software (see, Martin et al., 1989, Proc. Natl Acad Sci USA. 86:9268; see also, world wide web www.bioinf-org.uk/abs). The "Contact" CDR delineations are based on analysis of known antibody-antigen crystal structures (see, e.g., MacCallum et al., 1996, J. Mol. Biol. 262, 732-45). The CDRs delineated by these methods typically include overlapping or subsets of amino acid residues when compared to each other. Generally, the residues defining the CDRs using each of the approaches are noted in the following:

| CDR | Kabat | Chothia | AbM | Contact |
|---|---|---|---|---|
| CDR L1 | 24-34 | 24-34 | 24-34 | 30-36 |
| CDR L2 | 50-56 | 50-56 | 50-56 | 46-55 |
| CDR L3 | 89-97 | 89-97 | 89-97 | 89-96 |
| CDR H1 | 31-35B | 26-32B | 26-35 | 30-35B |
| (Kabat Numbering) | | | | |
| CDR H1 | 31-35 | 26-35 | 26-32 | 30-35 |
| (Chothia Numbering) | | | | |
| CDR H2 | 50-65 | 52-56 | 50-58 | 47-58 |
| CDR H3 | 95-102 | 95-102 | 95-102 | 93-101 |

It is to be understood that the exact residue numbers which encompass a particular CDR will vary depending on the sequence and size of the CDR, and those skilled in the art can routinely determine which residues comprise a particular CDR given the amino acid sequence of the variable region of an antibody.

Kabat, supra, also defined a numbering system for variable domain sequences that is applicable to any antibody. One of skill in the art can assign this system of "Kabat numbering" to any variable domain sequence. Accordingly, unless otherwise specified, references to the number of specific amino acid residues in an antibody or antigen binding fragment are according to the Kabat numbering system.

"Framework region" or "FR region" refers to amino acid residues that are part of the variable region but are not part of the CDRs (e.g., using the Kabat, Chothia or AbM definition). The variable region of an antibody generally contains four FR regions: FR1, FR2, FR3 and FR4. Accordingly, the FR regions in a VL region appear in the following sequence: FR$_L$1-CDR L1-FR$_L$2-CDR L2-FR$_L$3-CDR L3-FR$_L$4, while the FR regions in a VH region appear in the following sequence: FR1$_H$-CDR H1-FR$_H$2-CDR H2-FR$_H$3-CDR H3-FR$_H$4.

"Human consensus framework" refers to a framework that represents the most commonly occurring amino acid residues in a selection of human immunoglobulin VL or VH framework sequences. Generally, the selection of human immunoglobulin VL or VH sequences is from a subgroup of variable domain sequences. In some embodiments, the subgroup sequences are a subgroup presented in Kabat et al., supra. In some embodiments, for the VL the subgroup is subgroup kappa described in Kabat et al., supra. In some embodiments, for the VH the subgroup is subgroup III described in Kabat et al., supra.

"Constant region" or "constant domain" refers to a region of an immunoglobulin light chain or heavy chain that is distinct from the variable region. The constant domain of the heavy chain generally comprises at least one of: a CH1 domain, a Hinge (e.g., upper, middle, and/or lower hinge region), a CH2 domain, and a CH3 domain. In some embodiments, the antibody can have additional constant domains CH4 and/or CH5. In some embodiments, an antibody described herein comprises a polypeptide containing a CH1 domain; a polypeptide comprising a CH1 domain, at least a portion of a Hinge domain, and a CH2 domain; a polypeptide comprising a CH1 domain and a CH3 domain; a polypeptide comprising a CH1 domain, at least a portion of a Hinge domain, and a CH3 domain, or a polypeptide comprising a CH1 domain, at least a portion of a Hinge domain, a CH2 domain, and a CH3 domain. In some embodiments, the antibody comprises a polypeptide which includes a CH3 domain. The constant domain of a light chain is referred to a CL, and in some embodiments, can be a kappa or lambda constant region. However, it will be understood by one of ordinary skill in the art that these constant domains (e.g., the heavy chain or light chain) may be modified such that they vary in amino acid sequence from the naturally occurring immunoglobulin molecule.

"Fc region" or "Fc portion" refers to the C terminal region of an immunoglobulin heavy chain. The Fc region can be a native-sequence Fc region or a non-naturally occurring variant Fc region. Generally, the Fc region of an immunoglobulin comprises constant domains CH2 and CH3. Although the boundaries of the Fc region can vary, in some embodiments, the human IgG heavy chain Fc region can be defined to extend from an amino acid residue at position C226 or from P230 to the carboxy terminus thereof. In some embodiments, the "CH2 domain" of a human IgG Fc region, also denoted as "Cγ2", generally extends from about amino acid residue 231 to about amino acid residue 340. In some embodiments, N-linked carbohydrate chains can be interposed between the two CH2 domains of an intact native IgG molecule. In some embodiments, the CH3 domain of a human IgG Fc region comprises residues C-terminal to the CH2 domain, e.g., from about amino acid residue 341 to about amino acid residue 447 of the Fc region. A "functional Fc region" possesses an "effector function" of a native sequence Fc region. Exemplary Fc "effector functions" include, among others, C1q binding; complement dependent cytotoxicity (CDC); Fc receptor binding; antibody dependent cell-mediated cytotoxicity (ADCC); phagocytosis; down regulation of cell-surface receptors (e.g., LT receptor); etc. Such effector functions generally require the Fc region to be combined with a binding domain (e.g., an antibody variable domain) and can be assessed using various assays known in the art.

"Binding affinity" refers to strength of the sum total of noncovalent interactions between a ligand and its binding partner. In some embodiments, binding affinity is the intrinsic affinity reflecting a one-to-one interaction between the ligand and binding partner. The affinity is generally expressed in terms of equilibrium association ($K_A$) or dissociation constant ($K_D$), which are in turn reciprocal ratios of dissociation ($k_{off}$) and association rate constants ($k_{on}$).

"Percent (%) sequence identity" and "percentage sequence homology" are used interchangeably herein to refer to comparisons among polynucleotides or polypeptides, and are determined by comparing two optimally aligned sequences over a comparison window, wherein the portion of the polynucleotide or polypeptide sequence in the comparison window may comprise gaps as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, 1981, Adv Appl Math. 2:482, by the homology alignment algorithm of Needleman and Wunsch, 1970, J Mol Biol. 48:443, by the search for similarity method of Pearson and Lipman, 1988, Proc Natl Acad Sci USA. 85:2444-8, and particularly by computerized implementations of these algorithms (e.g., BLAST, ALIGN, GAP, BESTFIT, FASTA, and TFASTA; see, e.g., Mount, D. W., Bioinformatics: Sequence and Genome Analysis, $2^{nd}$ Ed., Cold Spring Harbor Laboratory Press, Cold Spring Harbor, N.Y. (2013))

Examples of algorithms that are suitable for determining percent sequence identity and sequence similarity are the BLAST and BLAST 2.0, FASTDB, or ALIGN algorithms, which are publically available (e.g., NCBI: National Center for Biotechnology Information). Those skilled in the art can determine appropriate parameters for aligning sequences. For example, the BLASTN program (for nucleotide sequences) can use as defaults a wordlength (W) of 11, an expectation (E) of 10, M=5, N=−4, and a comparison of both strands. Comparison of amino acid sequences using BLASTP can use as defaults a wordlength (W) of 3, an expectation (E) of 10, and the BLOSUM62 scoring matrix (see Henikoff and Henikoff, 1989, Proc Natl Acad Sci USA. 89:10915-9).

"Amino acid substitution" refers to the replacement of one amino acid in a polypeptide with another amino acid. A "conservative amino acid substitution" refers to the interchangeability of residues having similar side chains, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, isoleucine, and methionine; an amino acid with hydroxyl side chain is substituted with another amino acid with a hydroxyl side chain, e.g., serine and threonine; an amino acid having aromatic side chains is substituted with another amino acid having an aromatic side chain, e.g., phenylalanine, tyrosine, tryptophan, and histidine; an amino acid with a basic side chain is substituted with another amino acid with a basic side chain, e.g., lysine, arginine, and histidine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively.

"Amino acid insertion" refers to the incorporation of at least one amino acid into a predetermined amino acid sequence. An insertion can be the insertion of one or two amino acid residues; however, larger insertions of about three to about five, or up to about ten or more amino acid residues are contemplated herein.

"Amino acid deletion" refers to the removal of one or more amino acid residues from a predetermined amino acid sequence. A deletion can be the removal of one or two amino acid residues; however, larger deletions of about three to about five, or up to about ten or more amino acid residues are contemplated herein.

"Identifying" refers to determining the presence or absence of a defined property. The process may include measuring or detecting various properties, including the binding or lack of binding to an epitope.

"Subject" refers to a mammal, including, but not limited to humans, non-human primates, and non-primates, such as goats, horses, and cows. In some embodiments, the terms "subject" and "patient" are used interchangeably herein in reference to a human subject.

"Biological sample" refers to any biological material taken from a patient or subject. Such samples include cell samples, tissue samples and fluid samples. A "fluid sample" includes, among others, a sample of a patient's blood, plasma, serum, urine, cerebrospinal fluid, lymph, synovial fluid, bile, semen, and saliva. A sample can also include a biopsy sample, whole cells, lysates of cells, or tissues.

"Abnormal" or "abnormality" refers to a level or condition which is statistically different from the level or condition observed in organisms not suffering from a disease or disorder and may be characterized as either an excess amount, intensity or duration of signal or a deficient amount, intensity or duration of signal. The abnormality may be realized as an abnormality in cell function, viability or differentiation state. An abnormal interaction level may also be greater or less than the normal level, and may impair the normal performance or function of an organism.

"Elevated" in the context of a disease or disorder refers to above normal levels of a substance or molecule, such as a disease marker or indicator, that has a statistically significant correlation with the occurrence of the disease or disorder. The levels can be compared to appropriate controls, e.g., healthy subjects without the disease, to determine the levels that signal presence of the disease.

"Cancer" and "cancerous" refer to or describe the physiological condition in mammals in which a population of cells is characterized by unregulated cell growth. Examples of cancers include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, gastrointestinal cancer, pancreatic cancer, glioblastoma, cervical cancer, ovarian cancer, liver cancer, bladder cancer, hepatoma, breast cancer, colon cancer, colorectal cancer, endometrial or eso carcinoma, salivary gland carcinoma, kidney cancer, prostate cancer, vulval cancer, thyroid cancer, hepatic carcinoma and various types of head and neck cancers.

"Proliferative disorder" and "proliferative disease" refer to disorders associated with abnormal cell proliferation such as cancer.

"Tumor" and "neoplasm" refer to any mass of tissue that result from excessive cell growth or proliferation, either benign (noncancerous) or malignant (cancerous) including pre-cancerous lesions.

"$MIC^+$ disease or disorder" refers to a disease or disorder displaying elevated levels of one or more MIC proteins (e.g., MICA and/or MICB) or portions thereof, such as sMIC, that is correlated with the occurrence of the disease or disorder.

"$MICA^+$ disease or disorder" refers to a disease or disorder displaying elevated levels of MICA protein or portions thereof, such as sMICA, that is correlated with the occurrence of the disease or disorder.

"$MICB^+$ disease or disorder" refers to a disease or disorder displaying elevated levels of MICB protein or portions thereof, such as sMICB, that is correlated with the occurrence of the disease or disorder.

"$MIC^+$ tumor" or "$MIC^+$ cancer" refers to a tumor, neoplasm, or cancer characterized by elevated levels of a MIC protein or portions thereof, such as sMICA and/or sMICB.

"$MIC^+$ hematologic malignancy" refers to proliferative disorders of cells of the lymphoid or myeloid system characterized by elevated levels of a MIC protein or portions thereof, such as sMICA and/or sMICB. Lymphoid disorders include acute lymphocytic leukemia and chronic lymphoproliferative disorders (e.g., lymphoma, myeloma, and chronic lymphoid leukemia). Lymphomas include Hodgkin's disease and non-Hodgkin's lymphoma, precursor T-cell leukemia/lymphoma, follicular lymphoma, diffuse large B-cell lymphoma, mantle cell lymphoma, MALT lymphoma, Burkitt's lymphoma, B-cell chronic lymphocytic leukemia/lymphoma, peripheral T-cell lymphoma—not-otherwise-specified, and mycosis fungoides. Chronic lymphoid leukemias include T cell chronic lymphoid leukemia and B cell chronic lymphoid leukemia. Myeloid disorders include chronic myeloid disorders and acute myeloid leukemia. Chronic myeloid disorders include chronic myeloproliferative disorders and myelodysplastic syndrome. Chronic myeloproliferative disorders include angiogenic myeloid metaplasia, essential thrombocythemia, chronic myelogenous leukemia, polycythemia vera, and atypical myeloproliferative disorders. Atypical myeloproliferative disorders include atypical CML, chronic neutrophilic leukemia, mast cell disease, and chronic eosinophilic leukemia.

"$MIC^+$ viral infection" refers to a viral infection characterized by elevated levels of a MIC protein or portions thereof, such as sMICA and/or sMICB.

"Treatment" or "treating" refers to a process that is intended to produce a beneficial change in the condition of a mammal, e.g., a human, often referred to as a patient. A beneficial change can, for example, include one or more of restoration of function; reduction of symptoms; reduction of severity; limitation or retardation of progression of a disease, disorder, or condition or prevention; or limitation or retardation of deterioration of a patient's condition, disease or disorder. In the context of a disease or disorder, a "therapy", "treatment", or "treatable" is meant the therapy achieves a desired pharmacologic and/or physiologic effect on the disease or disorder. The effect may be prophylactic in terms of completely or partially preventing the disease/disorder or symptom thereof and/or may be therapeutic in terms of a partial or complete cure for the disease/disorder and/or adverse effect attributable to the disease/disorder. The term includes: (a) preventing the disease from occurring in a subject which may be predisposed to the disease but has not yet been diagnosed as having it; (b) inhibiting the disease, i.e., arresting its development; or (c) relieving the disease, i.e., causing remission or regression of the disease. The therapeutic agent may be administered before, during or after the onset of the disease or disorder. The treatment of an ongoing disease, where the treatment stabilizes or reduces the undesirable clinical symptoms in the patient, is of particular interest. Such treatment is desirably performed prior to complete loss of function in the affected tissues.

"Therapeutically effective dose" or "therapeutically effective amount" refers to that quantity of a compound, including a biologic compound, or pharmaceutical composition that is sufficient to result in a desired activity upon administration to a mammal in need thereof. As used herein, with respect to the pharmaceutical compositions comprising an antibody, the term "therapeutically effective amount/dose" refers to the amount/dose of the antibody or pharmaceutical composition thereof that is sufficient to produce an effective response upon administration to a mammal.

"Pharmaceutically acceptable" refers to compounds or compositions which are generally safe, non-toxic and neither biologically nor otherwise undesirable, and includes a compound or composition that is acceptable for human pharmaceutical and veterinary use. The compound or composition may be approved or approvable by a regulatory agency or listed in the U.S. Pharmacopeia or other generally recognized pharmacopeia for use in animals, including humans.

"Pharmaceutically acceptable excipient, carrier or adjuvant" refers to an excipient, carrier or adjuvant that can be administered to a subject, together with at least one therapeutic agent (e.g., an antibody of the present disclosure), and which does not destroy the pharmacological activity thereof and is generally safe, nontoxic and neither biologically nor otherwise undesirable when administered in doses sufficient to deliver a therapeutic amount of the agent.

"Combination therapy" refers to a therapeutic regimen that involves the provision of at least two distinct therapies to achieve an indicated therapeutic effect. For example, a combination therapy may involve the administration of two or more distinct active ingredients, for example, an antibody and a chemotherapeutic agent, or an antibody directed to a first target and a second antibody directed to a second target. Alternatively, a combination therapy may involve the administration of an antibody and/or one or more other therapeutic agents, alone or together with the delivery of another treatment, such as radiation therapy and/or surgery. In the context of the administration of two or more distinct active ingredients, it is understood that the active ingredients may be administered as part of the same composition or as different compositions. When administered as separate compositions, the compositions comprising the different active ingredients may be administered at the same or different times, by the same or different routes, using the same of different dosing regimens, all as the particular context requires and as determined by the attending physician or medical caregiver.

"Immune stimulating agent" or "immuno-activating agent" refers to an agent, such as a compound or composition, which enhances an immune response, e.g., as compared to the immune response in the absence of the immune stimulating agent. In some embodiments, the immune stimulating agent can act by preventing suppression of the immune system or by activating the immune response.

"Vaccine" refers to a compound or composition which can be administered to humans or to animals in order to induce an immune system response; this immune system response can result in production of antibodies or result in the activation of certain cells, in particular antigen-presenting cells and immune system effector cells, such as T lymphocytes and B lymphocytes. The vaccine composition can be a composition for prophylactic purposes and/or for therapeutic purposes. "Cancer vaccine" refers to a compound or composition which elicits an immune response against a cancer. The immune response can be against a broad spectrum of cancers or against a specific cancer.

6.2 sMIC Binding Antibodies

The MHC class I chain-related gene A protein (MICA) and MHC class I chain-related gene B protein (MICB) proteins are members of the MHC Class I-related chain (MIC) family and the related UL-16 binding proteins (Leelayuwat et al., 1994, Immunogenetics 40:339-51; Bahram, 1994, Proc Natl Acad Sci USA. 91:6259-63; Fodil et al., 1996, Immunogenetics 44:351-7; Groh et al., 1999, Proc Natl Acad Sci USA. 96:6879-84; Bauer et al., 1999, Science 285(5428):727-9), and act as ligands that bind to C-type lectin-like activating receptor Natural Killer Group 2D (NKG2D) on immune effector cells, including NK, NKT and both $\alpha\beta$ and $\gamma\delta$ CD8$^+$ T cells. The MIC ligands are highly conserved in most mammals, with the exception of the rodent family, and are weakly related to MHC class I proteins. The MICA and MICB glycoproteins are about 84% identical at the amino acid sequence level (Bahram et al., 1994, Proc Natl Acad Sci USA. 91:6259-6263; Bahram, 1996, Immunogenetics 44:80-81; Bahram and Spies., 1996, Immunogenetics 43:230-233). The MICA and MICB proteins are stress-induced and are similar to MHC class I molecules; however, they are known not to associate with beta-2-microglobulin or bind peptides.

MIC proteins are expressed normally at low levels in the gut epithelium, on keratinocytes, monocytes and endothelial cells, but are induced to higher levels in stressed, transformed or some virally-infected cells (Groh et al., 1999, Proc Natl Acad Sci USA. 96:6879-84; Bauer et al., 1999, Science 285(5428):727-9; Zwirner et al., 1998, Immunogenetics 47:139-41). The interaction of NKG2D-bearing immune effector cells with stressed or diseased cells expressing MIC ligands on the cell surface creates a cellular immune response against the stressed/diseased cell that culminates in the death of the MIC expressing cells. Binding of the MIC ligands to NKG2D receptor-bearing immune cells stimulates the activation of naive T cells and can even induce cytotoxicity in the absence of appropriate TCR ligation. In humans, the NKG2D receptor can function as a co-stimulatory molecule along with DAP10 to impart the ligand binding signal to the interior of the cell via the phosphatidylinositol kinase (PI3K) pathway.

The expression of NKG2D ligands has been reported in many types of tumors and is thought to be the result of gene expression arising from stimulation of heat shock promoter elements as well as the intracellular detection of DNA damage resulting from either environmental insult or the increasing level of genomic instability associated with cancer. In cancer patients, the extracellular domain of MIC comprising alpha-1, -2 and -3 domains is frequently shed from cells and results in the down-modulation of its intended receptor, NKG2D, on effector immune cells (see, e.g., Groh et al., 2002, Nature 419:734-8). In some individuals, MICA glycoproteins are produced intracellularly that are not routinely destined to become cell surface membrane-bound, but instead are incorporated within exosomes and released outside the cell where interaction with NKG2D receptors on immune cells occurs (Ashiru et al., 2010, Cancer Res. 70:481-9). Studies suggest that these tumor-derived soluble MICA and MICB ligands (sMICA and sMICB) shed from the surface of tumor cells function like decoy molecules and lead to down-modulation of the NKG2D receptor on immune effector cells such as NK, NKT and various CD8$^+$ T cells. The formation of sMICA and sMICB appears to require the participation of protein disulfide isomerase ERp5, which may form transitory mixed disulfide complexes to enable proteolytic cleavage of the membrane bound MICA and MICB (Kaiser et al., 2007, Nature 447 (7143):482-6). The formation of sMICA and sMICB leads to the unusual situation where the effectors of the innate defense system, whose natural role is to seek and destroy transformed cells, are shut down by the immunosuppressive actions of these decoy MIC ligand molecules. Through this mechanism, tumor cells are capable of hiding from the immune system and can continue to grow unabated. As a further consideration, persistent NKG2D ligand expression and shedding promote proliferation of normally rare, immunosuppressive NKG2D$^+$ CD4$^+$ T cells in cancer patients, and is directly correlated with serum concentration of sMICA, thereby enabling NKG2D costimulation and expansion of immunosuppressive T cells (see, e.g., Groh et al., 2006, Nat Immunol. 7:755-62).

The adverse effects of sMICA and sMICB are supported by presence of significantly elevated levels of soluble MIC molecules (e.g., sMICA and/or sMICB) in the blood of advanced cancer patients as compared to healthy individuals (Groh et al., 2002, Nature 419:734-8; Salih et al., 2002, J Immunol. 169:4098-102). In many cases these high levels appear to correlate directly with both the clinical staging of the cancer and to poor clinical outcomes (Doubrovina et al., 2003, J Immunol. 171:6891-9; Wu et al., 2004, J Clin Invest. 114:560-8; Holdenreider et al., 2006, Intl J Cancer 118:684-7). In vitro experiments have also shown that addition of recombinant or tumor cell-derived sMIC proteins can decrease the level of NKG2D receptors on effector immune cells such as NK and T cells and that this effect can be blocked by neutralizing antibodies to the soluble ligands through interference with receptor binding (Groh et al., 2002, Nature 419:734-8). Thus, reduced NKG2D expression on both systemic and tumor-infiltrated effectors cells can limit the immune responses against tumors in sMIC$^+$ patients. However, it is highly unlikely that the aforementioned specific neutralizing rodent antibodies could be useful as human therapeutics (even if humanized) as they would also bind cell-bound MIC ligands and could therefore create unwanted immune responses against certain cells expressing endogenous MIC ligands under normal conditions.

Soluble forms of MICA and MICB are also implicated in viral infection processes. For example, Respiratory Syncytial Virus (RSV) infections in respiratory epithelial cells lead to the upregulation of cell surface expression of MICA and circulating levels of sMICA (Zdrenghea et al., 2012, Eur Respir J. 39:712-20). These higher levels of sMICA may impair virus clearance and potentially aid in prolonging the infection. Again, NK cells are known to play key cytotoxicity roles in the response of the immune system to RSV infections just as they function in detection of transformed cells in the proposed immunosurveillance system. Suppression of NK cell function via sMIC-induced down-modulation of NKG2D receptors on effector immune cells could either represent a viral response for avoiding immune detection or a cellular safety mechanism for reducing cytolysis of uninfected bystander cells once antiviral gamma interferon is released during the infection of the cell. Considering the delicate balance between development of an adequate immune response to the virus and the consequential loss of NK cell function known to occur in RSV infections, the excessive levels of sMICA may attenuate the overall antiviral response. Efforts to reduce the levels of sMICA during these RSV infections are therefore warranted especially in the very young and in the elderly patient where prolonged viral infections frequently result in serious damage to the lining of the respiratory tract and even death as a result of difficult-to-treat secondary bacterial infections. Release of soluble NKG2D ligands has also been described in viral infections of humans with Human Immunodeficiency Virus type 1 (HIV-1) (Nolting et al., 2010, Virology 406:12-20) or with Hepatitis B Virus (HBV) that result in the onset of hepatocellular carcinoma (HCC). Matusali et al., 2013, FASEB J. 27(6):2440-50 reported that NKG2D ligand shedding by HIV-1 infected lymphocytes induces NKG2D down-regulation in NK and CD8$^+$ T cells and led to dampening of the immune response against the virally-infected cells. Levels of sMICA, sMICB and sULBP2 were all elevated in the medium of in vitro HIV-1 infected CD4$^+$ T cells. Moreover, chronically-infected patients with HIV-1 possessed 7-fold higher levels of sMICA compared with aviremic Highly Active Anti-Retroviral Therapy (HAART)-treated patients, and a similar trend was noted for sULBP2 but not with sMICB. Reducing the levels of soluble NKG2D ligands in HIV-1 infections by the antibodies and methods described herein may serve to improve the cytotoxic functionality of NK cells by increasing NKG2D cell-surface levels and thereby imparting an overall improvement in immunosurveillance and NK control of HIV-1 infections. Also, Kumar et al., 2012, PLOS One 7:1-6 E44743 found a significant elevation of sMICA in HBV-induced HCC cases. In fact, HBV$^+$ HCC patients who had elevated levels of sMICA had significantly worse survivability than those with normal levels, presumably because higher sMICA levels may cause inactivation of the immune surveillance system against HBV-infected cells. Again, reduction in circulating sMIC ligands would be consistent with improved immune reactivity towards chronic viral infections.

Given their role in immunosurveillance, MICA and MICB and cognate receptor NKG2D have been targets for development of therapeutics for treating various diseases associated with MICA and MICB expression, such as cancers and autoimmune diseases. For example, patent publication WO 98/019167 describes cell stress regulated human MIC Class 1 gene and treatment of certain disease states including graft versus host disease (GVHD) and cancers. Patent publications WO 03/089616, US20050233391, US20100316650; and U.S. Pat. No. 7,771,718 describe soluble MIC polypeptides as markers for diagnosis, prognosis, and treatment of cancer and autoimmune diseases or conditions. Patent publications U.S. Pat. No. 7,666,417 and WO 2006/024367 describe NKG2D receptor/NKG2D ligand interaction blockers for treating autoimmune diseases. Patent publications WO 2008/036981 and U.S. Pat. No. 7,959,916 describe methods of treating MICA-related disorders through use of anti-MICA antibodies and modulation of ERp5 (protein disulfide isomerase) activity, such as by ERp5 antibodies or by modulating ERp5 expression. U.S. Pat. No. 8,182,809 also describes methods for treating cancer by inhibiting MIC shedding (e.g., formation of soluble MICA) by use of an anti-MICA antibody. Patent publication WO2014/140904 describes antibodies which discriminate between soluble MIC proteins and cell membrane bound MIC proteins.

The present disclosure provides binding agents, particularly antibodies, which bind to an epitope on the alpha-3 domain of MICA and/or MICB, where the antibodies bind to sMICA and/or sMICB but do not bind to cell membrane bound MICA and/or MICB. The ability of the antibodies to discriminate between sMIC and the cell-bound MIC provides a therapeutic approach in which sMICA and/or sMICB are neutralized, thereby mitigating the detrimental effects of sMICA and/or sMICB released from cells, e.g., immunosuppression, in certain types of diseases while preserving the innate immune response against cells expressing MICA and/or MICB protein on the cell surface, such as cancers cells expressing MIC proteins. As described herein, the sMIC (e.g., sMICA and/or MICB) are truncated proteins that typically lack the transmembrane domain and cytoplasmic tail but retain the three extracellular domains alpha-1, alpha-2 and alpha-3. The extracellular domain of the reference MICA amino sequence of FIG. 1A extends from about amino acid residues 24 to about 297, and up to residue 307, and for the reference MICB amino sequence of FIG. 1B extends from about amino acid residues 24 to about 297, and up to residue 307. The alpha-3 domain in the reference MICA amino sequence of FIG. 1A extends from about amino acid residues 205 to 296/297, while the alpha-3 domain in the reference MICB amino acid sequence of FIG. 1A extends from about amino acid residues 205 to 296/297. The sMIC proteins, which can be found in various types of tumors and cancers, can have variable carboxy terminal ends owing to the process by which the soluble forms are generated. Without being bound by theory, the naturally occurring soluble forms appear to result from the actions of a disulfide isomerase, endoplasmic reticulum protein 5, also referred to as ERp5, PDIA6 or P5, which forms a complex with the MICA or MICB protein and reduces the disulfide bond in the alpha-3 domain. The sMIC proteins are released after proteolytic cleavage near the cell membrane. These truncations appear not to occur at specific proteolytic recognition sites (see, e.g., Wang et al., 2009, Biochem Biophys Res Comm. 387:476-81) but instead occur in a random fashion within the alpha-3 domain sequence upstream of the transmembrane section and downstream of the reported conserved ERp5 binding site at N238-T243 of MICA or homologous sequence in MICB.

In some embodiments, the antibody of the disclosure binds an epitope comprising the amino acid sequence GDVL (SEQ ID NO:23) on the alpha-3 domain of MIC protein, e.g., MICA and/or MICB. The sequence GDVL (SEQ ID NO:23) is present at amino acid positions 254 to 257 in the reference sequence of MICA*001 presented in FIG. 1A (SEQ ID NO:1), and at amino acid positions 254 to 257 in the reference sequence of MICB*001 FIG. 1B (SEQ ID NO:2). In some embodiments, the antibodies bind one or more amino acid residue 254G, amino acid residue 255D, amino acid residue 256V, and/or amino acid residue 257L in the epitope sequence GDVL (SEQ ID NO:23) of the alpha-3 domain of the MIC protein. In some embodiments, the antibody binds to 2, 3 or all of the foregoing amino acid residues in the alpha-3 domain.

In some embodiments, the epitope can have an additional 1, 2, 3, 4, 5 or more amino acids at the amino terminal and/or carboxy terminal end, where the additional amino acids can be those found on the naturally occurring MICA or MICB amino acid sequence surrounding the described defined region or the defined amino acid sequence.

In some embodiments, the antibody binds to an epitope in the amino acid sequence comprising QQWGDVLP (SEQ ID NO:22) on the alpha-3 domain of sMIC protein, e.g., sMICA and/or sMICB. The sequence QQWGDVLP (SEQ ID NO:22) is present at amino acid positions 251 to 258 in the reference sequence of MICA*001 presented in FIG. 1A (SEQ ID NO:1), and at amino acid positions 251 to 258 in the reference sequence of MICB*001 presented in FIG. 1B (SEQ ID NO:2). In some embodiments, the antibody binds to one or more of amino acid residue Q, amino acid residue Q, amino acid residue W, amino acid residue G, amino acid residue D, amino acid residue V, amino acid residue L, and/or amino acid residue P in the sequence QQWGDVLP (SEQ ID NO:22) of the alpha-3 domain of MIC protein. In some embodiments, the antibody binds to 2, 3, 4 or more of the foregoing amino acid residues in the alpha-3 domain.

In some embodiments, the antibody binds to the specified epitope present in various alleles of MICA existing in the human population, such as the identified MICA alleles available in Robinson et al., 2003, "IMGT/HLA and IMGT/MHC: Sequence databases for the study of the major histocompatibility complex", Nucleic Acids Res. 31:311-314 and the Anthony Nolan Research Institute world wide web site www.anthonynolan.org.uk/HIG/data.html; which are incorporated herein by reference. Thus, in some embodiments, the antibody binds to the specified epitope present in any of the MICA allelic variants, including human MICA allelic variants selected from MICA*001, MICA*002:01, MICA*002:02, MICA*002:03, MICA*002:04, MICA*004, MICA*005, MICA*006, MICA*007:01, MICA*007:02, MICA*007:03, MICA*007:04, MICA*007:05, MICA*007:06, MICA*008:01:01, MICA*008:01:02, MICA*008:02, MICA*008:03, MICA*008:04, MICA*008:05, MICA*009:01, MICA*009:02, MICA*010:01, MICA*010:02, MICA*011, MICA*012:01, MICA*012:02, MICA*012:03, MICA*012:04, MICA*013, MICA*014, MICA*015, MICA*016, MICA*017, MICA*018:01, MICA*018:02, MICA*019, MICA*020, MICA*022, MICA*023, MICA*024, MICA*025, MICA*026, MICA*027, MICA*028, MICA*029, MICA*030, MICA*031, MICA*032, MICA*033, MICA*034, MICA*035, MICA*036, MICA*037, MICA*038, MICA*039, MICA*040, MICA*041, MICA*042, MICA*043, MICA*044, MICA*045, MICA*046, MICA*047, MICA*048, MICA*049, MICA*050, MICA*051, MICA*052, MICA*053, MICA*054, MICA*055, MICA*056, MICA*057, MICA*058, MICA*059, MICA*060, MICA*061, MICA*062, MICA*064N, MICA*065, MICA*066, MICA*067, MICA*068, MICA*069, MICA*070, MICA*072, MICA*073, MICA*074, MICA*075, MICA*076, and MICA*077.

In some embodiments, the antibody binds to the specified epitope present in various alleles of MICB existing in the human population, such as the identified MICB alleles available in Robinson et al., 2003, "IMGT/HLA and IMGT/MHC: Sequence databases for the study of the major histocompatibility complex", Nucleic Acids Res. 31:311-314 and the Anthony Nolan Research Institute world wide web site www.anthonynolan.org.uk/HIG/data.html; which are incorporated herein by reference. Thus, in some embodiments, the antibody binds to the specified epitope present in any of the MICB allelic variants, including human MICB allelic variants selected from MICB*001, MICB*002:01:01, MICB*002:01:02, MICB*003, MICB*004:01:01, MICB*004:01:02, MICB*005:01, MICB*005:02:01, MICB*005:02:02, MICB*005:02:03, MICB*005:02:04, MICB*005:03, MICB*005:04, MICB*005:05, MICB*005:06, MICB*005:07, MICB*005:08, MICB*006, MICB*007, MICB*008, MICB*009N, MICB*010, MICB*011, MICB*012, MICB*013, MICB*014, MICB*015, MICB*016, MICB*018, MICB*019, MICB*020, MICB*021N, MICB*022; MICB*023, MICB*024, MICB*025, MICB*026, MICB*027, MICB*028, and MICB*029.

It is to be understood that while the epitope defined above is part of the MIC protein bound by the antibody of the disclosure, it does not preclude the possibility that antibody could interact with other sites on MIC protein in addition to the specified epitope.

In some embodiments, the antibody which binds to the specified epitope binds specifically to a sMIC protein, e.g., sMICA and/or sMICB, but does not bind specifically to the extracellular domain of membrane-bound MIC, e.g., MICA and/or MICB, particularly a MIC protein present on the cell surface. In some embodiments, the antibody is capable of binding specifically to sMICA but does not bind specifically to the extracellular domain of membrane-bound MICA. In some embodiments, antibody is capable of binding specifically to sMICB but does not bind specifically to the extracellular domain of membrane-bound MICB. In some embodiments, the antibody binds to the alpha-3 domain of sMICA and/or sMICB but does not bind specifically to the alpha-3 domain in the extracellular domain of a membrane-bound MICA and/or MICB. In some embodiments, the antibody binds to the alpha-3 domain of sMICA but does not bind specifically to the alpha-3 domain in the extracellular domain of a membrane-bound MICA. In some embodiments, the antibody binds to the alpha-3 domain of sMICB but does not bind specifically to the alpha-3 domain in the extracellular domain of a membrane-bound MICB.

In some embodiments, the antibody binds to an epitope comprising an amino acid sequence GDVL (SEQ ID NO:23) in the alpha-3 domain of a sMICA and/or sMICB but does not bind specifically to the same epitope in the alpha-3 domain of a membrane-bound MICA and/or MICB. In some embodiments, the antibody binds to an epitope comprising an amino acid sequence GDVL (SEQ ID NO:23) in the alpha-3 domain of sMICA but does not bind specifically to the same epitope in the alpha-3 domain of a membrane-bound MICA. In some embodiments, the antibody binds to an epitope comprising an amino acid sequence GDVL (SEQ ID NO:23) in the alpha-3 domain of sMICB but does not bind specifically to the same epitope in the alpha-3 domain of a membrane-bound MICB.

In some embodiments, the antibody binds to an epitope in the amino acid sequence comprising QQWGDVLP (SEQ ID NO:22) in the alpha-3 domain of a sMICA and/or sMICB but does not bind specifically to the same epitope in the alpha-3 domain of a membrane-bound MICA and/or MICB. In some embodiments, the antibody binds to an epitope in the amino acid sequence comprising QQWGDVLP (SEQ ID NO:22) in the alpha-3 domain of sMICA but does not bind specifically to the same epitope in the alpha-3 domain of a membrane-bound MICA. In some embodiments, the antibody binds to an epitope in the amino acid sequence comprising QQWGDVLP (SEQ ID NO:22) in the alpha-3 domain of sMICB but does not bind specifically to the same epitope in the alpha-3 domain of a membrane-bound MICB.

In some embodiments, the antibody binds to sMIC protein containing the alpha-3 domain, e.g., sMICA and/or sMICB, particularly sMICB, with at least 10 fold or greater, at least 50 fold or greater, at least 100 fold or greater, at least 500 fold or greater, or at least 1000 fold or greater specificity as compared to the corresponding membrane bound MIC protein. In some embodiments, the antibody binds to an isolated alpha-3 domain of MIC protein, e.g., MICA and/or sMICB, particularly the alpha-3 domain of sMICB, with at least 10 fold or greater, at least 50 fold or greater, at least 100 fold or greater, at least 500 fold or greater, or at least 1000 fold or greater specificity as compared to the binding to the corresponding membrane bound MIC protein. In some embodiments, the differential specificity is with respect to MICA. In some embodiments, the differential specificity is with respect to MICB. In some embodiments, the differential specificity is with respect to MICB produced by human prostate cancer cell line DU-145.

In some embodiments, the antibodies of the present disclosure include an antibody that competes with a reference antibody for binding to the specified epitope on sMICA and/or sMICB. In some embodiments, ability to compete with the reference antibody can be measured as an inhibition constant Ki, which is calculated according to the following:

$$Ki = IC_{50}/(1 + [\text{Reference Antibody Concentration}])/K_D$$

where $IC_{50}$ is the competing antibody concentration resulting in 50% inhibition in binding of the reference antibody, and $K_D$ is the equilibrium dissociation constant of the reference antibody.

In some embodiments, the antibody competes with the reference antibody for binding to the specified epitope on sMICA and/or sMICB with the same or greater equilibrium association constant $K_A$, or the same or lower $K_D$ as the reference antibody. In some embodiments, the antibody competes with the reference antibody for binding to the specified epitope on sMICB produced by prostate cancer cell line DU-145. In some embodiments, the reference antibody is monoclonal antibody 5C9. In some embodiments, competition between antibodies can be determined by an assay in which the antibody of interest or candidate antibody inhibits specific binding of a reference antibody to a common antigen, e.g., alpha-3 domain of sMIC. Numerous types of competitive binding assays are known and can be used, including, for example, solid phase direct or indirect radio-immunoassay (RIA), solid phase direct or indirect enzyme immunoassay (EIA), sandwich competition assay, solid phase direct biotin-avidin EIA, solid phase direct labeled assay, and solid phase direct labeled sandwich assay.

In some embodiments, an antibody is considered to compete with a reference antibody if it decreases binding of the reference antibody by at least about 20% or more, for example, by at least about 20%, 30%, 40%, 50%, 60%, 70%, 80%, 90%, 95% or even more, or by a percentage ranging between any of the foregoing values, at a reference antibody concentration that is 80% of maximal binding under the specific assay conditions used, and an antibody concentration that is 10-fold higher than the reference antibody concentration.

In some embodiments, the antibody binds to sMIC produced by prostate cancer cell line DU-145 with equal or greater equilibrium association constant $K_A$ as compared to antibody 5C9 described herein. In some embodiments, the antibody binds to sMICA produced by prostate cancer cell line DU-145 with equal or greater equilibrium association constant $K_A$ as compared to antibody 5C9 described herein. In some embodiments, the antibody binds to sMICB produced by prostate cancer cell line DU-145 with equal or greater equilibrium association constant $K_A$ as compared to antibody 5C9 described herein.

In some embodiments, the antibody binds to sMIC produced by prostate cancer cell line DU-145 with equal or lower equilibrium dissociation constant $K_D$ as compared to antibody 5C9 described herein. In some embodiments, the antibody binds to sMICA produced by prostate cancer cell line DU-145 with equal or lower equilibrium dissociation constant $K_D$ as compared to antibody 5C9 described herein. In some embodiments, the antibody binds to sMICB produced by prostate cancer cell line DU-145 with equal or lower equilibrium dissociation constant $K_D$ as compared to antibody 5C9 described herein.

In some embodiments, the antibody is characterized by an affinity ($K_A$=equilibrium association constant or the ratio of association rate constant $k_{on}$/dissociation rate constant $k_{off}$) for the sMICA and/or sMICB protein, or the alpha-3 domain thereof, in the range of about $10^4$ to about $10^{12}$ $M^{-1}$, about $10^5$ to about $10^{12}$ $M^{-1}$, about $10^6$ to about $10^{12}$ $M^{-1}$, about $10^7$ to about $10^{12}$ $M^{-1}$, about $10^8$ to about $10^{12}$ $M^{-1}$, about $10^7$ to about $10^{11}$ $M^1$, about $10^8$ to about $10^{11}$ $M^{-1}$, about $10^7$ to about $10^{10}$ $M^{-1}$, or about $10^8$ to about $10^{10}$ $M^{-1}$. In some embodiments, the binding agent has a $K_A$ of at least about $1\times10^7$ $M^{-1}$ or higher, at least about $1\times10^8$ $M^{-1}$ or higher, at least about $1\times10^9$ $M^{-1}$ or higher, at least about $1\times10^{10}$ $M^{-1}$ or higher, at least about $1\times10^{11}$ $M^{-1}$ or higher, or at least about $1\times10^{12}$ $M^{-1}$ or higher. In some embodiments, the antibody has a $K_A$ of the antibody 5C9 described herein. In some embodiments, the antibody has a $K_A$ or about $1\times10^8$ $M^{-1}$ to about $1\times10^9$ $M^{-1}$ or higher (e.g., affinity of antibody 5C9). In some embodiments, the $K_A$ is measured with respect to sMICB produced by prostate cancer cell line DU-145.

In some embodiments, the antibody is characterized by an equilibrium dissociation constant ($K_D$=equilibrium dissociation constant or the ratio of dissociation rate constant $k_{off}$/association rate constant $k_{on}$) for the sMICA and/or sMICB protein, or the alpha-3 domain thereof, in the range of about $10^{-4}$ to about $10^{-12}$ M, about $10^{-5}$ to about $10^{-12}$ M, about $10^{-6}$ to about $10^{-12}$ M, about $10^{-7}$ to about $10^{-12}$ M, about $10^{-8}$ to about $10^{-12}$ M, about $10^{-7}$ to about $10^{-11}$ M, about $10^{-8}$ to about $10^{-11}$ M, about $10^{-7}$ to about $10^{-10}$ M, or about $10^{-8}$ to about $10^{-10}$ M. In some embodiments, the binding agent has a $K_A$ of about $1\times10^{-7}$ M or less, about $1\times10^{-8}$ M or less, about $1\times10^{-9}$ M or less, about $1\times10^{-10}$ M or less, about $1\times10^{-11}$ M or less, or about $1\times10^{-12}$ M or less. In some embodiments, the antibody has a $K_D$ of the antibody 5C9 described herein. In some embodiments, the antibody has a $K_D$ of about $1\times10^{-9}$ M to about $1\times10^{-10}$ M or less (antibody 5C9). In some embodiments, the $K_D$ is measured with respect to sMICB produced by prostate cancer cell line DU-145.

In some embodiments, the antibody is characterized by a $k_{on}$ association rate constant for the sMICA and/or sMICB protein, or the alpha-3 domain thereof, in the range of about $10^3$ to about $10^9$ $M^{-1}s^{-1}$ or greater, about $10^4$ to about $10^9$ $M^{-1}s^{-1}$ or greater, about $10^5$ to about $10^9$ $M^{-1}s^{-1}$ or greater, about $10^6$ to about $10^9$ $M^{-1}s^{-1}$ or greater, about $10^7$ to about $10^9$ $M^{-1}s^{-1}$ or greater, about $10^4$ to about $10^8$ $M^{-1}s^{-1}$ or greater, or about $10^5$ to about $10^8$ $M^{-1}s^{-1}$ or greater. In some embodiments, the binding agent has a $k_{on}$ association rate constant of at least about $1\times10^3$ $M^{-1}s^{-1}$ or greater, at least about $1\times10^4$ $M^{-1}s^{-1}$ or greater, at least about $1\times10^5$ $M^{-1}s^{-1}$ or greater, at least about $1\times10^6$ $M^{-1}s^{-1}$ or greater, at least about $1\times10^7$ $M^{-1}s^{-1}$ or greater, at least about $1\times10^8$ $M^{-1}s^{-1}$ or greater, or at least about $1\times10^9$ $M^{-1}s^{-1}$ or greater. In some embodiments, the antibody has a $k_{on}$ association rate constant characteristic of the antibody 5C9 described herein. In some embodiments, the $k_{on}$ is measured with respect to sMICB produced by prostate cancer cell line DU-145.

In some embodiments, the antibody of the disclosure is characterized by a $k_{off}$ dissociation rate constant for the sMICA and/or sMICB protein, or the alpha-3 domain thereof, of about $10^{-3}$ to about $10^{-10}$ s$^{-1}$ or less, about $10^{-4}$ to about $10^{-10}$ s$^{-1}$ or less, about $10^{-5}$ to about $10^{-10}$ s$^{-1}$ or less, about $10^{-6}$ to about $10^{-10}$ s$^{-1}$ or less, about $10^{-7}$ to about $10^{-10}$ s$^{-1}$ or less, about $10^{-5}$ to about $10^{-9}$ s$^{-1}$ or less, about $10^{-6}$ to about $10^{-9}$ s$^{-1}$ or less, about $10^{-5}$ to about $10^{-8}$ s$^{-1}$ or less, or about $10^{-6}$ to about $10^{-8}$ s$^{-1}$ or less. In some embodiments, the binding agent has a $k_{off}$ dissociation rate constant of about $10^{-3}$ s$^{-1}$ or less, about $10^{-4}$ s$^{-1}$ or less, about $10^{-5}$ s$^{-1}$ or less, about $10^{-6}$ s$^{-1}$ or less, about $10^{-7}$ s$^{-1}$ or less, about $10^{-8}$ s$^{-1}$ or less, about $10^{-9}$ s$^{-1}$ or less or about $10^{-10}$ s$^{-1}$ or less. In some embodiments, the antibody has a $k_{off}$ dissociation rate constant characteristic of the antibody 5C9 described herein. In some embodiments, the $k_{off}$ is measured with respect to sMICB produced by prostate cancer cell line DU-145.

The $K_A$ or $K_D$ as well as the $k_{on}$ and $k_{off}$ rate constants can be determined any number of methods known in the art, such as by surface plasmon resonance (SPR) screening (e.g., BIAcore™ SPR analytical device, as described in Popov et al., 1996, Mol Immunol. 33:493-502; and Karlsson et al., 1991, J Immunol. Methods 145:229-40, incorporated herein by reference). In some embodiments, the $K_A$ or $K_D$ as well as the $k_{on}$ and $k_{off}$ rate constants can be determined by Bio-Layer Interferometry (BLI), which is based on interference pattern of white light reflected from two surfaces (see, e.g., Rich and Myszka, 2007, Anal Biochem. 361:1-6; Fransson et al., 2010, J Mol Biol. 398(2):214-31) and commercially available as Octet RED96 (ForteBio, Menlo Park, Calif., USA). Other methods for determining affinity and kinetic parameters include equilibrium dialysis and globulin precipitation techniques (see, e.g., Azimzadeh et al., 1990, J Mol Recognit. 3(3):108-16).

In some embodiments, the antibody can have the effect of enhancing immune response, including one or more of the following: upregulation of T cell, natural killer (NK) cell, natural killer T (NKT) cell, γδ T cell, αβ T cell, and/or B cell function. In some embodiments, upregulation of one or more of T cell, natural killer (NK) cell, natural killer T (NKT) cell, γδ T cell, αβ T cell, and B cell function includes enhancement and/or endowment of activity capable of inhibiting cancer progression or inhibiting viral infection, as further described herein.

In some embodiments, the antibody with the specified characteristics is capable of attenuating the level of sMICB in animals inoculated with prostate cancer cell line DU-145 xenograft, such as DU-145 xenografted into mice, particularly DU-145 xenografted into Rag2$^{-/-}$ mice, more particularly according to the process set forth in Example 5. In some embodiments, the antibody with the specified characteristics is capable of attenuating the growth of xenografted prostate cancer cell line DU-145, such as DU-145 xenografted into mice, particularly DU-145 xenografted into Rag2$^{-/-}$ mice, more particularly according to the process set forth in Example 5. In some embodiments, the ability of the antibody to attenuate the level of sMICB in animals with xenografted DU-145 cells and/or the ability to attenuate growth of xenografted DU-145 cells is in combination with cytokine IL-12.

In some embodiments, the antibody of the disclosure has one or more of the following characteristics: binds to an epitope in the amino acid sequence comprising QQWGDVLP (SEQ ID NO:22) on the alpha-3 domain of sMIC protein, particularly the epitope comprising the amino acid sequence GDVL (SEQ ID NO:23) in the alpha-3 domain; binds specifically to sMIC, e.g., sMICA and/or sMICB, but does not bind specifically to extracellular domain of membrane-bound MIC, e.g., MICA and/or MICB, particularly a MIC protein present on the cell surface; binds to sMIC produced by prostate cancer cell line DU-145 with equal or greater equilibrium association constant $K_A$ as compared to antibody 5C9; binds to sMIC produced by prostate cancer cell line DU-145 with equal or lower equilibrium dissociation constant $K_D$ as compared to antibody 5C9; capable of attenuating the level of sMICB in mice inoculated with prostate cancer cell line DU-145 xenograft; capable of attenuating the growth of xenografted prostate cancer cell line DU-145, such as DU-145 xenografted into mice, particularly DU-145 xenografted into Rag2$^{-/-}$ mice; and capable of increasing the expression of IFN-γ, particularly when used in combination with IL-12.

In some embodiments, the antibody of the present disclosure has the following characteristics: binds to an epitope in the amino acid sequence comprising QQWGDVLP (SEQ ID NO: 22) on the alpha-3 domain of sMIC protein, particularly the epitope comprising the amino acid sequence GDVL (SEQ ID NO: 23) in the alpha-3 domain; but does not bind specifically to the same epitope in the extracellular domain of membrane-bound MIC, e.g., MICA and/or MICB, particularly a MIC protein present on the cell surface; and at least one of the above characteristics with regards to prostate cancer cell line DU-145, e.g., binding to sMICB, attenuating level of sMICB, and/or attenuating growth of xenografted DU-145.

In the embodiments herein, the antibody with the relevant properties can be polyclonal, monoclonal, non-human, chimeric, humanized, fully human antibody, engineered antibody or fragment of an antibody. The antibody can be monospecific (i.e., binds to single epitope—monovalent) or multi-specific (i.e., binds to more than a single epitope—multivalent), including bispecific and trispecific antibodies (see, e.g., Sharkey et al., 2010, Cancer Biother Radiopharm. 25(1):1-12); U.S. patent publication 20080069820; incorporated herein by reference). In some embodiments, the antibody can be a single chain antibody or diabodies, which are small bivalent and bispecific antibody fragments. In some embodiments, the antibody can comprise a non-human antibody, such as prepared from goat, horse, cow, chicken, camel, llama, rabbit, rat, or mouse, or a chimeric or humanized antibody based on a non-human antibody. In some embodiments, the antibody can comprise a portion of or all of the constant region of an antibody. In some embodiments, the antibody comprises a constant region corresponding to an isotype selected from IgA (e.g., IgA$_1$ or IgA$_2$); IgD, IgE, IgG (IgG$_1$, IgG$_2$, IgG$_3$, IgG$_4$) and IgM.

In some embodiments, the antibody comprises the antigen binding characteristics of antibody 5C9 described herein and in the Examples. Epitope mapping studies identify the epitope bound by the 5C9 antibody to be in at least the amino acid sequence QQWGDVLP (SEQ ID NO:22), particularly the amino acid sequence GDVL (SEQ ID NO:23) in the alpha-3 domain of sMICA and/or sMICB. The 5C9 antibody does not bind to membrane bound MICA/MICB expressed in cells (see, e.g., FIG. 9). Accordingly, in some embodiments, the antibody comprises one or more of CDR L1, CDR L2, and CDR L3 in the light chain variable region amino acid sequence comprising SEQ ID NO:24, more particularly SEQ ID NO:25:

(SEQ ID NO: 25)
MTQTPLSLPVSLGDQASISCRSSQSIVHSNGNTYLEWYLQKPGQSPKLLI

YKVSNRFSGVPDRFSGSGSGTDFTLKISRVEAEDLGVYYCFQGSHVPFTF

GSGTKLEIK;

In some embodiments, the antibody comprises one or more of CDR H1, CDR H2 and CDR H3 in the heavy chain variable region amino acid sequence comprising SEQ ID NO:28, more particularly SEQ ID NO:29:

(SEQ ID NO: 29)
QVQLQQSGAELVRPGTSVKVSCKASGYAFTNYLIEWVKQRPGQGLEWIGL

IYPGSGGTNYNEKFKGKATLTADKSSSTAYMQLSSLTSDDSAVYFCARIY

YGNRDYGMDYWGQGTSVTVSSAK.

In some embodiments, the antibody comprises the CDR L1, CDR L2, and CDR L3 in the light chain variable region amino acid sequence comprising SEQ ID NO:25 and comprises the CDR H1, CDR H2 and CDR H3 in the heavy chain variable region amino acid sequence comprising SEQ ID NO:29.

As is understood in the art and as described herein, the amino acid position/boundary delineating the CDR regions of an antibody can vary, depending on the context and the various methods known in the art for determining the CDR regions. Some positions within the variable regions can be viewed as hybrid CDRs in that the positions can be within a CDR region under one set of criteria while being deemed to be outside a CDR region under a different set of criteria. In some embodiments, the CDRs in the foregoing variable light and variable heavy chains can be delineated using the Kabat, Chothia, or AbM schemes, as described herein, in particular based on the Kabat numbering system. Exemplary CDRs based on Kabat criteria are presented in Table 1.

TABLE 1

| Mono-clonal | KABAT | | |
|---|---|---|---|
| | CDR L1 | CDR L2 | CDR L3 |
| 5C9 VL | RSSQSIVHSNGNTYLE (SEQ ID NO: 40) | KVSNRFS (SEQ ID NO: 41) | FQGSHVPFT (SEQ ID NO: 42) |
| | CDR H1 | CDR H2 | CDR H3 |
| 5C9 VH | NYLIE (SEQ ID NO: 43) | LIYPGSGGT NYNEKFKG (SEQ ID NO: 44) | IYYGNRDYGMDY (SEQ ID NO: 45) |

While the CDR sequences above have been defined using criteria of Kabat, it is to be understood that CDRs can be based on Chothia, AbM, and other methods, including the "Contact" approach, IMGT approach (Lefranc et al., 2003, Dev Comp Immunol. 27:55-77) and computational programs such as Paratome (Kunik et al., 2012, Nucl Acids Res. W521-4; www.ofranlab.org/paratome/).

In some embodiments, the antibody comprises at least 1, 2, or all 3 of the CDRs in the light chain variable region of amino acid sequence of SEQ ID NO:25. In some embodiments, the antibody comprises at least 1, 2, or all 3 of the CDRs the heavy chain variable region of amino acid sequence of SEQ ID NO:29. In some embodiments, the antibody comprises at least 1, 2, or all 3 of the CDRs in the light chain variable region of amino acid sequence of SEQ ID NO:25 and at least 1, 2, or all 3 of the CDRs the heavy chain variable region of amino acid sequence of SEQ ID NO:29.

In some embodiments, the antibody comprises at least 1, 2, or 3 of the CDRs selected from: CDR L1 comprising an amino acid sequence RSSQSIVHSNGNTYLE (SEQ ID NO:40); CDR L2 comprising an amino acid sequence KVSNRFS (SEQ ID NO:41); and CDR L3 comprising an amino acid sequence FQGSHVPFT (SEQ ID NO:42). In some embodiments, the antibody comprises at least 1, 2, or 3 of the CDRs selected from: CDR H1 comprising an amino acid sequence NYLIE (SEQ ID NO:43); CDR H2 comprising an amino acid sequence LIYPGSGGTNYNEKFKG (SEQ ID NO:44); and CDR H3 comprising an amino acid sequence IYYGNRDYGMDY (SEQ ID NO:45).

In some embodiments, the antibody comprises at least 1, 2, 3, 4, 5 or all 6 of the CDRs selected from: CDR L1 comprising an amino acid sequence RSSQSIVHSNGNTYLE (SEQ ID NO:40); CDR L2 comprising an amino acid sequence KVSNRFS (SEQ ID NO:41); CDR L3 comprising an amino acid sequence FQGSHVPFT (SEQ ID NO:42); CDR H1 comprising an amino acid sequence NYLIE (SEQ ID NO:43); CDR H2 comprising an amino acid sequence LIYPGSGGTNYNEKFKG (SEQ ID NO:44); and CDR H3 comprising an amino acid sequence IYYGNRDYGMDY (SEQ ID NO:45).

In some embodiments, for any of the embodiments of the antibody containing one or more of the defined CDRs, the CDR sequence may have one or more amino acid substitutions, deletions, and/or insertions, provided the antibody retains the relevant functional properties, e.g., of binding specifically to the specified epitope in the alpha 3 domain of sMICA and/or sMICB but does not bind to the epitope on cell membrane bound MICA and/or MICB. In some embodiments, the CDR sequence has at least 1, 2, 3, 4, 5 or more amino acid substitutions, deletions, and/or insertions. In some embodiments, where the CDR has an amino acid substitution, the substitution comprises a conservative substitution.

In some embodiments, the antibody comprises a light chain variable region VL having at least 80%, 85%, 90%, 91%, 92%, 93%, 94%, 95%, 96%, 97%, 98%, 99% or greater sequence identity to the amino acid sequence of SEQ ID NO:24, more particularly SEQ ID NO:25.

In some embodiments, the antibody comprises a heavy chain variable region VH having at least 80%, 85%, 90%, 91%, 92%, 93%, 94%, 95%, 96%, 97%, 98%, 99% or greater sequence identity to the amino acid sequence of SEQ ID NO:28, more particularly SEQ ID NO:29.

In some embodiments, the antibody comprises a light chain variable region VL having at least 80%, 85%, 90%, 91%, 92%, 93%, 94%, 95%, 96%, 97%, 98%, 99% or greater sequence identity to the amino acid sequence of SEQ ID NO:24, more particularly SEQ ID NO:25, and a heavy chain variable region VH having at least 80%, 85%, 90%, 91%, 92%, 93%, 94%, 95%, 96%, 97%, 98%, 99% or greater sequence identity to the amino acid sequence of SEQ ID NO:28, more particularly SEQ ID NO:29.

In some embodiments, the antibody comprises a light chain variable region VL comprising an amino acid sequence of SEQ ID NO:24, more particularly SEQ ID NO:25, and a heavy chain variable region VH comprising an amino acid sequence of SEQ ID NO:28, more particularly SEQ ID NO:29.

In some embodiments, the antibody with the defined level of amino acid sequence identity to the light chain variable region has one or more amino acid substitutions, deletions and/or insertions as compared to the VL reference sequence of SEQ ID NO:24, more particularly SEQ ID NO:25. In some embodiments, the antibody comprises 1, 2, 3, 4, 5 or more amino acid substitutions, deletions, and/or insertions as compared to the light chain variable region reference sequence. In some embodiments, in the context of amino acid substitutions, the substitutions comprise conservative amino acid substitutions. In particular, in some embodiments, the conservative substitutions are present on the framework regions (non-CDR regions: $FR_L1$, $FR_L2$, $FR_L3$ and $FR_L4$) of the light chain variable region reference sequence.

In some embodiments, the antibody with the defined level of amino acid sequence identity to the heavy chain variable region has one or more amino acid substitutions, deletions and/or insertions as compared to the VH reference sequence of SEQ ID NO:28, more particularly SEQ ID NO:29. In some embodiments, the antibody comprises 1, 2, 3, 4, 5 or more amino acid substitutions, deletions, and/or insertions as compared to the heavy chain variable region reference sequence. In some embodiments, in the context of amino acid substitutions, the substitutions comprise conservative amino acid substitutions. In particular, in some embodiments, the conservative substitutions are present on the framework regions (non-CDR regions: $FR_H1$, $FR_H2$, $FR_H3$ and $FR_H4$) of the heavy chain variable region reference sequence.

In some embodiments, the antibody with any of the specified antigen binding domains can comprise any suitable framework variable region sequence, provided the functional properties of the antigen binding domain in binding to sMICA and/or sMICB, or the alpha-3 domain thereof, are maintained. In some embodiments, the framework sequences are those of rodent variable light chain and heavy chain framework sequences, in particular mouse framework sequences. In some embodiments, the framework sequences of the antibody are those of a human heavy chain consensus framework sequence. Examples of VH consensus framework sequences include: human VH subgroup I consensus framework (SEQ ID NO:32); human VH subgroup II consensus framework (SEQ ID NO:33); human VH subgroup III consensus framework (SEQ ID NO:34); and human VH subgroup VII consensus framework (SEQ ID NO:35) (FIG. 8). In some embodiments, the framework sequences of the antibody comprise a human κ1 light chain consensus framework sequence. Examples of VL consensus framework sequences include: human VL kappa subgroup I consensus framework (SEQ ID NO:36); human VL kappa subgroup II consensus framework (SEQ ID NO:37); human VL kappa subgroup III consensus framework (SEQ ID NO:38); and human VL kappa subgroup IV consensus framework (SEQ ID NO:39) (FIG. 8).

In some embodiments, the antibody with any of the specified antigen binding domains can have a constant region on the light chain and/or the heavy chain of any origin. The constant region can be that of rodent, primate, or other mammals. In some embodiments, the constant region is of human origin. Accordingly, in some embodiments, the antibody with any of the specified antigen binding domains above can have a human constant region, for example, a human light chain constant region CL and/or a human heavy chain constant region. For example, the VL amino acid sequence of SEQ ID NO:24, more particularly SEQ ID NO:25, can have a human light chain constant region, and the VH amino acid sequence of SEQ ID NO:28, more particularly SEQ ID NO:29, can have a human heavy chain constant region. In some embodiments, the human light chain constant region CL comprises a human kappa or human lambda constant region. In some embodiments, the human heavy chain constant region comprises at least one or all of the following: a human CH1, human Hinge, human CH2 and human CH3 domain. In some embodiments, the heavy chain constant region comprises an Fc portion, where the Fc portion is a human $IgG_1$, $IgG_2$, $IgG_3$, $IgG_4$ or IgM isotype.

In some embodiments, the antibody comprises at least 1, 2, or 3 of the CDRs selected from: CDR L1 comprising an amino acid sequence RSSQSIVHSNGNTYLE (SEQ ID NO:40); CDR L2 comprising an amino acid sequence KVSNRFS (SEQ ID NO:41); CDR L3 comprising an amino acid sequence FQGSHVPFT (SEQ ID NO:42); and a human light chain constant region, particularly a human light chain constant region of human kappa or lambda light chains.

In some embodiments, the antibody comprises at least 1, 2, or 3 of the CDRs selected from: CDR H1 comprising an amino acid sequence NYLIE (SEQ ID NO:43); CDR H2 comprising an amino acid sequence LIYPGSGGTNYNEKFKG (SEQ ID NO:44); CDR H3 comprising an amino acid sequence IYYGNRDYGMDY (SEQ ID NO:45); and a human heavy chain constant region, in particular a human heavy chain constant region comprising at least one or all of: human CH1, human Hinge, human CH2 and human CH3 domain. In such embodiments, the antibody can comprise human framework sequences in the variable regions. In some embodiments, the heavy chain constant region comprises an Fc portion, where the Fc portion is a human $IgG_1$, $IgG_2$, $IgG_3$, $IgG_4$ or IgM isotype.

In some embodiments, the antibody comprises: (i) a VL region having at least 1, 2, or 3 of the CDRs selected from: CDR L1 comprising an amino acid sequence RSSQSIVHSNGNTYLE (SEQ ID NO:40); CDR L2 comprising an amino acid sequence KVSNRFS (SEQ ID NO:41); CDR L3 comprising an amino acid sequence FQGSHVPFT (SEQ ID NO:42); and a human light chain constant region, particularly a human light chain constant region of human kappa or lambda, and (ii) a VH region having at least 1,2 or 3 of the CDRs selected from: CDR H1 comprising an amino acid sequence NYLIE (SEQ ID NO:43); CDR H2 comprising an amino acid sequence LIYPGSGGTNYNEKFKG (SEQ ID NO:44); CDR H3 comprising an amino acid sequence IYYGNRDYGMDY (SEQ ID NO:45), and a human heavy chain constant region, in particular a human heavy chain constant region comprising at least one or all of: human CH1, human Hinge, human CH2 and human CH3 domain. In some embodiments, the heavy chain constant region comprises an Fc portion, where the Fc portion is a human $IgG_1$, $IgG_2$, $IgG_3$, $IgG_4$ or IgM isotype. In such embodiments, the antibody can comprise human framework sequences in the variable regions.

In some embodiments, the antibody comprises a light chain variable region VL comprising an amino acid sequence of SEQ ID NO:24, more particularly SEQ ID NO:25, and a human light chain constant (CL) region, in particular a human kappa or lambda constant region; a heavy chain variable region VH comprising an amino acid sequence of SEQ ID NO:28, more particularly SEQ ID NO:29, and a human heavy chain constant region, in particular a human heavy chain constant region comprising human CH1, human Hinge, human CH2 and human CH3 domain. In some embodiments, the heavy chain constant region comprises an Fc portion, where the Fc portion is a human $IgG_1$, $IgG_2$, $IgG_3$, $IgG_4$ or IgM isotype.

In some embodiments, the antibody comprises a multimeric antibody containing three or more antigen binding sites, for example an IgM isotype or a synthetically generated multimeric antibody. IgM antibodies generally have four, five or six units of bivalent binding units, i.e., two heavy chains and two light chains assembled into a tetramer, pentamer and/or hexamer. The IgM antibody may or may not have a J chain. Expression of IgM without a J chain forms predominantly hexamers while expression of IgM with J chains forms predominantly pentamers. The multimeric antibodies would promote efficient binding to sMICA and/or sMICB resulting from the higher number of antigen binding sites. In some embodiments, IgM antibodies can be obtained by isolating IgM antibodies from immunized animals, by isolating monoclonal antibody producing cell lines (e.g., hybridoma cell lines, etc.) expressing IgM isotype antibody, or transfection/transformation of appropriate cell lines (e.g., CHO, COS, 3T3, PC12, BHK, Vero, C6 glioma, and HeLa) with nucleic acids encoding an IgM antibody or IgM variable heavy and variable light chains, with or without J chains (see, e.g., Azuma et al., 2007, Clin Cancer Res. 13:2745-50; Mader et al., 2013, Advances in Biosci Biotech. 4:38-43; U.S. Pat. No. 7,709,615). In some embodiments, an initially isolated IgG antibody can be class switched to the IgM isotype by expression in appropriate cells lines. For example, Kunert et al., 2004, AIDS Res Hum Retroviruses, 20:755-62 and Wolbank et al., 2003, J Virol. 77:4095-103 describe switching of IgG monoclonal antibodies to IgM isotype. In some embodiments, multimeric antibodies can be generated using single chain antibodies or antibody fragments produced as multimeric antibodies (see, e.g., Power et al., 2003, Methods Mol Biol. 207:335-50; Gail et al., 1999, FEBS Lett. 453(1-2):164-8). The IgM or single chain multimeric antibodies can be purified by techniques known in the art, such as gel filtration chromatography, ion exchange chromatography (e.g., hydroxyapatite), and affinity chromatography (see, e.g., Valasek et al., 2011, BioProcess Int'l. 9(11):28-37; Gagnon et al., 2008, BioPharm Int'l. S26-S36). In some embodiments, the multimeric antibodies can comprise 50% or more hexamer, 60% or more pentamer, or particularly 80% or more pentamer or hexamer IgM molecule. In some embodiments, the IgM or multimeric antibody comprises an antibody binding domain described above, including the various combinations of the CDRs or variable regions of antibody 5C9.

In some embodiments, the antibody can be a fragment of the antibody of the present disclosure, including portions of the full length antibody, and includes the antigen binding or variable region. Exemplary antibody fragments include Fab, Fab', F(ab')2 and Fv fragments. Proteolytic digestion of an antibody with papain produces two identical antigen binding fragments, the Fab' fragment, each with a single antigen binding site. Proteolytic digestion with pepsin yields an F(ab')2 fragment that has two antigen binding fragments which are capable of cross-linking antigen, and a residual pFc' fragment. Other types of fragments can include diabodies, linear antibodies, single-chain antibodies, and multispecific antibodies formed from antibody fragments. The antibody fragments are functional in that they retain the desired binding properties, e.g., specific binding to the defined epitope in the alpha-3 domain of sMICA and/or sMICB but does not bind to the extracellular domain of MICA and/or MICB bound to a cell membrane.

In some embodiments, the antibodies can be labeled with a variety of labels, including reporter molecules and detectable labels, such as fluorophores, bioluminescent moieties, luminescent moieties, enzymes, radiolabels, and prosthetic groups. Exemplary enzymes include, among others, horseradish peroxidase, alkaline phosphatase, β-galactosidase, and acetylcholinesterase. Exemplary prosthetic groups include, among others, streptavidin/biotin and digoxigenin. Exemplary fluorophores include, among others, fluorescein, fluorescein isothiocyanate, rhodamine, dichlorotriazinylamine fluorescein, dansyl chloride, Texas Red and phycoerythrin. Exemplary luminescent label includes luminal. Exemplary bioluminescent labels include luciferase, luciferin, and aequorin. Exemplary radiolabels include, among others, $^{125}I$, $^{131}I$, $^{35}S$, $^{211}At$, $^{90}Y$, $^{186}Re$, $^{188}Re$, $^{14}C$, $^{225}Ac$, $^{212}Bi$, $^{227}Ac$, $^{194}Os$, $^{223}Ra$, $^{149}Tb$, and $^{3}H$.

In some embodiments, the antibody of the disclosure can be conjugated to an effector moiety. The effector moiety can be, among others, antineoplastic agents, drugs, toxins, biologically active proteins, other antibody or antibody fragments, synthetic or naturally occurring polymers, nucleic acids (e.g., DNA and RNA), chelated metals, and nanoparticles. For example, the antibody can be conjugated to an effector moiety, such as a cytotoxic agent, a radionuclide or drug moiety to modify a given biological response. The effector moiety can be a protein or polypeptide, such as, for example and without limitation, a toxin (e.g., abrin, ricin A, *Pseudomonas* exotoxin, or Diphtheria toxin), a thrombotic agent or an anti-angiogenic agent (e.g., angiostatin or endostatin), or a biological response modifier such as a cytokine or growth factor (e.g., interleukin-I (IL-I), interleukin-2 (IL-2), interleukin-6 (IL-6), granulocyte macrophage colony stimulating factor (GM-CSF), granulocyte colony stimulating factor (G-CSF), or nerve growth factor (NGF)).

In some embodiments, the effector moieties can be cytotoxins or cytotoxic agents. Exemplary cytotoxins and cytotoxic agents include taxol, chlorambucil, cytochalasin B, gramicidin D, ethidium bromide, emetine, mitomycin, etoposide, teniposide, vincristine, vinblastine, colchicine, doxorubicin, daunorubicin, dihydroxyanthracenedione, mitoxantrone, mithramycin, actinomycin D, melphalan, puromycin, and analogs or homologs thereof.

Techniques for conjugating such effector moieties to antibodies are well known in the art (see, e.g., Hellstrom et al., Controlled Drug Delivery, 2nd Ed., Robinson et al., eds., pp. 623-53 (1987); Thorpe et al., 1982, Immunol Rev. 62:119-58; Dubowchik et al., 1999, Pharmacol Ther. 83:67-123; and "Antibody-Drug Conjugates and Immunotoxins: From Pre-Clinical Development to Therapeutic Applications," in Cancer Drug Discovery and Development, Gail Lewis Phillips, ed., Springer Publisher (2012)).

In some embodiments, the antibodies of the present disclosure can be attached to polyethylene glycol (PEG) moieties. In some embodiments, the antibody is an antibody fragment. The PEG moieties can be attached through any available amino acid side-chain or terminal amino acid functional group located in the antibody or antibody fragment, for example any free amino, imino, thiol, hydroxyl or carboxyl group. Such amino acids can occur naturally in the antibody or antibody fragment or can be engineered into the antibody or fragment using recombinant DNA methods. Multiple sites can be used to attach two or more PEG molecules. PEG moieties can be covalently linked through a thiol group of at least one cysteine residue located in the antibody or fragment. Where a thiol group is used as the point of attachment, appropriately activated effector moieties (for example, thiol selective derivatives such as maleimides and cysteine derivatives) can be used (see, e.g., Poly(ethyleneglycol) Chemistry and Biological Applications, Milton Harris and S. Zalipsky, eds., American Chemical Society, Washington D.C. (1997); Bioconjugation Protein Coupling Techniques for the Biomedical Sciences, M. Aslam and A. Dent, eds., Grove Publishers, New York, 1998; and Chapman, 2002, Adv Drug Deliv Rev. 54:531-45).

In another aspect, provided herein are polynucleotides which encode the antibodies or antigen binding regions of the present disclosure. In particular, the polynucleotides are isolated polynucleotides. The polynucleotides may be operatively linked to one or more heterologous control sequences that control gene expression to create a recombinant polynucleotide capable of expressing the polypeptide of interest. Expression constructs containing a heterologous polynucleotide encoding the relevant polypeptide or protein can be introduced into appropriate host cells to express the corresponding polypeptide.

In some embodiments, the polynucleotide encodes a light chain variable region VL having at least 80%, 85%, 90%, 91%, 92%, 93%, 94%, 95%, 96%, 97%, 98%, 99% or greater sequence identity to the amino acid sequence of SEQ ID NO:24, more particularly SEQ ID NO:25. In some embodiments, the polynucleotide encodes a heavy chain variable region VH having at least 80%, 85%, 90%, 91%, 92%, 93%, 94%, 95%, 96%, 97%, 98%, 99% or greater sequence identity to the amino acid sequence of SEQ ID NO:28, more particularly SEQ ID NO:29.

In some embodiments, the polynucleotide encodes one or more CDRs selected from: CDR L1 comprising an amino acid sequence RSSQSIVHSNGNTYLE (SEQ ID NO:40); CDR L2 comprising an amino acid sequence KVSNRFS (SEQ ID NO:41); CDR L3 comprising an amino acid sequence FQGSHVPFT (SEQ ID NO:42); CDR H1 comprising an amino acid sequence NYLIE (SEQ ID NO:43); CDR H2 comprising an amino acid sequence LIYPGSGGTNYNEKFKG (SEQ ID NO:44); and CDR H3 comprising an amino acid sequence IYYGNRDYGMDY (SEQ ID NO:45).

In some embodiments, the polynucleotide encodes at least 1, 2, or 3 of the CDRs selected from: CDR L1 comprising an amino acid sequence RSSQSIVHSNGNTYLE (SEQ ID NO:40); CDR L2 comprising an amino acid sequence KVSNRFS (SEQ ID NO:41); and CDR L3 comprising an amino acid sequence FQGSHVPFT (SEQ ID NO:42). In some embodiments, the polynucleotide encodes at least 1, 2, or 3 of the CDRs selected from: CDR H1 comprising an amino acid sequence NYLIE (SEQ ID NO:43); CDR H2 comprising an amino acid sequence LIYPGSGGTNYNEKFKG (SEQ ID NO:44); and CDR H3 comprising an amino acid sequence IYYGNRDYGMDY (SEQ ID NO:45).

In some embodiments, the polynucleotide encodes at least 1, 2, 3, 4, 5 or all 6 of the CDRs in the light chain variable region of amino acid sequence of SEQ ID NO:25 and the heavy chain variable region of amino acid sequence of SEQ ID NO:29. In some embodiments, the polynucleotide encodes at least 1, 2, 3, 4, 5 or all 6 of the CDRs selected from: CDR L1 comprising an amino acid sequence RSSQSIVHSNGNTYLE (SEQ ID NO:40); CDR L2 comprising an amino acid sequence KVSNRFS (SEQ ID NO:41); CDR L3 comprising an amino acid sequence FQGSHVPFT (SEQ ID NO:42); CDR H1 comprising an amino acid sequence NYLIE (SEQ ID NO:43); CDR H2 comprising an amino acid sequence LIYPGSGGTNYNEKFKG (SEQ ID NO:44); and CDR H3 comprising an amino acid sequence IYYGNRDYGMDY (SEQ ID NO:45).

In some embodiments, the polynucleotide encodes a polypeptide comprising at least 1, 2, or 3 of the CDRs selected from: CDR L1 comprising an amino acid sequence RSSQSIVHSNGNTYLE (SEQ ID NO:40); CDR L2 comprising an amino acid sequence KVSNRFS (SEQ ID NO:41); CDR L3 comprising an amino acid sequence FQGSHVPFT (SEQ ID NO:42), and a human light chain constant region, particularly a human light chain constant region of human kappa or lambda light chains. In some embodiments, the polynucleotide encodes a polypeptide comprising at least 1, 2, or 3 of the CDRs selected from: CDR H1 comprising an amino acid sequence NYLIE (SEQ ID NO:43); CDR H2 comprising an amino acid sequence LIYPGSGGTNYNEKFKG (SEQ ID NO:44); CDR H3 comprising an amino acid sequence IYYGNRDYGMDY (SEQ ID NO:45), and a human heavy chain constant region, in particular a human heavy chain constant region comprising at least one or all of: human CH1, human Hinge, human CH2 and human CH3 domain. In some embodiments, the encoded heavy chain constant region comprises an Fc portion, where the Fc portion is a human $IgG_1$, $IgG_2$, $IgG_3$, $IgG_4$ or IgM isotype. In some embodiments, the encoded antibody can comprise human framework sequences in the variable regions.

In some embodiments, the polynucleotide encodes a polypeptide comprising: (i) a VL region having at least 1, 2, or 3, of the CDRs selected from: CDR L1 comprising an amino acid sequence RSSQSIVHSNGNTYLE (SEQ ID NO:40); CDR L2 comprising an amino acid sequence KVSNRFS (SEQ ID NO:41); CDR L3 comprising an amino acid sequence FQGSHVPFT (SEQ ID NO:42); and a human light chain constant region, particularly a human light chain constant region of human kappa or lambda light chains, and (ii) a VH region having at least 1,2 or 3 of the CDRs selected from: CDR H1 comprising an amino acid sequence NYLIE (SEQ ID NO:43); CDR H2 comprising an amino acid sequence LIYPGSGGTNYNEKFKG (SEQ ID NO:44); CDR H3 comprising an amino acid sequence IYYGNRDYGMDY (SEQ ID NO:45), and a human heavy chain constant region, in particular a human heavy chain constant region comprising at least one or all of: human CH1, human Hinge, human CH2 and human CH3 domain. In some embodiments, the encoded heavy chain constant region comprises an Fc portion, where the Fc portion is a human $IgG_1$, $IgG_2$, $IgG_3$, $IgG_4$ or IgM isotype. In such embodiments, the encoded antibody can comprise human framework sequences in the variable regions.

In some embodiments, the polynucleotide encodes a polypeptide comprising: (i) a light chain variable region VL comprising an amino acid sequence of SEQ ID NO:24, more particularly SEQ ID NO:25, and a human light chain constant (CL) region, in particular a human kappa or lambda constant region; and (ii) a heavy chain variable region VH comprising an amino acid sequence of SEQ ID NO:28, more particularly SEQ ID NO:29, and a human heavy chain constant region, in particular a human heavy chain constant region comprising human CH1, human Hinge, human CH2 and human CH3 domain. In some embodiments, the encoded heavy chain constant region comprises an Fc portion, where the Fc portion is a human $IgG_1$, $IgG_2$, $IgG_3$, $IgG_4$ or IgM isotype.

As will be apparent to the skilled artisan, the knowledge of a protein sequence provides a description of all the polynucleotides capable of encoding the subject protein sequence because of the knowledge of the all possible codons corresponding to the various amino acids. An extremely large number of nucleic acids encoding the forgoing polypeptides can be made by selecting combinations based on the possible codon choices, and all such variations are to be considered specifically disclosed for the polypeptide described herein.

In some embodiments, the polynucleotide has at least about 80%, 85%, 86%, 87%, 88%, 89%, 90%, 91%, 92%, 93%, 94%, 95%, 96%, 97%, 98%, or 99% or more sequence identity at the nucleotide level to: (a) a reference polynucleotide sequence of SEQ ID NO:26, and encodes the polypeptide of SEQ ID NO:24. In some embodiments, the polynucleotide has at least about 80%, 85%, 86%, 87%, 88%, 89%, 90%, 91%, 92%, 93%, 94%, 95%, 96%, 97%, 98%, or 99% or more sequence identity at the nucleotide level to: (a) a reference polynucleotide sequence of SEQ ID NO:30, and encodes the polypeptide of SEQ ID NO:28.

In some embodiments, the polynucleotide has at least about 80%, 85%, 86%, 87%, 88%, 89%, 90%, 91%, 92%, 93%, 94%, 95%, 96%, 97%, 98%, or 99% or more sequence identity at the nucleotide level to: (a) a reference polynucleotide sequence of SEQ ID NO:27, and encodes the polypeptide of SEQ ID NO:25. In some embodiments, the polynucleotide has at least about 80%, 85%, 86%, 87%, 88%, 89%, 90%, 91%, 92%, 93%, 94%, 95%, 96%, 97%, 98%, or 99% or more sequence identity at the nucleotide level to: (a) a reference polynucleotide sequence of SEQ ID NO:31, and encodes the polypeptide of SEQ ID NO:29.

In some embodiments, the polynucleotides herein may be manipulated in a variety of ways to provide for expression of the encoded polypeptide. In some embodiments, the polynucleotide is operably linked to control sequences, including among others, origins of replication, transcription promoters, leader sequences, transcription enhancers, ribosome binding or entry sites, termination sequences, polyadenylation sequences, and selectable marker sequences for expression of the polynucleotide and/or corresponding polypeptide. Where selectable marker genes are used, suitable marker genes include, without limitation, drug resistance markers (e.g., G418, hygromycin, or methotrexate, etc.), fluorescent proteins (e.g., green fluorescent protein and variants thereof, luciferase, etc.), and detectable enzymes (e.g., beta-galactosidase, glucouronidase). Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., Molecular Cloning: A Laboratory Manual, 3rd Ed., Cold Spring Harbor Laboratory Press, New York (2001); and Current Protocols in Molecular Biology, Ausubel. F. ed., Greene Pub. Associates (1998), updates to 2013.

In some embodiments, the nucleic acid encoding the VL region can be made into a full length light chain gene by operatively linking the VL encoding nucleic acid to another nucleic acid encoding the light chain constant region CL. In some embodiments, the light chain constant region can be a kappa or lambda, particularly human kappa or lambda light chain constant region. As described herein, the sequences of the light chain constant region are known in the art (see, e.g., Kabat et al., 1991, "Sequences of Proteins of Immunological Interest, Fifth Edition, NIH Publication No. 91-3242).

In some embodiments, nucleic acid encoding the VH region can be made into a full length heavy chain gene by operatively linking the VH encoding nucleic acid to another nucleic acid encoding the heavy chain constant regions, e.g., CH1, Hinge, CH2 and/or CH3. The sequences of the light chain constant region are known in the art (see, e.g., Kabat et al., 1991, "Sequences of Proteins of Immunological Interest, Fifth Edition, NIH Publication No. 91-3242). In some embodiments, the encoded constant region is an IgA (e.g., IgA$_1$ or IgA$_2$); IgD, IgE, IgG (e.g., IgG$_1$, IgG$_2$, IgG$_3$, IgG$_4$) or IgM, particularly IgG$_1$ or IgG$_2$, more particularly IgG$_2$. For generating a Fab fragment heavy chain gene, the nucleic acid encoding VH region can be operatively linked to another nucleic acid encoding the heavy chain CH1 constant region. For creating a scFv gene, the VH and VL encoding nucleic acids can be operatively linked together through another nucleic acid encoding a flexible peptide linker, for example encoding the amino acid sequence (Gly$_4$-Ser)$_3$, such that the VL and VH region joined by the flexible linker is expressed as a continuous single chain protein.

In some embodiments, the polynucleotides can be part of an expression vector, where the vector and polynucleotide includes one or more operably linked control sequences for controlling expression of the polynucleotide and/or expression of the encoded polypeptide. Thus, in some embodiments, an expression vector comprises a polynucleotide disclosed herein operatively linked to one or more control sequences for expression of the encoded polypeptide, for example the polypeptides comprising SEQ ID NO:25 and/or SEQ ID NO:29, or 1, 2, 3, 4, 5 or all 6 of the CDRs in the light chain variable region of amino acid sequence of SEQ ID NO:25 and the heavy chain variable region of amino acid sequence of SEQ ID NO:29. In some embodiments, the expression vector comprises a polynucleotide encoding at least 1, 2, 3, 4, 5 or all 6 of the CDRs selected from: CDR L1 comprising an amino acid sequence RSSQSIVHSNGNTYLE (SEQ ID NO:40); CDR L2 comprising an amino acid sequence KVSNRFS (SEQ ID NO:41); CDR L3 comprising an amino acid sequence FQGSHVPFT (SEQ ID NO:42); CDR H1 comprising an amino acid sequence NYLIE (SEQ ID NO:43); CDR H2 comprising an amino acid sequence LIYPGSGGTNYNEKFKG (SEQ ID NO:44); and CDR H3 comprising an amino acid sequence IYYGNRDYGMDY (SEQ ID NO:45). The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids. Exemplary expression vectors include, among others, vectors based on T7 or T7lac promoters (pACY: Novagen; pET); vectors based on Baculovirus promoters (e.g., pBAC); vectors based on Ef1-α and HTLV promoters (e.g., pFUSE2; Invitrogen, CA, USA); vectors based on CMV enhancer and human ferritin light chain gene promoters (e.g., pFUSE: Invitrogen, CA, USA); vectors based on CMV promoters (e.g., pFLAG: Sigma, USA); and vectors based on dihydrofolate reductase promoters (e.g., pEASE: Amgen, USA). Various vectors can be used for transient or stable expression of the polypeptides of interest. In some embodiments, the antibody light chain gene and the antibody heavy chain gene can be in separate vectors or both genes can be in the same expression vector. In some embodiments, the vectors for expression of the antibody can already contain constant chain sequences. For example, the vector can contain sequences for the light chain constant region such that inserting the variable light chain region into the vector in a manner to operatively link the light chain variable region to the variable light chain constant region to create an expression vector capable of expressing the light chain of the antibody. The vector can also include a signal peptide to facilitate secretion of the antibody chain from a host cell. Similarly, a vector can contain sequences for the heavy chain constant region such that inserting the variable heavy chain region into the vector in a manner to operatively link the heavy chain variable region to the heavy chain constant region creates an expression vector capable of expressing the heavy chain of the antibody.

In another aspect, the polynucleotide encoding a polypeptide is operatively linked to one or more control sequences for expression of the polypeptide in a host cell. Thus in some embodiments, a host cell comprises a polynucleotide or an expression vector described herein, for example a an expression vector or polynucleotide encoding the polypeptides comprising SEQ ID NO:25 and/or SEQ ID NO:29, or 1, 2, 3, 4, 5 or all 6 of the CDRs in the light chain variable region of amino acid sequence of SEQ ID NO:25 and the heavy chain variable region of amino acid sequence of SEQ ID NO:29. In some embodiments, the host cell comprises an expression vector or a polynucleotide encoding at least 1, 2, 3, 4, 5 or all 6 of the CDRs selected from: CDR L1 comprising an amino acid sequence RSSQSIVHSNGNTYLE (SEQ ID NO:40); CDR L2 comprising an amino acid sequence KVSNRFS (SEQ ID NO:41); CDR L3 comprising an amino acid sequence FQGSHVPFT (SEQ ID NO:42); CDR H1 comprising an amino acid sequence NYLIE (SEQ ID NO:43); CDR H2 comprising an amino acid sequence LIYPGSGGTNYNEKFKG (SEQ ID NO:44); and CDR H3 comprising an amino acid sequence IYYGNRDYGMDY (SEQ ID NO:45). Host cells for use in expressing the polypeptides are well known in the art and include, but are not limited to, bacterial cells, such as *E. coli*, yeast cells; insect cells such as *Drosophila* S2 and *Spodoptera* Sf9 cells; animal cells such as Chinese Hamster Ovary (CHO), African Green Monkey kidney (COS), baby hamster kidney (BHK), mouse myelomas (e.g., NS0 and Sp2/0), and human embryo kidney (HEK); and plant cells. Appropriate culture mediums and growth conditions for the above-described host cells are well known in the art. In some embodiments, the host cells and the expression vectors are used to express the polypeptides of interest. In some embodiments, the host cell comprises a nucleic acid encoding any of the antibodies of the disclosure, or any of the polynucleotides provided herein.

In some embodiments, the host cells comprising the expression vectors and polynucleotides are cultured in suitable media and under culture conditions appropriate for expression of the encoded polypeptide, for example the polypeptides comprising SEQ ID NO:25 and/or SEQ ID NO:29, or 1, 2, 3, 4, 5 or all 6 of the CDRs in the light chain variable region of amino acid sequence of SEQ ID NO:25 and the heavy chain variable region of amino acid sequence of SEQ ID NO:29. In some embodiments, the host cells are cultured in suitable media to express a polypeptide having at least 1, 2, 3, 4, 5 or all 6 of the CDRs selected from: CDR L1 comprising an amino acid sequence RSSQSIVHSNGNTYLE (SEQ ID NO:40); CDR L2 comprising an amino acid sequence KVSNRFS (SEQ ID NO:41); CDR L3 comprising an amino acid sequence FQGSHVPFT (SEQ ID NO:42); CDR H1 comprising an amino acid sequence NYLIE (SEQ ID NO:43); CDR H2 comprising an amino acid sequence LIYPGSGGTNYNEKFKG (SEQ ID NO:44); and CDR H3 comprising an amino acid sequence IYYGNRDYGMDY (SEQ ID NO:45). In some embodiments, an in vitro expression system can be used with the expression vectors to express the polypeptide. In vitro expression systems include those based on *E. coli*, rabbit reticulocyte, wheat germ, insect cells, or human cells. Whether expressed in a host cell or in vitro, the expressed polypeptides can be isolated or purified, as further described herein.

In some embodiments, where recombinant expression vectors encoding antibody genes are introduced into host cells, the antibody is produced by culturing the host cells under suitable conditions for a period of time sufficient to allow for expression of the antibody in the host cell or secretion of the antibody into the culture medium. The antibody can be recovered from the host cells and/or culture medium by isolation and/or purification methods known in the art.

In another aspect, the antibodies of the present disclosure can be prepared by various techniques available to the skilled artisan. The preparation of polyclonal antibodies can employ conventional procedures well-known to those skilled in the art, for example, Green et al., "Production of Polyclonal Antisera," in: Immunochemical Protocols, Manson, ed., Humana Press (1992); Coligan et al., "Production of Polyclonal Antisera in Rabbits, Rats Mice and Hamsters," in: Current Protocols in Immunology, John Wiley & Sons, Inc. (1992), which are hereby incorporated herein by reference.

The preparation of monoclonal antibodies can also use conventional techniques known in the art, for example, Kohler and Milstein, 1975, Nature 256 (5517):495-7; Coligan et al., supra, sections 2.5.1-2.6.7; Current Protocols in Immunology, John Wiley & Sons, Inc. (1992); and Antibodies: A Laboratory Manual, Harlow and Lane, eds., Cold Spring Harbor Press, New York (1988); Monoclonal Antibodies: Methods and Protocols in Methods Mol Biol., Vol. 378, Albitar M., ed., Humana Press (2007), which are hereby incorporated herein by reference. Monoclonal antibodies are most frequently generated in mice by immunization with an antigen and subsequent isolation of B-cells that make antibodies. The B-cells are then immortalized by fusion to another, stable cell type of the same species of the B-cell to create a "hybridoma". An individual B-cell makes one specific antibody (i.e., clonally monospecific) which is defined by its primary amino acid sequence and its underlying gene sequence. Also, the terms "heterohybridoma" and "heteromyeloma" refer to lymphocyte cell lines immortalized by fusion of lymphocytes and myelomas, respectively, from two different species. Monoclonal antibodies can be isolated and purified from hybridoma cultures by a variety of established techniques. Such isolation techniques include affinity chromatography with Protein-A SEPHAROSE, size-exclusion chromatography, and ion-exchange chromatography (see, e.g., Coligan et, al., supra, sections 2.7.1-2.7.12 and sections 2.9.1-2.9.3; Barnes, et al., Purification of Immunoglobulin G (IgG), in Methods Mol. Biol., Vol. 10, pages 79-104, Humana Press (1992)). An exemplary method for preparing antibodies is described in the Examples.

Generally, the generation of polyclonal or monoclonal antibodies can be achieved using immunogens derived from DNA, peptides, or proteins. Hybridomas are generated by immunizing an animal, which can be for example, a mouse or rabbit, or any animal that will give a suitable antibody response. In some embodiments, immunization is performed by introducing into the animal an antigen-encoding nucleic acid, or a protein antigen, such as the extracellular domain of MICA/MICB or a fragment thereof (e.g., alpha-3 domain), or a nucleic acid encoding the extracellular domain of MICA/MICB or a fragment thereof (e.g., alpha-3 domain). In some embodiments, the peptide containing the defined epitope can be conjugated to a carrier such as keyhole limpet hemocyanin, which may elicit a stronger antibody response than the peptide alone. Such variations and other immunization schemes are available to the skilled artisan. In some embodiments, following immunization, polyclonal antibodies having the defined characteristics can be isolated, e.g., by absorbing an antibody preparation with membrane-bound MIC protein and using the unabsorbed antibodies for affinity purification with an extracellular domain of MIC, such as sMICA and/or sMICB. Monoclonal antibodies produced by hybridomas can be screened for binding to the defined epitope, binding to sMIC and membrane-bound MIC, and other characteristics as described herein. The hybridoma cells producing the desired antibody can be further selected and used for production of the monoclonal antibody.

Chimeric antibodies, which are antibodies having variable sequences derived from a non-human immunoglobulin, such as rat or mouse antibody, and in some embodiments, human immunoglobulin constant regions, typically chosen from a human immunoglobulin template, can also be prepared by conventional techniques. One method is to clone the non-human genes encoding the variable regions and the human genes encoding the constant regions and combine them using recombinant techniques to form a chimeric gene. Expression in appropriate cells produces an mRNA encoding the chimeric protein. An alternative process is to use homologous recombination, where a rodent or mouse hybridoma cell line is transfected with a human constant region gene flanked by sequences homologous to the corresponding rodent immunoglobulin constant region gene. At a low frequency the transfected DNA will recombine with the rodent gene resulting in the insertion of the human immunoglobulin constant region gene sequence. Various methods for producing chimeric antibodies are described in, for example, Morrison et al., 1984, Proc Natl Acad Sci USA. 81:6851-5; Morrison et al., 1985, Science 229(4719):1202-7; Neuberger et al., 1985, Nature 314:268-71; Oi et al., 1986, BioTechniques 4:214-21; Gillies et al., 1985, Immunol. Methods 125:191-202; U.S. Pat. Nos. 5,807,715; 4,816,567; and 4,816,397; all of which are incorporated herein by reference in their entireties.

In some embodiments, the antibodies herein can be prepared as humanized antibodies, which are chimeric immunoglobulins, immunoglobulin chains or fragments thereof (such as Fv, Fab, Fab', F(ab')2 or other target-binding sub domains of antibodies) which contain minimal sequences derived from non-human immunoglobulin. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin sequence. The humanized antibody can also comprise at least a portion or all of an immunoglobulin constant region, typically that of a human immunoglobulin consensus sequence. Methods of antibody humanization are described in, for example, Riechmann et al., 1988, Nature 332:323-7; U.S. Pat. Nos. 5,225,539; 5,530,101; 5,585,089; 5,565,332; 5,693,761; 5,693,762; and 6,180,370; PCT publication WO 91/09967; Padlan, 1991, Mol Immunol. 28:489-98; Studnicka et al., 1994, Prot Eng. 7:805-14; and Roguska et al., 1994, Proc Natl Acad Sci USA. 91:969-73; all of which are hereby incorporated herein by reference in their entireties.

Fully human antibodies can be generated using transgenic or trans-chromosomic animals carrying parts of the human immune system rather than the host animal system. These transgenic and trans-chromosomic animals include mice referred to as HuMAb mice and KM mice. The HuMAb Mouse™ (Medarex, Inc.) contains human immunoglobulin gene miniloci that encode un-rearranged human heavy (mu and gamma) and kappa light chain immunoglobulin sequences, together with targeted mutations that inactivate the endogenous mu and kappa chain loci (see, e.g., Lonberg et al., 1994, Nature 368(6474):856-9). Accordingly, the mice exhibit reduced expression of mouse IgM or kappa, and in response to immunization, the introduced human heavy and light chain transgenes undergo class switching and somatic mutation to generate high affinity human IgG kappa monoclonal antibodies (Lonberg, N., 1994, Handbook of Experimental Pharmacology 113:49-101; Lonberg, N. and Huszar, D., 1995, Intern Rev Immunol. 13:65-93; and Harding, F. and Lonberg, N., 1995, Ann NY Acad Sci. 764:536-46). The preparation and use of HuMAb mice, and the genomic modifications carried by such mice, are further described in Tuaillon et al., 1994, J Immunol. 152:2912-20; Taylor et al., 1994, International Immunology 6:579-91; Fishwild et al., 1996, Nature Biotech. 14:845-51; U.S. Pat. Nos. 5,545,806; 5,569,825; 5,625,126; 5,633,425; 5,789,650; 5,877,397; 5,661,016; 5,814,318; 5,874,299; 5,770,429; 5,545,807; and PCT publications WO 92103918, WO 93/12227, WO 94/25585, WO 97113852, WO 98/24884; WO 99/45962; and WO 01/14424; the contents of all of which are hereby specifically incorporated herein by reference in their entirety. An alternative transgenic system referred to as the Xenomouse™ (Abgenix, Inc.) can be used, which are described in Green, L L., 1999, J Immunol Methods, 231 (1-2):11-23; U.S. Pat. Nos. 5,939,598; 6,075,181; 6,114, 598; 6,150,584 and 6,162,963, all of which are incorporated herein by reference.

In some embodiments, cells producing human antibodies which bind to the specified epitopes and having the characteristics described herein can be prepared using a mouse that carries human immunoglobulin sequences on transgenes and trans-chromosomes, such as a mouse that carries a human heavy chain transgene and a human light chain trans-chromosome, as described in WO 02/043478. In some embodiments, a rabbit system expressing human immunoglobulin genes can be used to generate fully human antibodies (Rader et al., 2000, J Biol Chem. 275(18):13668-76).

In other embodiments, fully human monoclonal antibodies can be prepared using phage display methods for screening libraries of human immunoglobulin genes. Such phage display methods for isolating human antibodies are established in the art, and are described in, for example, Human Monoclonal Antibodies: Methods and Protocols, Methods Mol Biol., Vol. 1060, Steinitz, M., ed., Humana Press (2013); Marks and Bradbury, 2004, Methods Mol Biol., 248:161-76; Pansri et al., BMC Biotech., 9:6-22; Rader, C., 2012, Methods Mol Biol., 901:53-79; U.S. Pat. Nos. 5,223, 409; 5,403,484; 5,571,698; 5,427,908; 5,580,717; 5,969, 108; 6,172,197; 5,885,793; 6,521,404; 6,544,731; 6,555, 313; 6,582,915 and 6,593,081.

Single chain antibodies, which are fusion proteins of the variable heavy chains and variable light chains of immunoglobulins, can be obtained by phage display methods, where the antigen binding domain is expressed as a single polypeptide and screened for specific binding activity. Alternatively, the single chain antibody can be prepared by cloning the nucleic acids encoding the heavy and light chains from a cell, typically from a hybridoma cell line expressing a desired antibody. Generally, a linker peptide, typically from 10 to 25 amino acids in length, is used to link the heavy and light chains. The linker can be glycine, serine, and/or threonine rich to impart flexibility and solubility to the single chain antibody. Specific methods for generating single chain antibodies are described in, for example, Loffler et al., 2000, Blood 95(6):2098-103; Worn and Pluckthun, 2001, J Mol Biol. 305, 989-1010; Pluckthun, In The Pharmacology of Monoclonal Antibodies, Vol. 113, pp. 269-315, Rosenburg and Moore, eds., Springer-Verlag, New York (1994); U.S. Pat. Nos. 5,840,301; 5,844,093; and 5,892,020; all of which are incorporated herein by reference. In some embodiments, the single chain antibody comprises the CDRs in the variable light chain region comprising the amino acid sequence of SEQ ID NO:25. In some embodiments, the single chain antibody comprises the CDRs in the variable heavy chain region comprising the amino acid sequence of SEQ ID NO:29. In some embodiments, the single chain antibody comprises at least 1, 2, 3, 4, 5 or all 6 of the CDRs selected from: CDR L1 comprising an amino acid sequence RSSQSIVHSNGNTYLE (SEQ ID NO:40); CDR L2 comprising an amino acid sequence KVSNRFS (SEQ ID NO:41); CDR L3 comprising an amino acid sequence FQGSHVPFT (SEQ ID NO:42); CDR H1 comprising an amino acid sequence NYLIE (SEQ ID NO:43); CDR H2 comprising an amino acid sequence LIYPGSGGTNYNEKFKG (SEQ ID NO:44); and CDR H3 comprising an amino acid sequence IYYGNRDYGMDY (SEQ ID NO:45). In some embodiments, the single chain antibody comprises the variable light chain region comprising the amino acid sequence of SEQ ID NO:24, more particularly SEQ ID NO:25, and the variable heavy chain region comprising the amino acid sequence of SEQ ID NO:28, more particularly SEQ ID NO:29.

Making antibody fragments are also known in the art (see, e.g., Antibodies: A Laboratory Manual, Harlow and Lane, eds., Cold Spring Harbor Laboratory, New York (1988), incorporated herein by reference). Antibody fragments can be prepared by proteolytic digestion of the antibody or by expression in E. coli. of nucleic acids encoding the fragment. Antibody fragments can be obtained by pepsin or papain digestion of whole antibodies. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. In some embodiments, the antibody fragments can be prepared by recombinant techniques using polynucleotides encoding the antibody fragment.

In the embodiments for preparing antibodies of the disclosure, standard techniques may be used for recombinant DNA, oligonucleotide synthesis, tissue culture, and transfection (e.g., electroporation, lipofection, etc.). Enzymatic reactions and purification techniques may be performed according to manufacturer's specifications or as commonly accomplished in the art or as described herein. The foregoing techniques and procedures may be generally performed according to conventional methods available to the skilled artisan, such as described in various general and more specific references that are cited and discussed throughout the present specification (see, e.g. Sambrook and Russell, Molecular Cloning: A Laboratory Manual, 3rd Ed., Vol. 1-3, Cold Spring Harbor Laboratory Press, Cold Spring Harbor, N.Y. (2001); Antibodies: A Laboratory Manual, Greenfield, E. A., ed., Cold Spring Harbor Laboratory Press, New York (2012); and Current Protocols in Immunology, Coligan et al., eds., Wiley (1999), updates to 2013).

Conditions suitable for screening for the desired antibodies can use conditions in conventional screening procedures, for example, incubation of cells or polypeptides with the antibodies in aqueous buffered solutions followed by several washings. In some embodiments, a peptide containing the specified epitopes or MIC protein expressing cells can be immobilized on a solid surface, such as a membrane or plate, which is then contacted with the candidate antibodies. Non-specifically bound antibodies can be washed away with solutions containing non-specific competing agent, such as a suitable blocking agent. Exemplary contacting conditions may comprise incubation on ice or at 4° C. for 30 minutes to 4 hours. Alternatively, carrying out the contacting step at room temperature or 37° C. is possible and may be preferable in some cases. In addition, appropriate reagents such as blocking agents can be used to reduce non-specific binding, for example, bovine serum albumin, non-ionic detergents (e.g., NP40, TRITON X100, TWEEN 20, etc.), or other suitable blocking agent (e.g., non-fat milk). It will be appreciated that the contacting conditions can be varied and adapted by a skilled person depending on the aim of the screening method.

In some embodiments, the specific binding of a candidate antibody to the peptide containing the defined epitope can be determined by surface plasmon resonance (e.g., Biacore system) or Bio-Layer Interferometry (BLI). For surface plasmon resonance, antibodies can be immobilized on sensor chips and the chip exposed to peptides containing a defined epitope. The binding properties of the antibody to the peptide can be measured directly by the change in the local index of refraction upon interaction of the peptide with the antibody. Alternatively, the peptide can be bound to a sensor chip and the chip exposed to the candidate antibody (see, e.g., Rich, R. L. and Myszka, D. G., 2007, Anal Biochem. 361(1):1-6; and Pope et al., 2009, J Immunol Meth. 341(1-2):86-96; incorporated by reference herein). For BLI, the peptide antigen (or antibody) is bound to a biosensor (e.g., fiber optic probe), and the biosensor contacted with a solution containing the antibody (or peptide antigen). The biosensor tip is illuminated with white light, and the changes in interference pattern measured to detect binding. In some embodiments, one or more of other known methods, such as ELISA, FACS, or Western blotting can be used in addition to surface plasmon resonance or BLI to determine appropriate antibody binding potentials and antigenic site-specificities of the antibodies.

In some embodiments, the isolated antibody can be further purified as measurable by one or more of the following: (1) weight of protein as determined using the Lowry method; (2) to a degree sufficient to obtain at least 15 residues of N-terminal or internal amino acid sequence by use of an amino acid sequencer; and (3) to homogeneity by SDS-PAGE or CE-SDS under reducing or nonreducing conditions. Various techniques can be used for purifying the antibody, including by way of example and not limitation, chromatography (e.g., affinity chromatography such as with Protein A, peptide epitope, etc.; ion exchange chromatography, such as on cation and/or anion exchange medium; molecular sieve chromatograph; hydrophobic chromatography; etc.), high performance liquid chromatography, differential solubility, and the like (see, e.g., Fisher, Laboratory Techniques, In Biochemistry And Molecular Biology, Work and Burdon, eds., Elsevier (1980); Antibodies: A Laboratory Manual, Greenfield, E. A., ed., Cold Spring Harbor Laboratory Press, New York (2012)). The purified antibody can be 85% or greater, 90% or greater, 95% or greater, or at least 99% by weight as determined by the foregoing methods.

6.3 Pharmaceutical Compositions

In some embodiments, the antibody of the disclosure can be prepared as a pharmaceutical composition for treating a disease or disorder associated with elevated levels of a MIC protein, as further described below. Accordingly, in some embodiments, provided are pharmaceutical compositions comprising an isolated antibody, including a combination of two or more antibodies, that bind specifically to the specified epitope of sMIC protein, e.g., sMICA and/or sMICB protein; and a pharmaceutically acceptable carrier, excipient or vehicle that are compatible with the antibody preparations. In some embodiments, the pharmaceutical antibody composition can be prepared for administration by a variety of routes, such as intravenously, intramuscularly, intraperitoneally, transdermally, subcutaneously, intranasally, intrathecally, topically or orally. In some embodiments, therapeutic formulations of the antibodies can be prepared for storage as lyophilized formulations or as aqueous solutions by mixing the antibody having the desired degree of purity with optional pharmaceutically acceptable excipients, vehicles, or stabilizers typically employed in the art, all of which are referred to herein as "carriers", including, for example, buffering agents, stabilizing agents, preservatives, isotonicifiers, non-ionic detergents, antioxidants, and other miscellaneous additives (see, e.g., Remington: The Science and Practice of Pharmacy, 19th Ed., Volumes 1 and 2, Pharmaceutical Press (2012); and Formulation and Process Development Strategies for Manufacturing Biopharmaceuticals, Jameel, F. and Hershenson, S. eds. Wiley (2010); incorporated herein by reference). Such additives are nontoxic to the recipients at the dosages and concentrations employed.

In some embodiments, the antibody compositions include a buffering agent. Buffering agents help to maintain the pH in a desired range, such as a pH range which approximates physiological conditions. Suitable buffering agents for use with the antibodies of the present disclosure include both organic and inorganic acids and salts thereof, such as citrate, succinate, tartrate, fumarate, gluconate, oxalate, lactate, phosphate, histidine, Tris and acetate buffers.

In some embodiments, the carrier comprises a preservative to retard microbial growth. Suitable preservatives for use with antibody preparations include phenol, benzyl alcohol, meta-cresol, methyl paraben, propyl paraben, octadecyldimethylbenzyl ammonium chloride, benzalkonium halides (e.g., chloride, bromide, and iodide), hexamethonium chloride, and alkyl parabens such as methyl or propyl paraben, catechol, resorcinol, cyclohexanol, and 3-pentanol. In some embodiments, the preservative can be present in amounts ranging from 0.02%-1% (w/v).

In some embodiments, the carrier comprises isotonicifiers, sometimes referred to as "stabilizers" to ensure isotonicity of liquid compositions, examples of which include polyhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive that solubilizes the therapeutic agent or helps prevent denaturation or adherence to the container wall. Exemplary stabilizers can be polyhydric sugar alcohols enumerated above; amino acids such as arginine, lysine, glycine, glutamine, asparagine, histidine, alanine, ornithine, L-leucine, 2-phenylalanine, glutamic acid, threonine, etc.; organic sugars or sugar alcohols, such as lactose, trehalose, stachyose, mannitol, sorbitol, xylitol, ribitol, myo-inositol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, monothioglycerol and sodium thiosulfate; low molecular weight polypeptides (e.g., peptides of 10 residues or fewer); carrier proteins such as human serum albumin, bovine serum albumin, gelatin or immunoglobulins; hydrophilic polymers, e.g., polyvinylpyrrolidone; monosaccharides, such as xylose, mannose, fructose, glucose; disaccharides such as lactose, maltose, sucrose and trisaccharides such as raffinose; and polysaccharides such as dextran. In some embodiments, stabilizers can be present in the range from 0.1 to 10,000 weight per part of weight active protein.

Non-ionic surfactants or detergents, sometimes referred to as "wetting agents", can be added to help solubilize the antibody and protect it against agitation-induced aggregation, which also permits the formulation to be exposed to surface shear stress without causing denaturation of the protein. Suitable non-ionic surfactants include polysorbates (20, 80, etc.), poloxamers (184, 188, etc.), pluronic polyols, and polyoxyethylene sorbitan mono ethers (TWEEN®-20, TWEEN®-80, etc.). In some embodiments, non-ionic surfactants can be present in a range of about 0.05 mg/mL to about 1.0 mg/mL, for example about 0.07 mg/mL to about 0.2 mg/mL.

Additional excipients include bulking agents (e.g., starch), chelating agents (e.g., EDTA), antioxidants (e.g., ascorbic acid, methionine, vitamin E), and co-solvents.

Sterile injectable solutions can be prepared by incorporating the antibody in a sufficient amount in an appropriate solvent with one or a combination of ingredients enumerated above, as needed, followed by sterilization, such as by microfiltration. Generally, dispersions can be prepared by incorporating the antibody into a sterile vehicle that contains a basic dispersion medium and the other ingredients as needed from those enumerated above and known in the art. In the case of sterile powders for the preparation of sterile injectable solutions, preferred methods of preparation include vacuum drying and freeze-drying (lyophilization) that yield a powder of the antibody plus any additional desired carrier.

In some embodiments, the antibodies can be prepared with carriers that can protect the antibody against rapid release, such as a controlled release formulation, including implants and microencapsulated delivery systems. Biodegradable, biocompatible polymers can be used, such as ethylene vinyl acetate, polyanhydrides, polyglycolic acid, collagen, poly(orthoesters), and polylactic acid. Methods for preparing such formulations are generally known to those skilled in the art (see, e.g., Sustained and Controlled Release Drug Delivery Systems, J. R. Robinson, ed., Marcel Dekker, Inc., New York (1978)).

Various methods of mixing, solubilizing, stabilizing, concentrating, and lyophilizing to prepare the pharmaceutical compositions will use standard conventional techniques applicable to antibody therapeutics (see, e.g., Wang et al., 2007, J Pharm Sci. 96(1):1-26; Remington: The Science and Practice of Pharmacy, 19th Ed., Volumes 1 and 2, Pharmaceutical Press (2012); and Formulation and Process Development Strategies for Manufacturing Biopharmaceuticals, Jameel and Hershenson, eds., Wiley (2010)).

In some embodiments, the pharmaceutical compositions can be prepared in unit dose forms containing a predetermined amount of the antibody of the disclosure. In some embodiments, the unit dosage forms contain, without limitation, from about 5 mg to about 1 g, about 10 mg to about 1 g, 50 mg to about 1 g, 100 mg to about 1 g, 200 mg to about 1 g, or about 500 mg to about 1 g. In some embodiments, the unit dosage forms contain from about 5 mg to about 900 mg, about 10 mg to about 800 mg, about 50 mg to about 700 mg, about 100 mg to about 600 mg, or about 200 mg to about 500 mg. In some embodiments, the unit dosages can be determined based on the condition to be treated and/or route of administration. In some embodiments, the unit dosage forms can be prepared, by way of example and not limitation, as single use syringes, auto-inject pens, or lyophilized vials (e.g., for reconstitution with a pharmaceutically acceptable solution). Each unit dose can be packaged separately and supplied as kits containing one or more unit doses, e.g., two unit doses, three unit doses, four unit doses, or five unit doses or more.

6.4 Uses of the Antibodies

In another aspect, the antibodies of the disclosure can be applied to various diagnostic and therapeutic applications. In the area of diagnostics, in some embodiments, the antibody can be used to detect the presence and/or levels of sMIC proteins in biological samples, such as those obtained from patients who are suspected of or diagnosed with diseases characterized by elevated MIC protein levels, for example, epithelial cancers, hematologic malignancies, and autoimmune diseases. In some embodiments, the method of detecting sMIC comprises contacting a biological sample with an antibody of the disclosure; and determining or measuring the specific binding of the antibody to determine the level of sMIC in the sample. In some embodiments, the antibody is used in a method to detect the level of sMICA in a biological sample. In some embodiments, the antibody is used in a method to detect the level of sMICB in a biological sample. The diagnostic method can be used alone, or in combination with other methods and markers used as a diagnostic for a particular disease or disorder.

The biological sample can be any suitable sample taken from a subject for analysis, including cell samples, tissue samples and fluid samples. In some embodiments, the fluid sample includes, among others, blood, plasma, serum, urine, cerebrospinal fluid, lymph, synovial fluid, bile, semen, saliva, tears, and aqueous or vitreous humor. In some embodiments, the tissue sample includes biopsies of organs, solid tumors, preserved tissues, whole cells, and cell lysates. The biological sample can be prepared by methods known in the art which are suitable for the particular sample, and include, among others, disruption by mechanical means, exposure to freezing (e.g., liquid nitrogen), or by exposure to chemicals, such as detergents, acids, or bases prior to reaction with the antibody. Assays for detecting presence and/or levels of sMIC proteins include those typically used in the art, including among others, ELISA, immunohistochemistry, competitive and sandwich assays, and steric inhibition assays.

Detecting specific binding of the antibody (e.g., the antibody-sMIC protein complexes) can rely on use of an antibody containing a reporter molecule or a detectable label, for example, a fluorescent label, detectable enzyme, or a detectable conjugate system. In some embodiments, specific binding of the antibody can rely on a secondary detection agent, such as another antibody that binds specifically to the primary antibody. The secondary antibody can be labeled with a reporter molecule, a detectable label, or a detectable conjugate.

In some embodiments, the diagnostic methods herein can be used to detect levels of sMICA and/or sMICB in biological samples of subjects suspected of having a disease or disorder characterized by elevated MIC$^+$ levels, which may provide an indicator of the presence of the disease and/or the progression of the disease.

In some embodiments, the diagnostic methods can be used to detect levels of sMICA and/or sMICB in biological samples of a subject already diagnosed with a disease and/or disorder characterized by elevated MIC$^+$ levels, which may provide confirmation of the presence of the disease and/or the progression of the disease.

In some embodiments, the diagnostic methods can be used to detect levels of sMICA and/or sMICB in subjects who have undergone treatment, to determine the efficacy of a therapeutic agent and/or a therapeutic regimen, and/or the likelihood of disease relapse, based on the change in levels of sMICA and/or sMICB.

As noted above, various diseases are associated with elevated or abnormal levels of sMICA and/or sMICB. Although MICA and MICB and its interaction with NKG2D-bearing immune effector cells are involved in immunosurveillance of stressed or diseased cells that culminates in the death of the MIC$^+$ cells, the presence of soluble MIC proteins downregulates NKG2D receptor levels, enabling MIC$^+$ tumors to survive in the face of typically competent immune systems. For example, elevated levels of sMICA and/or sMICB have been identified in the blood of cancer patients but not in "normal" individuals, and this has been correlated with severity of the cancer staging (Salih et al., 2002, J Immunol. 169:4098-102; Doubrovina et al., 2003, J Immunol. 171:6891-9; Wu et al., 2004, J Clin Invest. 114:560-8; and Holdenreider, 2006, Intl J Cancer 118:684-7).

In some embodiments, the antibodies herein which bind selectively and specifically to sMICA and/or sMICB when they have been shed or released from the cell provides a basis for neutralizing the detrimental effects of sMICA and/sMICB. An advantage of using an antibody which selectively binds to the shed forms of MIC proteins is that the antibodies are unlikely to bind to MIC proteins expressed on surface of cells, thereby decreasing the likelihood of a pathological autoimmune reaction by improper activation of immune effector cells. In addition, an antibody's absence of significant binding to MICA and/or MICB present on cell membranes may preserve the immune mediated destruction of MIC expressing tumor cells, such as through NK cell mediated cytotoxic response. Accordingly, in some embodiments, the antibody of the disclosure can be used in a method of reducing the levels of sMICA and/or sMICB in a subject in need of such treatment (i.e., reduction), where the method comprises administering to a subject in need thereof an effective amount of the antibody of the disclosure to reduce the levels of sMICA and/or sMICB in the subject.

In some embodiments, the subject to be treated has elevated levels of a MIC protein, such as MICA and/or MICB. In various embodiments, the elevated levels of MIC protein are associated with the presence of a disease or disorder. The elevated levels can be on present on cells, tissues, or in a biological sample obtained from a subject. In some embodiments, the subject to be treated has elevated levels of sMICA and/or sMICB. The term "elevated" or its grammatical equivalents, including "higher," or "greater," etc., when in reference to the level of a molecule (e.g., MICA and/or MICB) that is an indicator of a disease or disorder, refers to the quantity of the molecule that is higher in populations with the disease or disorder in a statistically significant manner as compared to the level of the molecule in a population that does not have the disease (e.g., healthy subjects). In some embodiments, the level of MICA and/or MICB, such as sMICA and/or sMICB, in the disease population or a biological sample from a subject with the disease or disorder is at least 10% greater than, at least 25% greater than, at least 50% greater than, at least 75% greater than, and/or at least 90% greater than the level of the same molecule in the control population that does not have the disease or disorder, or a control biological sample obtained from a subject who does not have the disease or disorder.

A variety of diseases have been identified that display elevated levels of MICA and/or MICB. In various embodiments, such diseases include, among others, tumors, cancers, and hematologic malignancies. In some embodiments, the subject to be treated is afflicted with a MIC$^+$ tumor or cancer, or a MIC$^+$ hematologic malignancy. Accordingly, in some embodiments, the antibody of the disclosure can be used to treat a subject afflicted with a MIC$^+$ tumor or cancer, the method comprising administering to a subject afflicted with a MIC$^+$ tumor or cancer a therapeutically effective amount of an antibody described herein. In some embodiments, the MIC$^+$ tumor or cancer is a MICA$^+$ and/or MICB$^+$ tumor or cancer. In some embodiments, the MIC$^+$ tumor or cancer to be treated can be selected from brain cancer, biliary cancer, bone cancer, liver cancer, stomach cancer, testicular cancer, cervical cancer, ovarian cancer, vaginal and vulval cancer, endometrial cancer, melanoma, squamous cell carcinoma, malignant mesothelioma cancer, oral cancer, head and neck cancer, throat cancer, thymus cancer, gastrointestinal stromal tumor (GIST) cancer, nasopharyngeal cancer, esophageal cancer, colon cancer, anal cancer, breast cancer, lung cancer (e.g., non-small cell lung cancer, small cell lung cancer, bronchial cancer, etc.), prostate cancer, penile cancer, bladder cancer, pancreatic cancer, neuroblastoma, glioma, hepatocellular carcinoma, and renal cancer. In some embodiments, the antibody of the present disclosure is used in treating various types of epithelial tumors or cancers, including but not limited to, lung, breast, gastric, colon, pancreatic, liver, ovarian, renal cell, prostate carcinomas and melanoma. In some embodiments, the cancer selected for treatment is prostate cancer.

In some embodiments, the antibody is used in a method to treat a MIC$^+$ hematologic malignancy. Accordingly, in some embodiments, the antibodies of the disclosure can be used to treat a subject afflicted with a MIC$^+$ hematologic malignancy, the method comprising administering to a subject afflicted with a MIC$^+$ hematologic malignancy a therapeutically effective amount of an antibody described herein. In some embodiments, the MIC$^+$ hematologic malignancy is a MICA$^+$ and/or MICB$^+$ hematologic malignancy. In some embodiments, the hematologic malignancy is a leukemia or lymphoma. In some embodiments, the MIC$^+$ hematologic malignancy to be treated can be selected from, among others, Acute Lymphoblastic Leukemia (ALL), Acute Myelogenous Leukemia (AML), Chronic Lymphocytic Leukemia (CLL), Chronic Myelogenous Leukemia (CML), Acute Monocytic Leukemia (AMol), lymphomas (e.g., Hodgkin's lymphoma and Non-Hodgkin's lymphoma), and Multiple Myeloma.

In some embodiments, the antibody can be used to treat subjects having a viral infection characterized by elevated levels of a MIC protein, more particularly elevated levels of sMICA and/or sMICB. As discussed above, higher expression of MICA and/or MICB, particularly higher levels of sMICA and/or sMICB in viral infections appear to prolong and/or increase the severity of the infection by sMIC-mediated immune suppression. In some embodiments, a method of treating a subject with a viral infection characterized by elevated levels of a MIC$^+$ protein comprises administering to a subject afflicted with a viral infection characterized by elevated levels of a MIC$^+$ protein a therapeutically effective amount of an antibody of the present disclosure. In some embodiments, the MIC$^+$ viral infection is a MICA$^+$ and/or MICB$^+$ viral infection. Exemplary viral infections that display elevated sMIC protein levels include, among others, infections with hepatitis-B virus (HBV), respiratory syncytial virus (RSV), human rhinovirus (HRV), human cytomegalovirus (HCMV), hepatitis C virus (HCV), and human immunodeficiency virus (HIV).

In some embodiments, a method of treating a subject infected with a with hepatitis-B virus (HBV), respiratory syncytial virus (RSV), human rhinovirus (HRV), human cytomegalovirus (HCMV), hepatitis C virus (HCV), or human immunodeficiency virus (HIV: e.g., HIV-1, HIV-2) comprises administering to a subject infected with HBV, RSV, HRV, HCMV, HCV or HIV-1 a therapeutically effective amount of an antibody of the present disclosure.

Any of the antibody and the antibody compositions described herein, particularly the pharmaceutical compositions, can be administered to the subject. The antibody can be delivered to, without limitation, the joints, nasal mucosa, blood, lungs, intestines, muscle tissues, skin, or peritoneal cavity of a mammal. In some embodiments, the antibody composition can be administered intravenously, intraperitoneally, intramuscularly, subcutaneously, intrarectally, intravaginally, intrathecally, intratracheally, intradermally, orally or by inhalation, or by gradual perfusion over time. In a further example, an aerosol preparation of the antibody can be given to a subject by inhalation. A suitable route for administration in any given case will depend on, among others, the particular antibody, the subject, the nature and severity of the disease, and the physical condition of the subject.

The dosage administered can be based on, among others, the route of administration; the nature of the formulation; the nature of the subject's disease or disorder; the subject's size, weight, surface area, age, and sex as well as other drugs being administered. Wide variations in the dosages administered are to be expected in view of, among others, the variety of antibody compositions available, the differing efficiencies of various routes of administration, and the diseases or disorders to be treated. Variations in these dosage levels can be adjusted using standard empirical routines for optimization as is understood in the art. In some embodiments, for treatment of the indications described herein, the effective dose of an antibody of the disclosure can range from about 0.0001-100 mg/kg body weight, 0.001 to about 75 mg/kg body weight; 0.005 mg/kg to about 50 mg/kg body weight; about 0.01 mg/kg to about 30 mg/kg body weight; or about 0.01 to 5 mg/kg body weight. In some embodiments, the dosages can be about 0.001 mg/kg body weight, about 0.01 mg/kg body weight, about 0.3 mg/kg body weight, about 1 mg/kg body weight, about 3 mg/kg body weight, about 5 mg/kg body weight or about 10 mg/kg body weight, or within the range of 1-10 mg/kg body weight per single (e.g., bolus) administration.

Dosage regimens can be adjusted to provide the desired response, e.g., a therapeutic response, manageable toxicity or side effects, etc. For example, a single bolus may be administered, several divided doses may be administered over time, or the dose may be proportionally reduced or increased as needed by the therapeutic situation. The duration of treatment with any of the compositions provided herein can be any length of time from as short as one day to indefinitely, as needed. The administration can be a single bolus or the administration repeated, e.g., after one day, two days, three days, five days, one week, two weeks, three weeks, one month, five weeks, six weeks, seven weeks, two months, three months, or more. The repeated administration can be at the same dose or at a different dose. For example, a defined dosage regimen is continued for period of time, for example, 2 weeks to 6 months, from 3 months to 1 or 2 years, from 6 months to 3 or 4 years, from 8 months to 18 months, or the like, as necessary to treat the disease, e.g., eliminate the disease, cause remission, or halt disease progression. In some embodiments, the initial treatment can be a defined dosage regimen of 2 weeks to 2 months, followed by a maintenance dosage regimen, where the maintenance dosage can be the same or lower dose than the initial treatment, repeated as necessary to treat the disease or disorder, for example, a maintenance treatment of once every two weeks, once a month, once every two months, or once every four months, or on an as needed basis as determined by a medical professional.

In some embodiments, the antibody can be administered as a single dose or several doses over time. In some embodiments, the antibody can be administered as induction therapy, i.e., the first in a series of therapeutic measures used to treat a disease, followed by maintenance therapy with the antibody.

In some embodiments, the antibody can be used in combination with other therapeutic agents suitable for treating the disease or disorder characterized by elevated levels of MIC protein. In some embodiments, a method of treating cancer in a subject comprises administering to a subject in need thereof a therapeutically effective amount of an antibody of the present disclosure, and adjunctively administering a therapeutically effective amount of a second therapeutic agent to treat the cancer. In some embodiments, a method of treating a viral infection in a subject comprises administering to a subject in need thereof a therapeutically effective amount of an antibody of the present disclosure, and adjunctively administering a therapeutically effective amount of a second therapeutic agent to treat the viral infection. In the combination therapy, the antibody of the disclosure and one or more of the combination therapeutic agent can be administered concurrently (e.g., simultaneously), sequentially, together, or separately.

In some embodiments, the antibody of the disclosure is used in combination with chemotherapeutic agents used to treat tumors and cancers. Suitable chemotherapeutic agents can include, among others, cytotoxic agents, anti-metabolite agents (e.g., folate antagonists, purine analogs, pyrimidine analogs, etc.), topoisomerase inhibitors (e.g., camptothecin derivatives, anthracenedione, anthracyclines, epipodophyllotoxins, quinoline alkaloids, etc.), anti-microtubule agents (e.g., taxanes, vinca alkaloids), protein synthesis inhibitors (e.g., cephalotaxine, camptothecin derivatives, quinoline alkaloids), alkylating agents (e.g., alkyl sulfonates, ethylenimines, nitrogen mustards, nitrosoureas, platinum derivatives, triazenes, etc.), alkaloids, terpenoids, and kinase inhibitors. Exemplary chemotherapeutic agents typically used to treat proliferative disorders, such as cancers and tumors, include, by way of example and not limitation, afatinib, afuresertib, alectinib, alisertib, alvocidib, amonafide, amuvatinib, axitinib, azacitidine, azathioprine, bafetinib, barasertib, bendamustine, bleomycin, bosutinib, bortezomib, carfilzomib, ixazomib, oprozomib, delanzomib, marizomib, busulfan, cabozantinib, camptothecin, canertinib, capecitabine, cabazitaxel, carboplatin, carmustine, cenisertib, ceritinib, chlorambucil, cisplatin, cladribine, clofarabine, crenolanib, crizotinib, cyclophosphamide, cytarabine, dabrafenib, dacarbazine, dacomitinib, dactinomycin, danusertib, dasatinib, daunorubicin, decitabine, dinaciclib, docetaxel, dovitinib, doxorubicin, epirubicin, epitinib, eribulin mesylate, errlotinib, etirinotecan, etoposide, everolimus, exemestane, floxuridine, fludarabine, fluorouracil, gefitinib, gemcitabine, hydroxyurea, ibrutinib, icotinib, idarubicin, ifosfamide, imatinib, imetelstat, ipatasertib, irinotecan, ixabepilone, lapatinib, lenalidomide, lestaurtinib, lomustine, lucitanib, masitinib, melphalan, mercaptopurine, methotrexate, midostaurin, mitomycin, mitoxantrone, mubritinib, nelarabine, neratinib, nilotinib, nintedanib, omacetaxine mepesuccinate, orantinib, oxaliplatin, paclitaxel, palbociclib, palifosfamide tris, pazopanib, pelitinib, pemetrexed, pentostatin, plicamycin, ponatinib, poziotinib, pralatrexate, procarbazine, quizartinib, raltitrexed, regorafenib, ruxolitinib, seliciclib, sorafenib, streptozocin, sulfatinib, sunitinib, tamoxifen, tandutinib, temozolomide, temsirolimus, teniposide, theliatinib, thioguanine, thiotepa, topotecan, valproic acid, valrubicin, vandetanib, vemurafenib (Zelboraf), vincristine, vinblastine, vinorelbine, vindesine, and the like. In some embodiments, a chemotherapeutic agent can be chosen that does not adversely affect the subject's immune response.

In some embodiments, the antibodies can be used in combination with a biologic drug used to treat tumors and cancers. Exemplary biologic drugs that can be used in combination with the antibodies herein include, among others, anti-BAFF (e.g., belimumab); anti-CCR4 (e.g., mogamulizumab); anti-CD19/CD3 (e.g., blinatumomab); anti-CD20 (e.g., obinutuzumab, rituximab, ibritumomab tiuxetan, ofatumumab, tositumomab); anti-CD22 (e.g., moxetumomab pasudotox); anti-CD30 (e.g., brentuximab vedotin); anti-CD33 (e.g., gemtuzumab); anti-CD37 (e.g., otlertuzumab); anti-CD38 (e.g., daratumumab); anti-CD52 (e.g., alemtuzumab); anti-CD56 (e.g., lorvotuzumab mertansine); anti-CD74 (e.g., milatuzumab); anti-CD105; anti-CD248 (TEM1) (e.g., ontuxizumab); anti-CTLA4 (e.g., tremelimumab, ipilimumab); anti-EGFL7 (e.g., parsatuzumab); anti-EGFR (HER1/ERBB1) (e.g., panitumumab, nimotuzumab, necitumumab, cetuximab, imgatuzumab, futuximab); anti-FZD7 (e.g., vantictumab); anti-HER2 (ERBB2/neu) (e.g., margetuximab, pertuzumab, ado-trastuzumab emtansine, trastuzumab); anti-HER3 (ERBB3); anti-HGF (e.g., rilotumumab, ficlatuzumab); anti-IGF-1R (e.g., ganitumab, figitumumab, cixutumumab, dalotuzumab); anti-IGF-2R; anti-KIR (e.g., lirilumab, onartuzumab); anti-MMP9; anti-PD-1 (e.g., nivolumab, pidilizumab, lambrolizumab); anti-PD-L1; anti-PDGFRa (e.g., ramucirumab, tovetumab); anti-PD-L2; anti-PlGF (e.g., ziv-aflibercept); anti-RANKL (e.g., denosumab); anti-TNFRSF9 (CD137/4-1BB) (e.g., urelumab); anti-TRAIL-R1/DR4,R2/D5 (e.g., dulanermin); anti-TRAIL-R1/D4 (e.g., mapatumumab); anti-TRAIL-R2/D5 (e.g., conatumumab, lexatumumab, apomab); anti-VEGFA (e.g., bevacizumab, ziv-aflibercept); anti-VEGFB (e.g., ziv-aflibercept); and anti-VEGFR2 (e.g., ramucirumab).

In particular, the antibody described herein can be used in combination with therapeutic agents that modulate or activate, e.g., stimulate, the immune system. In some embodiments, these can comprise agents that positively activate the immune system, or agents that inhibit downregulation of immune activation. The immuno-activating or immune stimulating agents can be small molecule compounds, antibodies, anti-sense compounds, gene therapy, and the like. Various biological targets for therapeutic immune activation agents include, by way of example and not limitation, CTLA-4, KIR (Killer-cell immunoglobulin-like receptor), PD-1, PD-L1, PD-L2, CD137, CD227, IL-15 receptor, IL-6, IL-6 receptor, TGF-β1, TGF-β2, TGF-β3, and apolipoprotein J (Clusterin). In some embodiments, the immune system activating agent includes antibodies or other binding agents directed against the therapeutic targets, for example, anti- CTLA4, anti-PD-1, anti-PD-L1, anti-PD-L2, anti-CD137, anti-TGF-β1, anti-TGF-β2, anti-TGF-β3, and anti-apolipoprotein J (Clusterin). In some embodiments, the second therapeutic agent includes a checkpoint inhibitor, particularly anti-CTLA4, anti-PD-1, anti-PD-L1, or anti-PD-L2. Exemplary immune activating agents include, among others, ipilimumab, tremelimumab (Ribas et al., 2013, J Clin Oncol. 31:616-22), nivolumab (Wolchok et al., 2013, N Engl J Med. 369:122-33), BMS-936559 (MDX-1105: Brahmer et al., 2012, N Engl J Med. 366:2455-65), MEDI4736 (anti-PD-L1), MPDL3280A (anti-PD-L1), lambrolizumab (Hamid et al., 2013, N Engl J Med. 369:134-44), pidilizumab (anti-PD-1; Berger R et al 2008, Clin Can Res. 14:3044-51), AMP-224 (PD-L2-Ig), lambrolizumab, urelumab (Li and Liu, 2013, Clin Pharm: Advances & Application 5(Suppl 1):47-53), PF-05082566 (Fisher et al., 2012, Canc Immunol Immunother. 61:1721-33), ALT-803 (IL-15 superagonist complex; Xu et al, 2013, Canc Res. 73:3075-86; Zhu et al, 2009, J Immunol. 183:3598-607), AB-16B5 (anti-Clusterin), pirfenidone (Noble et al., 2011, Lancet 377:1760-9), fresolimumab (Trachtman et al., Kidney Int. 79:1236-43), sultiximab, and tocilizumab.

In some embodiments, the immune modulating or activating agent for use in combination with the antibodies can comprise a cytokine or chemokine, particularly a human form of the cytokine or chemokine, that stimulates the immune system response. In some embodiments, a method of treating a disease or disorder characterized by elevated levels of a MIC protein, for example a sMIC$^+$ cancer or viral infection, in a subject comprises administering to a subject in need thereof a therapeutically effective amount of an antibody of the present disclosure, and adjunctively administering a therapeutically effective amount of an immune modulating or activating cytokine or chemokine. Exemplary cytokines and chemokines can be selected from, among others, IL-2, IL-7, IL-12, IL-15, IL-18, IL-21, GM-CSF, IFN-α, and CCL-21, particularly IL-12 or IL-15. In some embodiments, the immune stimulating cytokines and chemokines can be used ex vivo to treat immune cells, particularly immune cells obtained from the subject or patient to be treated. In particular, immune activating agents which can stimulate NK cell activity, including by way of example and not limitation, IL-12 and IL-15, can be used in the combination treatments. In some embodiments, the cytokine or chemokine can be a recombinant form of the cytokine or chemokine.

In some embodiments, the antibody described herein can be used in combination with cancer vaccines, which includes antigen presenting cells (e.g., dendritic cells) activated with cancer vaccines. Exemplary cancer vaccines include, among others, prostatic acid phosphatase (e.g., Provenge®); gp-96-Ig (e.g., HS-410); PANVAC; HER2/neu (e.g., nelipepimut-S, AVX901); DCVax(R)-L; rindopepimut; IMA950 (multi tumor associated peptides); tumor-derived heat shock protein gp96 (Vitespen); surviving peptide (e.g., ISA-51: US patent publication 20110091489); EGFRvIII-NY-ESO-1 (e.g., ADU-623); CD-133; folate binding protein vaccines E39 and J65; HLA-A2 tumor antigen peptides; carcinoembryonic antigen (CEA); universal tumor antigen oncofetal antigen/immature laminin receptor protein (OFA/iLRP); mammaglobin-A; bi-shRNAfurin; HLA-A*2402 restricted epitope peptides CDCA1, URLC10, KIF20A, DEPDC1 and MPHOSPH1; hyperglocosylated MUC1 (e.g., ONT-10); poly-ICLC; human telomerase reverse transcriptase (e.g., hTERT, UV1, GV1001); HPV P16 37-63-peptide; HPV-16-E7 (e.g., ADX11-001), pNGVL4a-Sig; Herpes Zoster vaccine GSK1437173A; NY-ESO-1 antigen; leukemia-associated antigen WT1; bcr-abl p210-b3a2 breakpoint-derived pentapeptide CMLVAX100; lung cancer cell with GM-CSF (e.g., GVAX); Wilms tumor gene 1 (WT1) peptide (e.g., OCV-501); human MUC1 antigen (e.g., L-BLP25); MUC1 peptide tecemotide; HLA-A*0201 restricted epitope peptide URLC10, VEGFR1 and/or VEGFR2 9URLC10; cancer-testis antigens (e.g., URLC10, CDCA1, KIF20A, MAGE-C1, MAGE-A3/6, etc.); autophagosome-enriched vaccine Dribble, L523S protein; RNActive derived lung cancer vaccine CV9202; CSF-470 vaccine; melanoma antigen MAGE-3.A1; melanoma antigen NA17.A2; melanoma antigen IMP321; melanoma antigen LAG-3; IBBL antigen (e.g., A2/4-1BBL) melanoma vaccine; MART-1; gp100 (e.g., g209-2M, G280-9V); KRN7000; PVX-410; PROSTVAC; peptide pyroEHWSYGLRPG (PEP223); prostate specific antigen; and PSMA antigen (e.g., BPX-201).

In some embodiments, the cancer vaccine used in combination with the antibodies can be tumor cells or tumor cell lysates, which vaccines include antigen presenting cells (e.g., dendritic cells) activated with tumor cells or tumor cell lysates. Exemplary tumor cells and corresponding tumor cells lysates useful as vaccines include, among others, bladder cancer cells, glioblastoma cells, breast cancer cells, cervical cancer cells, lymphoma cells, kidney cancer cells, leukemic cells, lung cancer cells, melanoma cells, multiple myeloma cells, non-Hodgkin's lymphomas, pancreatic cancer cells, liver cancer cells, and prostate cancer cells.

In some embodiments, the antibodies can be used in combination with antiviral drugs used to treat viral infections characterized by presence of elevated MIC, for example, infections with hepatitis-B virus, respiratory syncytial virus, human cytomegalovirus, hepatitis c virus, human rhinovirus, and human immunodeficiency virus. Drugs for treating hepatitis-B viral infections include, among others, interferons (e.g., interferon alpha-2b or pegylated interferon), lamivudine, adefovir dipivoxil, entecavir, telbivudine, and tenofovir. Drugs for treating respiratory syncytial virus include, among others, RSV hyperimmune globulin; palivizumab; benzimidazoles BMS-433771, TMC353121 and JNJ-2408068; ribavirin; and antisense phosphorodiamidate morpholino oligomers (see review Olszewska and Openshaw, 2009, Expert Opin Emerg Drugs 14(2): 207-17). Drugs for treating hepatitis C virus include, among others, interferons (e.g., interferon alpha-2b or pegylated interferon), boceprevir, telaprevir, ribavirin, simeprevir, sofosbuvir, daclatasvir, velpatasvir, elbasvir, grazoprevir, ombitasvir, paritaprevir, ritonavir, dasabuvir, ledipsavir and combinations thereof. Drugs for treating human immunodeficiency virus include, among others, efavirenz, emtricitabine, tenofovir disoproxil fumarate, rilpivirine, cobicistat, lamivudine, zidovudine, abacavir, zalcitabine, stavudine, nevirapine, etravirine, delavirdine, tipranavir, indinavir, saquinavir mesylate, lopinavir, ritonavir, darunavir, atazanavir sulfate, nelfinavir mesylate, maraviroc, raltegravir, enfuvirtide, and combinations thereof.

In some embodiments of the combination therapy, the antibody described herein can be used prior to, concurrently with, or subsequent to the administration of the other therapeutic agent. In some embodiments, the antibody of the disclosure and the combination therapeutic agent can be administered successively to the patient on the same day, for example during the same patient visit. Successive administration can occur 1, 2, 3, 4, 5, 6, 7 or 8 hours or more hours apart. In some embodiments, the antibody of the disclosure and the combination therapeutic agent can be administered separately, e.g., on different days, for example, the antibody and the combination therapeutic agent can be administered at a 1-day, 2-day or 3-day, one-week, 2-week or monthly intervals. Other treatment regimens for the combination of the antibody of the disclosure and other therapeutic agents will be apparent to the skilled artisan in light of the guidance herein.

In another aspect, the present disclosure provides articles of manufacture and kits containing materials useful for practicing the antibodies and methods described herein. In some embodiments, the article can comprise a container comprising the antibodies of the present disclosure. Suitable containers include, among others, bottles, vials, bags, and syringes. The containers can be made of various materials, such as plastic or glass. In some embodiments, the containers can have a sterile access port, for example, a stopper or membrane for inserting a hypodermic injection needle. In some embodiments, the kits comprise a syringe, particularly a single use syringe or auto-inject pen syringe filled with a dose of the antibody of the present disclosure, particularly a defined unit dose of the antibody.

In some embodiments, the articles can also include at least a second container containing materials to be used in combination with the antibodies, such as sterile water or sterile buffer, for example for reconstituting the compositions. In some embodiments, the second container or a third container can comprise an additional therapeutic agent, including, a chemotherapeutic agent or biological agent for use in combination with the antibody compositions of the present disclosure.

In some embodiments, the article comprises a label or package insert that describes the composition used for treating one or more disease conditions. The articles can also include instructions or descriptions of the compositions and instructions for their use on a suitable electronic medium, such as optical discs and static random access memory chips.

The articles of manufacture can be provided in the form of kits comprising the containers, package inserts, and/or electronic medium. It may further include other materials desirable for commercial distribution and the user, such as other buffers, diluents, filters, needles and syringes.

Having now generally described the invention, the same will be more readily understood through reference to the following examples which are provided by way of illustration, and are not intended to be limiting.

7. EXAMPLES

Example 1: Methods Related to Generation of Monoclonal Antibodies to the Alpha-3 Domain of MICA Production of Extracellular Alpha-3 Domain MICA Immunogen by Baculovirus Expression.

To prepare the extracellular alpha-3 domain of MICA as an immunogen for antibody production, a Baculovirus protein expression system was used to generate the appropriate protein glycosylation on expressed MICA. Recombinant alpha-3 domain MICA cDNA (allele 001) corresponding to the GenBank MICA sequence NP_000238.1 (FIG. 1) encoding residues 205 to 297 of the alpha-3 domain of MICA (FIG. 1C: SEQ ID NO:3), which are amino acid residues 182 to 274 of the processed MICA protein (e.g., FIG. 4-A), was synthetically generated along with convenient restriction enzymes sites for further subcloning into the Baculovirus transfer vector, and then ligated into an appropriate DNA cloning vector. The Baculovirus transfer vector contained a six C-terminal Histidine residue tag for purification. Exemplary MICA peptide immunogens with purification tags and cleavage sites can also be selected from the following, where the MICA sequences are underlined:

(a)
(SEQ ID NO: 46)
MEFVPPMVNVTRSEASEGNITVTCRASGFYPWNITLSWRQDGVSLSHDTQ

QWGDVLPDGNGTYQTWVATRICQGEEQRFTCYMEHSGNHSTHPVPSENLY

FQGHHHHHH;

(b)
(SEQ ID NO: 47)
MEFRSEASEGNITVTCRASGFYPWNITLSWRQDGVSLSHDTQQWGDVLPD

GNGTYQTWVATRICQGEEQRFTCYMEHSGNHSTHPVPSENLYFQGHHHHH

H;

(c)
(SEQ ID NO: 48)
MEFRSEASEGNITVTCRASGFYPWNITLSWRQDGVSLSHDTQQWGDVLPD

GNGTYQTWVATRICQGEEQRFTCYMEHSGNHSTHENLYFQGHHHHHH;
and (d)
(SEQ ID NO: 49)
MEFRSEASEGNITVTCRASGFYPWNITLSWRQDGVSLSHDTQQWGDVLPD

GNGTYQTWVATRICQGEEQRENLYFQGHHHHHH.

A similar strategy can be taken to prepare the alpha-3 domain from MICB as the recombinant protein to be used in immunization of mice (sequence presented in FIG. 1D: SEQ ID NO:4). Exemplary MICB peptide immunogens with purification tags and cleavage sites can also be selected from the following, where the MICB sequences are underlined:

(a)
(SEQ ID NO: 50)
MEFVPPMVNVTCSEVSEGNITVTCRASSFYPRNITLTWRQDGVSLSHNTQ

QWGDVLPDGNGTYQTWVATRIRQGEEQRFTCYMEHSGNHGTHPVPSENLY

FQGHHHHHH;

(b)
(SEQ ID NO: 51)
MEFCSEVSEGNITVTCRASSFYPRNITLTWRQDGVSLSHNTQQWGDVLPD

GNGTYQTWVATRIRQGEEQRFTCYMEHSGNHGTHPVPSENLYFQGHHHHH

H;

(c)
(SEQ ID NO: 52)
MEFCSEVSEGNITVTCRASSFYPRNITLTWRQDGVSLSHNTQQWGDVLPD

GNGTYQTWVATRIRQGEEQRFTCYMEHSGNHGTHENLYFQGHHHHHH;
and (d)
(SEQ ID NO: 53)
MEFCSEVSEGNITVTCRASSFYPRNITLTWRQDGVSLSHNTQQWGDVLPD

GNGTYQTWVATRIRQGEEQRENLYFQGHHHHHH.

Upon confirmation of both the MICA and the additional DNA sequences in the subclone, a Baculovirus expression system was used to recombine the two DNA components in *E. coli* bacteria to generate a bacmid construct containing the recombinant viral DNA. A recombinant bacmid clone with the correct sequence was used to produce recombinant Baculovirus by transfection into Sf9 insect cells.

In order to produce recombinant protein, Sf9 cells were infected with recombinant virus in serum-free medium, such as SF-900 (Life Technologies), and the cells harvested at day 4 or 5 after infection. To purify the MICA alpha-3 domain polypeptide from the infected cells, the cells were lysed, centrifuged briefly to collect the supernatant, and then subjected to affinity chromatography using $Ni^{2+}$ chelation. Protein recovery was improved by the addition of 8M urea to the sample buffer prior to chromatography. Dialysis against a carbonate buffer was used to remove the urea. The pure protein may also be concentrated by centrifugation filters (Amicon) to achieve a more stable protein preparation.

Monoclonal Antibody Generation and Primary Screening.

The alpha-3 domain MICA immunogen was prepared in an aqueous solution (about 0.5 mg/ml) and injected five times over a two-week period into immunocompetent mice using a RapidPrime™ method (ImmunoPrecise, British Columbia, Canada). Following immunization, the lymphocytes from the lymph tissue of the immunized mice were removed and the lymphocytes chemically fused with, but not limited to, polyethylene glycol (PEG) or a PEG derivative, to murine SP2/O myeloma cells for immortalization. The fused cells were grown in a methylcellulose-containing semi-solid HAT drug-selection medium in order to select clonal B-cell/myeloma fusion hybridoma cells capable of producing antibodies. The primary screening of hybridoma clones involved testing antibody-containing supernatants for their ability to bind recombinant antigen (alpha-3 domain of MICA) by ELISA. The primary screen produced 146 hits from a total of 948 (15%) hybridoma clones assayed, while the isotyping assay identified 98/146 clones (67%) for a specific antibody type, equivalent to 10% of the 948 initial clones.

Secondary Screening Using Indirect ELISA.

Several secondary indirect ELISA screens were performed to help select high quality hybridoma clones for further analysis. Hybridoma supernatant containing antibody were assessed for binding to: (a) test alpha-3 domain MICA protein; (b) a His-tagged protein with no relation to MIC proteins to rule out potential His tag binding antibodies; (c) recombinant *E. coli*-produced ectodomain protein from human MICA (including complete alpha-3 subdomain, but without a His-tag) (Bio Basic, Markham, Canada); and (d) recombinant *E. coli*-produced ectodomain protein from human MICB (including complete alpha-3 subdomain, but without a His-tag) (Bio Basic, Markham, Canada).

The proteins above were bound to an ELISA plate overnight at 4° C. at a concentration ranging from 0.1 to 0.2 μg per well in carbonate buffer (pH 9.6). The plates were then blocked with skim milk powder/PBS pH 7.4, washed and then treated for 1 hour with primary antibody (100 μl of hybridoma supernatant) or with positive control MIC murine monoclonal antibodies (BAMO3, a MIC alpha-3 specific $IgG_{2a}$ mAb; and BAMO1, a MIC alpha 1+2 specific $IgG_1$ mAb; both from MBL International, MA, USA) or with isotype-matched negative control antibodies. After washing, the wells were treated with secondary goat anti-mouse IgG/IgM (H+L)-HRP conjugated antibody for 1 hour. HRP substrate, tetramethylbenzidine (TMB), was added to the washed wells, and the color was developed for 5 minutes in the dark. The reactions were stopped by the addition of 1M HCl, and the plates were read at 450 nm.

These ELISA experiments resulted in only a minor number of hybridoma supernatants reacting very weakly with the His-tagged protein, suggesting that the antibodies generated were target, i.e., MICA, specific. Many of the hybridomas tested produced antibodies that bound strongly to both the alpha-3 target MICA protein as well as to the bacterially-produced MICA and/or MICB proteins, enabling the collection of different clones with varying binding capabilities. The ELISA experiments also indicated, retrospectively, that control MIC antibody BAMO3 (MIC alpha-3 specific), but not BAMO1 (MIC alpha 1+2 specific), was capable of producing strong signal by indirect ELISA against the recombinant alpha-3 MICA target protein, confirming that the test alpha-3 domain antigen was indeed correctly expressed in the Baculovirus system.

Secondary Screen Using Flow Cytometry Assay.

A secondary screen used the same antibody-containing supernatants to test for their ability to bind recombinant extracellular regions (alpha-1, -2 and -3 domains) of MICA or MICB proteins by indirect ELISA, and for their inability to bind MIC proteins on the cell surface of MIC expressing heat-shocked HCT116 colon carcinoma and DU-145 prostate cancer cells by flow cytometric analysis.

To assay for binding to cell bound MIC protein, MIC expressing heat-shocked DU-145 prostate cancer cells were heat-treated at 42° C. for 90 min and then allowed to recover for 22 hr at 37° C. Upon recovery, a trypan blue viability test was performed on non-enzymatically-dissociated cells, and a viability level of 97% was determined. Heat-treated DU-145 cells were then treated with primary antibody which was selected from one of the following: (a) test hybridoma supernatant; (b) positive control murine antibodies capable of binding to the alpha-3 MIC subdomain only (BAMO3 mAB described above: MBL International, MA, USA), or (c) negative control murine antibodies isotype-matched to either the positive control antibody or to the test hybridoma supernatants. After incubation and extensive washing, the cells were treated with fluorescein isothiocyanate (FITC)-conjugated goat anti-mouse IgG secondary antibody (Santa Cruz Biotechnology Inc., CA, USA). Cells were then stained with propidium iodide (PI) to measure viability, re-suspended in preservative buffer, and then subjected to flow cytometry on a BD FACS-Caliber machine.

Strong binding to the cell surface was detected with the positive control antibody (alpha-3 specific), but no binding was observed with either negative control antibodies or with hybridoma test supernatants whose antibodies had previously been determined to bind to the MICA alpha-3 subdomain recombinant protein and to bacterially-expressed MICA or MICB extracellular domain recombinant proteins in ELISA assay format. Specifically, antibody from hybridoma clone 5C9 ($IgG_2$) was incapable of binding to the cell-surface expressed MIC proteins on DU-145 cells (FIG. 9).

Example 2: Characterization of Antibodies Binding to MIC Protein

Analysis of Binding Affinity.

Biomolecular interactions between MICA alpha-3 recombinant antigen and test antibody were directly measured by Bio-Layer Interferometry (BLI) using a Pall ForteBio Octet RED96 machine (Pall ForteBio, CA, USA). Real-time kinetic analyses were performed on the test MICA monoclonal antibody 5C9, as well as two control antibodies, one of which could bind the alpha-3 MICA subdomain antigen (positive control) and one of which could not (negative control), as previously determined by ELISA. The Octet RED96 apparatus operates under the principle of Bio-Layer Interferometry, a label-free technique that measures molecular interactions and complex formation. A key component of the technique is the optical biosensor whose tip is immersed in the fluids of the test well and then used to assay interference patterns between waves of light. Here, the ligand (monoclonal antibody) is localized to the surface of the biosensor through capture by previously bound anti-mouse IgG, while the analyte biomolecule (antigen) is kept in solution. Binding responses between ligand and analyte were measured and reported in real-time. Both association and dissociation kinetics were monitored and $K_D$ values were calculated. This model assumed a 1:1 interaction of ligand to analyte.

At pH 7.4, the affinity constant $K_D$ for the positive control MICA antibody (BAMO3) with respect to binding the MICA alpha-3 recombinant protein was about $6.0 \times 10^{-9}$ M. The negative control antibody that does not bind tightly had a $K_D$ of about $9.6 \times 10^{-6}$ M. Antibody from clone 5C9 had a measured $K_D$ of about $3.3 \times 10^{-9}$ M.

Sequencing of Antigen Binding Domains.

Hybridoma cells were lysed with detergent-containing buffer, and mRNA was isolated by standard procedures. RT-PCR was carried out using 5' RACE (RLM-RACE) and gene specific reverse primers, which amplify mouse immunoglobulin heavy chain ($IgG_1$) and light chain (kappa) variable region sequences. The reaction mixture was separated by gel electrophoresis, and the specific PCR bands were gel-excised. The purified PCR product was cloned into pCR-Blunt II-TOPO vector, and the constructs transformed into E. coli. Twenty three colonies of each chain were picked and PCR screened for the presence of amplified regions prior to sequencing. PCR positive clones (about 8 to 10) for each chain were sequenced. DNA sequences were analyzed by BLAST to confirm homology to mouse antibody sequences. Sequences of the variable regions of antibody 5C9 are depicted in FIG. 7 (A-H).

Example 3: Epitope Mapping of MIC Antibodies

The epitope bound by the antibodies were determined using the HiSense™ Epitope mapping procedure from Pepscan Presto BV (Lelystad, The Netherlands). A series of overlapping synthetic peptides derived from the MICA*001 alpha-3 sequence were constructed to assess binding to the test antibody. In addition, MICA peptides containing double alanine mutations were produced and used to confirm the importance of specific amino acids to antibody binding capability.

Synthesis of Peptides:

To reconstruct epitopes of the target molecule, a library of peptides was synthesized. An amino functionalized polypropylene support was obtained by grafting with a hydrophilic polymer formulation, followed by reaction with t-butyloxycarbonyl-hexamethylenediamine (BocHMDA) using dicyclohexylcarbodiimide (DCC) with N-hydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer). Finally, the peptide arrays were washed extensively with an excess of $H_2O$ and sonicated in disruption buffer containing 1% SDS/0.1% beta-mercaptoethanol in PBS (pH 7.2) at 70° C. for 30 minutes, followed by sonication in $H_2O$ for another 45 minutes.

ELISA Screening:

The binding of antibody to each of the synthesized peptides was tested in a Pepscan-based ELISA. The peptide arrays were incubated with primary antibody solution (overnight at 4° C.). After washing, the peptide arrays were incubated with a 1/1000 dilution of an appropriate antibody peroxidase conjugate (SBA; rabbit anti-mouse IgG (H+L) HRP conjugate, Southern Biotech) for one hour at 25° C. After washing, the peroxidase substrate 2,2'-azino-di-3-ethylbenzthiazoline sulfonate (ABTS) and 20 µl/ml of 3% $H_2O_2$ were added. After one hour, the color development was measured. The color development was quantified with a charge coupled device (CCD)—camera and an image processing system.

Results:

Software developed by Pepscan was used to determine the epitope. Recorded data from analysis of over 400 peptides suggested that the 5C9 antibody recognized peptides with core sequence of 228_QQWGDVLP_235 (SEQ ID NO:22) based on numbering from processed MICA sequence. Additionally, the data indicated that peptides with double alanine mutations of MICA residues in the range of 231_GDVL_234 (SEQ ID NO:23) abolished binding of the antibody. To assess structural characteristics of the identified linear epitope a 3D structure of human MICA was used. FIG. 6 depicts the surface localization of the epitope residues on MICA interacting with antibody 5C9 based on the epitope mapping studies.

Example 4: Assessing Binding to MIC Proteins Shed from Prostate Cancer DU-145 Cells To demonstrate antibody binding to MIC ligands shed from DU-145 prostate cancer cells, a subtractive immunoprecipitation method was employed to monitor and quantitate specific binding. In this procedure, DU-145 cells (from ATCC) were grown to high density and then heat-shocked at 42° C. for 90 minutes. The tissue culture medium was then changed to a 2% FBS low-serum containing medium and the cells were allowed to recover for 48 hours. At this point the conditioned medium was harvested and frozen for later use. Protein G PLUS-agarose beads (Santa Cruz Biotechnology, CA) were used to bind positive control antibody BAMO3 (IgG2a), test hybridoma supernatant antibody (IgG2b), or appropriate normal mouse isotype controls (various isotypes; Santa Cruz Biotechnology, CA) at 4° C. for 3 hours. After incubation, the beads possessing the freshly bound antibody were washed extensively for further use in assessing their ability to bind shed sMIC ligands in the DU-145 conditioned medium. Treated beads were then added to defined amounts of conditioned medium and were then incubated at 4° C. overnight with gentle agitation in order to induce immunoprecipitation. Following incubation the beads were gently centrifuged to pellet the beads, and the beads removed from the test conditioned medium and discarded. Antibody/bead complexes that bind the sMIC ligands will cause a reduction in the level of sMIC ligands in the remaining conditioned medium, which can then be assayed by ELISA. The predominant sMIC ligand released by DU-145 cells was determined to be sMICB, and as such was assayed using a MICB ELISA kit from MBL International, MA (Ab-Match Assembly Human MICB kit together with the Ab-Match Universal buffer kit) (see FIG. 10). Treatments where antibody/bead complexes captured sMICB resulted in a decreased ELISA signal compared with isotype (negative) controls. The purified BAMO3 MICA/B antibody (which is also capable of binding MICA/B when membrane-bound) served as a positive control and reduced the amount of sMICB in the sample by approximately 83%.

The 5C9 antibody from hybridoma supernatants reduced the sMICB levels by approximately 51% compared to isotype controls.

Example 5: Effect on Growth of Prostate Cancer DU-145 Xenografts in Rag2$^{-/-}$ Mice DU-145 cells were grown in modified Eagle's Minimum Essential Medium containing 2 mM L-glutamine, 1 mM sodium pyruvate, 0.1 mM non-essential amino acids, 1.5 g/L sodium bicarbonate and 10% FBS, at 37° C. in a 5% $CO_2$ environment. On Study Day 0, $5.0 \times 10^6$ DU-145 tumor cells were implanted subcutaneously into the backs of male Rag2$^{-/-}$ mice. The mice were randomized into various treatment arms on Study Day 31. All treatment arms commenced dosing on Study Day 32 and were completed on Study Day 56. Mice were weighed twice weekly and, where indicated by protocol, injected intraperitoneally with 400 µg of isotype control or 5C9 antibody twice a week, except the last week when they were dosed three times. Mice scheduled to be dosed with recombinant mouse IL-12 (BioLegend, CA) received peritumoral injections of 0.5 µg three times a week. Tumor growth was monitored by measuring tumor dimensions with calipers. Tumor length and width measurements were obtained 2 times weekly for entire study. Tumor volumes were calculated according to the equation $L \times W^2/2$ with the length (mm) being the longer axis of the tumor. Blood samples were collected on Study Days 10, 36, 43 and at termination. Serum was generated from the blood samples and used later in ELISA experiments to measure sMICB levels. At study termination, spleens were collected and weighed.

Results:

Xenograft Model: FIG. 11 shows the mean tumor volumes from each study arm over time. In comparison to isotype control, both monotherapies (5C9 antibody or IL-12) were insignificantly different (P>0.05, Student's T-test, 2-tailed), although a reduction in mean tumor size of 30% and 32%, respectively, was noted for these arms when measured on Study Day 58 (FIG. 12). A statistically significant decrease (53%) in mean tumor volume was noted for the combination treatment using 5C9 antibody and IL-12 (P<0.05), assessed on Study Day 58. These data are consistent with the suggested mechanism of action of the 5C9 antibody in binding to and reducing the blood levels of sMICB thereby promoting recognition of surface bound MIC ligands by its cognate receptor NKG2D on NK cells, which is enhanced by addition of immune-stimulating IL-12. With respect to spleen weights (FIG. 14), a statistically significant difference is found between the isotype control and the 5C9 alone or 5C9 plus IL-12 treatment arms where spleen weights increased by approximately 2 or 3 fold, respectively, compared to isotype control. No significant difference was noted for the treatment arm containing IL-12 alone. No significant weight loss during treatment, or gross toxicity at necropsy, was noted for any of the animals on the study.

Immunoassay:

FIG. 13 shows the results of an ELISA performed to assess the level of sMICB in the mouse sera. sMICB levels increased as tumors grew in size and, accordingly, only very low levels were detectable at the early time point on Study Day 10, whereas higher levels were generally noted as the study and tumor volumes progressed. On Study Days 36, 43 and 53-58 the sMICB levels were determined from the sera samples of the four study arms. A statistically significant reduction was reached when comparing the combination treatment group of mAb 5C9 plus IL-12 (Student's T-test, 2-tailed; P values=0.03, 0.001 and 0.002, on Study Days 36, 43 and 53-58, respectively) to the isotype control. The statistical analysis suggested that significance was approached for the treatment arm containing mAb 5C9 alone on Study Days 36 (P=0.08) and 43 (P=0.09). Of note was the fact that a delay in reduction of sMICB levels occurred in the IL-12 treatment alone arm compared to the 5C9 alone on Study Day 36, potentially suggesting differences in mechanism of action between treatment types.

In addition to sMICB, the mouse sera were also assayed for IFN-γ by sandwich capture ELISA. To measure IFN-γ, the Affymetrix/eBioscience Mouse IFN-γ ELISA Ready-Set-Go kit was used according to the manufacturer's instructions. FIG. 15 shows the changes in IFN-γ on study day 36. P values were calculated using Student's T-test (2-tailed). P values below 0.05 considered significant. The designation "*" in FIG. 15 refers to P<0.05. Neither 5C9 nor IL-12 monotherapies were significantly different than isotype control; however, the combination treatment of 5C9 and IL-12 was significantly different than either monotherapy or the isotype control (Student's T-test, 2-tailed; P values<0.05). Testing the mouse sera for IFN-γ on later study days suggested that all treatment groups had only low levels and were insignificantly different from one another (data not shown).

IP-10 (CXCL10) was also assayed from mouse sera on study days 10, 36, 43 and 58 using the Abcam SimpleStep ELISA kit according to the manufacturer's instructions. FIG. 16 shows the changes in IP-10 over the course of the study. A significant increase (Student's T-test, 2-tailed; P values<0.05) in IP-10 was noted for treatment groups including both 5C9 and IL-12 monotherapies, as well as for the combination of 5C9 with IL-12, on study day 36 compared to isotype control. The combination treatment group continued to be significantly different than isotype control on study days 43 and 58. The mean IP-10 levels for all drug treatment groups appeared to peak at or around study day 36, but decreased thereafter. These data are consistent with induction of IP-10 by expression of IFN-γ in response to treatment.

The foregoing descriptions of specific embodiments of the present invention have been presented for purposes of illustration and description. They are not intended to be exhaustive or to limit the invention to the precise forms disclosed, and many modifications and variations are possible in light of the above teaching.

All patents, patent applications, publications, and references cited herein are expressly incorporated by reference to the same extent as if each individual publication or patent application was specifically and individually indicated to be incorporated by reference.

What is claimed is:

1. An isolated antibody comprising a CDR L1, CDR L2 and CDR L3 in the light chain variable region amino acid sequence of SEQ ID NO:25, and a CDR H1, CDR H2 and CDR H3 in the heavy chain variable region amino acid sequence of SEQ ID NO:29, wherein the antibody binds specifically to soluble MICA (sMICA) or soluble MICB (sMICB) protein.

2. The isolated antibody of claim 1, wherein the CDR L1 comprises the amino acid sequence of RSSQSIVHSNGNTYLE (SEQ ID NO: 40); the CDR L2 comprises the amino acid sequence of KVSNRFS (SEQ ID NO: 41); the CDR L3 comprises the amino acid sequence of FQGSHVPFT (SEQ ID NO: 42); the CDR H1 comprises the amino acid sequence of NYLIE (SEQ ID NO: 43); the CDR H2 comprises the amino acid sequence of LIYPGSGGTNYNEKFKG (SEQ ID NO: 44); and the CDR H3 comprises the amino acid sequence of IYYGNRDYGMDY (SEQ ID NO: 45).

3. The isolated antibody of claim 1, comprising a light chain variable region VL comprising the amino acid sequence of SEQ ID NO: 25 and a heavy chain variable region VH comprising the amino acid sequence of SEQ ID NO: 29.

4. The isolated antibody of claim 1, comprising a human heavy chain isotype selected from human $IgG_1$, $IgG_2$, $IgG_3$, and $IgG_4$.

5. The isolated antibody of claim 1, wherein the antibody is a monoclonal antibody.

6. The isolated antibody of claim 1, wherein the antibody is a chimeric antibody.

7. The isolated antibody of claim 1, comprising an antibody fragment.

8. The isolated antibody of claim 1, wherein the antibody is a purified antibody.

9. A pharmaceutical composition comprising the isolated antibody of claim 1, and a pharmaceutically acceptable carrier.

10. A method of attenuating an elevated level of human soluble MICA (sMICA) protein or soluble MICB (sMICB) protein in a mammalian subject in need thereof comprising administering to said subject an effective amount of an isolated antibody comprising a CDRL 1, CDR L2 and CDR L3 in the light chain variable region amino acid sequence of SEQ ID NO: 25, and a CDR H1, CDR H2 and CDR H3 in the heavy chain variable region amino acid sequence of SEQ ID NO: 29, wherein the antibody binds specifically to the sMICA protein or the sMICB protein and wherein the mammalian subject has a $MICA^+$ or $MICB^+$ tumor or cancer.

11. The method of claim 10, wherein the mammalian subject has brain cancer, liver cancer, stomach cancer, testicular cancer, cervical cancer, ovarian cancer, vaginal and vulval cancer, melanoma, squamous cell carcinoma, malignant mesothelioma cancer, oral cancer, head and neck cancer, throat cancer, thymus cancer, gastrointestinal stromal tumor (GIST) cancer, nasopharyngeal cancer, esophageal cancer, colon cancer, anal cancer, breast cancer, lung cancer, prostate cancer, penile cancer, bladder cancer, pancreatic cancer, neuroblastoma, glioma, hepatocellular carcinoma, or renal cancer.

12. The method of claim 10, wherein the mammalian subject has a hematologic cancer.

13. The method of claim 12, wherein, the hematologic cancer is leukemia or lymphoma.

14. The method of claim 13, wherein the hematologic cancer is selected from Acute Lymphoblastic Leukemia (ALL), Acute Myelogenous Leukemia (AML), Chronic Lymphocytic Leukemia (CLL), Chronic Myelogenous Leukemia (CML), Acute Monocytic Leukemia (AMol), Hodgkin's lymphoma, Non-Hodgkin's lymphoma and Multiple Myeloma.

15. The method of claim 10, wherein the CDR L1 comprises the amino acid sequence of RSSQSIVHSNGNTYLE (SEQ ID NO: 40), the CDR L2 comprises the amino acid sequence of KVSNRFS (SEQ ID NO: 41), the CDR L3 comprises the amino acid sequence of FQGSHVPFT (SEQ ID NO: 42), the CDR H1 comprises the amino acid sequence of NYLIE (SEQ ID NO: 43), the CDR H2 comprises the amino acid sequence of LIYPGSGGTNYNEKFKG (SEQ ID NO: 44), and the CDR H3 comprises the amino acid sequence of IYYGNRDYGMDY (SEQ ID NO: 45).

16. The method of claim 10, wherein the antibody comprises a light chain variable region VL comprising the amino acid sequence of SEQ ID NO: 25 and a heavy chain variable region VH comprising the amino acid sequence of SEQ ID NO: 29.

* * * * *

SEQUENCE LISTING

<160> NUMBER OF SEQ ID NOS: 53

<210> SEQ ID NO 1
<211> LENGTH: 383
<212> TYPE: PRT
<213> ORGANISM: Homo sapiens

<400> SEQUENCE: 1

Met Gly Leu Gly Pro Val Phe Leu Leu Ala Gly Ile Phe Pro Phe
1               5                   10                  15

Ala Pro Pro Gly Ala Ala Glu Pro His Ser Leu Arg Tyr Asn Leu
                20                  25                  30

Thr Val Leu Ser Trp Asp Gly Ser Val Gln Ser Gly Phe Leu Thr Glu
            35                  40                  45

Val His Leu Asp Gly Gln Pro Phe Leu Arg Cys Asp Arg Gln Lys Cys
        50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
            100                 105                 110

Leu Gln Glu Ile Arg Val Cys Glu Ile His Glu Asp Asn Ser Thr Arg
        115                 120                 125

Ser Ser Gln His Phe Tyr Tyr Asp Gly Glu Leu Phe Leu Ser Gln Asn
            130                 135                 140

Leu Glu Thr Lys Glu Trp Thr Met Pro Gln Ser Ser Arg Ala Gln Thr
145                 150                 155                 160

Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
            180                 185                 190

Arg Tyr Leu Lys Ser Gly Val Val Leu Arg Arg Thr Val Pro Pro Met
        195                 200                 205

Val Asn Val Thr Arg Ser Glu Ala Ser Glu Gly Asn Ile Thr Val Thr
    210                 215                 220

Cys Arg Ala Ser Gly Phe Tyr Pro Trp Asn Ile Thr Leu Ser Trp Arg
225                 230                 235                 240

Gln Asp Gly Val Ser Leu Ser His Asp Thr Gln Gln Trp Gly Asp Val
                245                 250                 255

Leu Pro Asp Gly Asn Gly Thr Tyr Gln Thr Trp Val Ala Thr Arg Ile
            260                 265                 270

Cys Gln Gly Glu Glu Gln Arg Phe Thr Cys Tyr Met Glu His Ser Gly
        275                 280                 285

Asn His Ser Thr His Pro Val Pro Ser Gly Lys Val Leu Val Leu Gln
    290                 295                 300

Ser His Trp Gln Thr Phe His Val Ser Ala Val Ala Ala Ala Ala Ile
305                 310                 315                 320

Phe Val Ile Ile Ile Phe Tyr Val Arg Cys Cys Lys Lys Lys Thr Ser
                325                 330                 335

Ala Ala Glu Gly Pro Glu Leu Val Ser Leu Gln Val Leu Asp Gln His
            340                 345                 350

Pro Val Gly Thr Ser Asp His Arg Asp Ala Thr Gln Leu Gly Phe Gln
        355                 360                 365

Pro Leu Met Ser Asp Leu Gly Ser Thr Gly Ser Thr Glu Gly Ala
    370                 375                 380

<210> SEQ ID NO 2
<211> LENGTH: 383
<212> TYPE: PRT
<213> ORGANISM: Homo sapiens

<400> SEQUENCE: 2

Met Gly Leu Gly Arg Val Leu Leu Phe Leu Ala Val Ala Phe Pro Phe
1               5                   10                  15

Ala Pro Pro Ala Ala Ala Glu Pro His Ser Leu Arg Tyr Asn Leu
            20                  25                  30

Met Val Leu Ser Gln Asp Glu Ser Val Gln Ser Gly Phe Leu Ala Glu
        35                  40                  45

Gly His Leu Asp Gly Gln Pro Phe Leu Arg Tyr Asp Arg Gln Lys Arg
    50                  55                  60

Arg Ala Lys Pro Gln Gly Gln Trp Ala Glu Asp Val Leu Gly Ala Lys
65                  70                  75                  80

Thr Trp Asp Thr Glu Thr Glu Asp Leu Thr Glu Asn Gly Gln Asp Leu
                85                  90                  95

Arg Arg Thr Leu Thr His Ile Lys Asp Gln Lys Gly Gly Leu His Ser
            100                 105                 110

Leu Gln Glu Ile Arg Val Cys Glu Ile His Glu Asp Ser Ser Thr Arg
        115                 120                 125

Gly Ser Arg His Phe Tyr Tyr Asp Gly Glu Leu Phe Leu Ser Gln Asn
    130                 135                 140

Leu Glu Thr Gln Glu Ser Thr Val Pro Gln Ser Ser Arg Ala Gln Thr
145                 150                 155                 160

Leu Ala Met Asn Val Thr Asn Phe Trp Lys Glu Asp Ala Met Lys Thr
                165                 170                 175

Lys Thr His Tyr Arg Ala Met Gln Ala Asp Cys Leu Gln Lys Leu Gln
            180                 185                 190

Arg Tyr Leu Lys Ser Gly Val Ala Ile Arg Arg Thr Val Pro Pro Met
        195                 200                 205

Val Asn Val Thr Cys Ser Glu Val Ser Glu Gly Asn Ile Thr Val Thr
    210                 215                 220

Cys Arg Ala Ser Ser Phe Tyr Pro Arg Asn Ile Thr Leu Thr Trp Arg
225                 230                 235                 240

Gln Asp Gly Val Ser Leu Ser His Asn Thr Gln Gln Trp Gly Asp Val
                245                 250                 255

Leu Pro Asp Gly Asn Gly Thr Tyr Gln Thr Trp Val Ala Thr Arg Ile
            260                 265                 270

Arg Gln Gly Glu Glu Gln Arg Phe Thr Cys Tyr Met Glu His Ser Gly
        275                 280                 285

Asn His Gly Thr His Pro Val Pro Ser Gly Lys Val Leu Val Leu Gln
    290                 295                 300

Ser Gln Arg Thr Asp Phe Pro Tyr Val Ser Ala Ala Met Pro Cys Phe
305                 310                 315                 320

Val Ile Ile Ile Ile Leu Cys Val Pro Cys Cys Lys Lys Lys Thr Ser
                325                 330                 335

Ala Ala Glu Gly Pro Glu Leu Val Ser Leu Gln Val Leu Asp Gln His
            340                 345                 350

Pro Val Gly Thr Gly Asp His Arg Asp Ala Ala Gln Leu Gly Phe Gln
        355                 360                 365

```
Pro Leu Met Ser Ala Thr Gly Ser Thr Gly Ser Thr Glu Gly Ala
    370                 375                 380
```

<210> SEQ ID NO 3
<211> LENGTH: 93
<212> TYPE: PRT
<213> ORGANISM: Homo sapiens

<400> SEQUENCE: 3

```
Val Pro Pro Met Val Asn Val Thr Arg Ser Glu Ala Ser Glu Gly Asn
1               5                   10                  15

Ile Thr Val Thr Cys Arg Ala Ser Gly Phe Tyr Pro Trp Asn Ile Thr
            20                  25                  30

Leu Ser Trp Arg Gln Asp Gly Val Ser Leu Ser His Asp Thr Gln Gln
        35                  40                  45

Trp Gly Asp Val Leu Pro Asp Gly Asn Gly Thr Tyr Gln Thr Trp Val
    50                  55                  60

Ala Thr Arg Ile Cys Gln Gly Glu Glu Gln Arg Phe Thr Cys Tyr Met
65                  70                  75                  80

Glu His Ser Gly Asn His Ser Thr His Pro Val Pro Ser
                85                  90
```

<210> SEQ ID NO 4
<211> LENGTH: 93
<212> TYPE: PRT
<213> ORGANISM: Homo sapiens

<400> SEQUENCE: 4

```
Val Pro Pro Met Val Asn Val Thr Cys Ser Glu Val Ser Glu Gly Asn
1               5                   10                  15

Ile Thr Val Thr Cys Arg Ala Ser Ser Phe Tyr Pro Arg Asn Ile Thr
            20                  25                  30

Leu Thr Trp Arg Gln Asp Gly Val Ser Leu Ser His Asn Thr Gln Gln
        35                  40                  45

Trp Gly Asp Val Leu Pro Asp Gly Asn Gly Thr Tyr Gln Thr Trp Val
    50                  55                  60

Ala Thr Arg Ile Arg Gln Gly Glu Glu Gln Arg Phe Thr Cys Tyr Met
65                  70                  75                  80

Glu His Ser Gly Asn His Gly Thr His Pro Val Pro Ser
                85                  90
```

<210> SEQ ID NO 5
<211> LENGTH: 1365
<212> TYPE: DNA
<213> ORGANISM: Homo sapiens

<400> SEQUENCE: 5

```
cactgcttga gccgctgaga gggtggcgac gtcggggcca tggggctggg cccggtcttc      60
ctgcttctgg ctggcatctt ccctttttgca cctccgggag ctgctgctga gccccacagt    120
cttcgttata acctcacggt gctgtcctgg gatggatctg tgcagtcagg gtttctcact    180
gaggtacatc tggatggtca gcccttcctg cgctgtgaca gcagaaatg cagggcaaag    240 ccccagggac agtgggcaga agatgtcctg ggaaataaga catgggacag agagaccaga    300
gacttgacag ggaacggaaa ggacctcagg atgaccctgg ctcatatcaa ggaccagaaa    360
gaaggcttgc attccctcca ggagattagg gtctgtgaga tccatgaaga caacagcacc    420
aggagctccc agcatttcta ctacgatggg agctcttcc tctcccaaaa cctggagact    480
```

```
aaggaatgga caatgcccca gtcctccaga gctcagacct tggccatgaa cgtcaggaat      540
ttcttgaagg aagatgccat gaagaccaag acacactatc acgctatgca tgcagactgc      600
ctgcaggaac tacggcgata tctaaaatcc ggcgtagtcc tgaggagaac agtgcccccc      660
atggtgaatg tcacccgcag cgaggcctca gagggcaaca ttaccgtgac atgcagggct      720
tctggcttct atccctggaa tatcacactg agctggcgtc aggatggggt atctttgagc      780
cacgacaccc agcagtgggg ggatgtcctg cctgatggga atggaaccta ccagacctgg      840
gtggccacca ggatttgcca aggagaggag cagaggttca cctgctacat ggaacacagc      900
gggaatcaca gcactcaccc tgtgccctct gggaaagtgc tggtgcttca gagtcattgg      960
cagacattcc atgtttctgc tgttgctgct gctgctattt ttgttattat tattttctat     1020
gtccgttgtt gtaagaagaa acatcagct gcagagggtc cagagctcgt gagcctgcag      1080
gtcctggatc aacacccagt tgggacgagt gaccacaggg atgccacaca gctcggattt      1140
cagcctctga tgtcagatct tgggtccact ggctccactg agggcgccta gactctacag      1200
ccaggcagct gggattcaat tccctgcctg gatctcacga gcactttccc tcttggtgcc     1260
tcagtttcct gacctatgaa acagagaaaa taaaagcact tatttattgt tgttggaggc     1320
tgcaaaatgt tagtagatat gaggcgtttg cagctgtacc atatt                     1365

<210> SEQ ID NO 6
<211> LENGTH: 2380
<212> TYPE: DNA
<213> ORGANISM: Homo sapiens

<400> SEQUENCE: 6
gggccatggg gctgggccgg gtcctgctgt ttctggccgt cgccttccct tttgcacccc       60
cggcagccgc cgctgagccc cacagtcttc gttacaacct catggtgctg tcccaggatg      120
aatctgtgca gtcagggttt ctcgctgagg acatctgga tggtcagccc ttcctgcgct       180
atgacaggca gaaacgcagg gcaaagcccc agggacagtg ggcagaagat gtcctgggag      240
ctaagacctg ggacacagag accgaggact tgacagagaa tgggcaagac ctcaggagga      300
ccctgactca tatcaaggac cagaaaggag gcttgcattc cctccaggag attagggtct      360
gtgagatcca tgaagacagc agcaccaggg gctcccggca tttctactac gatggggagc      420
tcttcctctc ccaaaacctg gagactcaag aatcgacagt gccccagtcc tccagagctc      480
agaccttggc tatgaacgtc acaaatttct ggaaggaaga tgccatgaag accaagacac      540
actatcgcgc tatgcaggca gactgcctgc agaaaactac gcgatatctg aaatccgggg      600
tggccatcag gagaacagtg cccccatgg tgaatgtcac ctgcagcgag gtctcagagg       660
gcaacatcac cgtgacatgc agggcttcca gcttctatcc ccggaatatc acactgacct      720
ggcgtcagga tggggtatct ttgagccaca cacccagca gtgggggat gtcctgcctg        780 atgggaatgg aacctaccag acctgggtgg ccaccaggat cgccaagga gaggagcaga      840 ggttcacctg ctacatggaa cacagcggga tcacggcac tcaccctgtg ccctctggga      900
aggtgctggt gcttcagagt caacggacag acttcccata tgtttctgct gctatgccat      960
gttttgttat tattattatt ctctgtgtcc cttgttgcaa gaagaaaca tcagcggcag      1020 agggtccaga gcttgtgagc ctgcaggtcc tggatcaaca cccagttggg acaggagacc     1080
acagggatgc agcacagctg ggatttcagc ctctgatgtc agctactggg tccactggtt      1140
ccactgaggg cgcctagact ctacagccag gcggccagga ttcaactccc tgcctggatc      1200
```

```
tcaccagcac tttccctctg tttcctgacc tatgaaacag aaaataacat cacttattta   1260
ttgttgttgg atgctgcaaa gtgttagtag gtatgaggtg tttgctgctc tgccacgtag   1320
agagccagca aagggatcat gaccaactca acattccatt ggaggctata tgatcaaaca   1380
gcaaattgtt tatcatgaat gcaggatgtg ggcaaactca cgactgctcc tgccaacaga   1440
aggtttgctg agggcattca ctccatggtg ctcattggag ttatctactg ggtcatctag   1500
agcctattgt ttgaggaatg cagtcttaca agcctactct ggacccagca gctgactcct   1560
tcttccaccc ctcttcttgc tatctcctat accaataaat acgaagggct gtggaagatc   1620
agagcccttg ttcacgagaa gcaagaagcc ccctgacccc ttgttccaaa tatactcttt   1680
tgtctttctc tttattccca cgttcgccct ttgttcagtc aatacagggg ttgtggggcc   1740
cttaacagtg ccatattaat tggtatcatt atttctgttg ttttttgtttt tgttttttgtt 1800
tttgtttttg agacagagtc tcactcgtca cccaggctgc agttcactgg tgtgatctca   1860
gctcactgca acctctgcct cccaggttca agcacttctc gtacctcaga ctcccgatag   1920
ctgggattac agacaggcac caccacaccc agctaatttt tgtattttttt gtagagacgg   1980
ggtttcgcca gttgaccag cccagtttca aactcctgac ctcaggtgat ctgcctgcct   2040
tggcatccca aagtgctggg attacaagaa tgagccaccg tgcctggcct attttattat   2100
attgtaatat attttattat attagccacc atgcctgtcc tattttctta tgttttaata   2160
tattttaata tattacatgt gcagtaatta ggattatcatg ggtgaacttt atgagtgagt   2220
atcttggtga tgactcctcc tgaccagccc aggaccagct ttcttgtcac cttgaggtcc   2280
cctcgccccg tcacaccgtt atcgattact ctgtgtctac tattatgtgt gcataaattta   2340
taccgtaaat gtttactctt taaataaaaa aaaaaaaaaa                         2380

<210> SEQ ID NO 7
<211> LENGTH: 274
<212> TYPE: PRT
<213> ORGANISM: Homo sapiens

<400> SEQUENCE: 7

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
```

165                 170                 175
Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 8
<211> LENGTH: 274
<212> TYPE: PRT
<213> ORGANISM: Homo sapiens

<400> SEQUENCE: 8

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr Leu Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val

<210> SEQ ID NO 9
<211> LENGTH: 274
<212> TYPE: PRT
<213> ORGANISM: Homo sapiens

<400> SEQUENCE: 9

Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Met Pro Gln Ser Ser Arg Ala Gln Thr Leu Ala Met Asn Ile Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 10
<211> LENGTH: 274
<212> TYPE: PRT
<213> ORGANISM: Homo sapiens

<400> SEQUENCE: 10

Glu Pro His Ser Leu Pro Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Tyr Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
 50                  55                  60

Asp Leu Thr Gly Asn Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Glu Glu Trp Thr
            115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser

<210> SEQ ID NO 11
<211> LENGTH: 274
<212> TYPE: PRT
<213> ORGANISM: Homo sapiens

<400> SEQUENCE: 11

Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
            20                  25                  30

Phe Leu Arg Tyr Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
 50                  55                  60

Asp Leu Thr Gly Asn Gly Lys Asp Leu Arg Met Thr Leu Ala His Ile
 65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
                100                 105                 110

Asp Gly Glu Leu Phe Leu Ser Gln Asn Leu Glu Thr Glu Glu Trp Thr
            115                 120                 125

```
Val Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Glu Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Ser Phe Tyr
        195                 200                 205

Pro Arg Asn Ile Thr Leu Thr Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
                260                 265                 270

Pro Ser

<210> SEQ ID NO 12
<211> LENGTH: 274
<212> TYPE: PRT
<213> ORGANISM: Homo sapiens

<400> SEQUENCE: 12

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
210                 215                 220
```

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
            245                 250                 255

Phe Thr Cys Tyr Met Glu His Ser Gly Asn His Ser Thr His Pro Val
            260                 265                 270

Pro Ser

<210> SEQ ID NO 13
<211> LENGTH: 274
<212> TYPE: PRT
<213> ORGANISM: Homo sapiens

<400> SEQUENCE: 13

Glu Pro His Ser Leu Arg Tyr Asn Leu Thr Val Leu Ser Trp Asp Gly
1               5                   10                  15

Ser Val Gln Ser Gly Phe Leu Ala Glu Val His Leu Asp Gly Gln Pro
                20                  25                  30

Phe Leu Arg Cys Asp Arg Gln Lys Cys Arg Ala Lys Pro Gln Gly Gln
            35                  40                  45

Trp Ala Glu Asp Val Leu Gly Asn Lys Thr Trp Asp Arg Glu Thr Arg
50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Glu Glu Trp Thr
        115                 120                 125

Met Pro Gln Ser Ser Arg Ala Gln Thr Leu Ala Met Asn Val Arg Asn
130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
            245                 250                 255

Phe Thr Cys Tyr Met Glu His Ser Gly Asn His Ser Thr His Pro Val
            260                 265                 270

Pro Ser

<210> SEQ ID NO 14
<211> LENGTH: 276
<212> TYPE: PRT
<213> ORGANISM: Homo sapiens

<400> SEQUENCE: 14

Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
            100                 105                 110

Asp Gly Glu Leu Phe Leu Ser Gln Asn Leu Glu Thr Lys Glu Trp Thr
        115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
        195                 200                 205

Pro Trp Asn Ile Thr Leu Ser Trp Arg Gln Asp Gly Val Ser Leu Ser
    210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
            260                 265                 270

Pro Ser Gly Lys
        275

<210> SEQ ID NO 15
<211> LENGTH: 274
<212> TYPE: PRT
<213> ORGANISM: Homo sapiens

<400> SEQUENCE: 15

Glu Pro His Ser Leu Arg Tyr Asn Leu Met Val Leu Ser Gln Asp Glu
1               5                   10                  15

Ser Val Gln Ser Gly Phe Leu Ala Glu Gly His Leu Asp Gly Gln Pro
            20                  25                  30

Phe Leu Arg Tyr Asp Arg Gln Lys Arg Arg Ala Lys Pro Gln Gly Gln
        35                  40                  45

Trp Ala Glu Asp Val Leu Gly Ala Lys Thr Trp Asp Thr Glu Thr Glu
    50                  55                  60

Asp Leu Thr Glu Asn Gly Gln Asp Leu Arg Arg Thr Leu Thr His Ile
65                  70                  75                  80

Lys Asp Gln Lys Gly Gly Leu His Ser Leu Gln Glu Ile Arg Val Cys

```
            85              90                  95
Glu Ile His Glu Asp Ser Ser Thr Arg Gly Ser Arg His Phe Tyr Tyr
            100                 105                 110

Asp Gly Glu Leu Phe Leu Ser Gln Asn Leu Glu Thr Gln Glu Ser Thr
            115                 120                 125

Val Pro Gln Ser Ser Arg Ala Gln Thr Leu Ala Met Asn Val Thr Asn
            130                 135                 140

Phe Trp Lys Glu Asp Ala Met Lys Thr Lys Thr His Tyr Arg Ala Met
145                 150                 155                 160

Gln Ala Asp Cys Leu Gln Lys Leu Gln Arg Tyr Leu Lys Ser Gly Val
                165                 170                 175

Ala Ile Arg Arg Thr Val Pro Pro Met Val Asn Val Thr Cys Ser Glu
                180                 185                 190

Val Ser Glu Gly Asn Ile Thr Val Thr Cys Arg Ala Ser Ser Phe Tyr
                195                 200                 205

Pro Arg Asn Ile Thr Leu Thr Trp Arg Gln Asp Gly Val Ser Leu Ser
                210                 215                 220

His Asn Thr Gln Gln Trp Gly Asp Val Leu Pro Asp Gly Asn Gly Thr
225                 230                 235                 240

Tyr Gln Thr Trp Val Ala Thr Arg Ile Arg Gln Gly Glu Glu Gln Arg
                245                 250                 255

Phe Thr Cys Tyr Met Glu His Ser Gly Asn His Gly Thr His Pro Val
                260                 265                 270

Pro Ser

<210> SEQ ID NO 16
<211> LENGTH: 275
<212> TYPE: PRT
<213> ORGANISM: Homo sapiens

<400> SEQUENCE: 16

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
                20                  25                  30

Leu Arg Tyr Asp Arg Gln Lys Arg Arg Ala Lys Pro Gln Gly Gln Trp
            35                  40                  45

Ala Glu Asp Val Leu Gly Ala Lys Thr Trp Asp Thr Glu Thr Glu Asp
        50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asp
                100                 105                 110

Gly Glu Leu Phe Leu Ser Gln Asn Leu Glu Thr Gln Glu Ser Thr Val
            115                 120                 125

Pro Gln Ser Ser Arg Ala Gln Thr Leu Ala Met Asn Val Thr Asn Phe
        130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Leu Pro Pro Met Val Asn Val Ile
                165                 170                 175

Cys Ser Glu Val Ser Glu Gly Asn Ile Thr Val Thr Cys Arg Ala Ser
```

```
            180                 185                 190
Ser Phe Tyr Pro Arg Asn Ile Thr Leu Thr Trp Arg Gln Asp Gly Val
                195                 200                 205

Ser Leu Ser His Asn Thr Gln Gln Trp Gly Asp Val Leu Pro Asp Gly
        210                 215                 220

Asn Gly Thr Tyr Gln Thr Trp Val Ala Thr Arg Ile Arg Gln Gly Glu
225                 230                 235                 240

Glu Gln Arg Phe Thr Cys Tyr Met Glu His Ser Gly Asn His Gly Thr
                245                 250                 255

His Pro Val Pro Ser Gly Lys Ala Leu Val Leu Gln Ser Gln Arg Thr
            260                 265                 270

Asp Phe Pro
        275

<210> SEQ ID NO 17
<211> LENGTH: 273
<212> TYPE: PRT
<213> ORGANISM: Homo sapiens

<400> SEQUENCE: 17

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

Ala Glu Asp Val Leu Gly Ala Glu Thr Trp Asp Thr Glu Thr Glu Asp
    50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Met His Glu Asp Ser Ser Thr Arg Gly Ser Arg His Phe Tyr Tyr Asn
            100                 105                 110

Gly Glu Leu Phe Leu Ser Gln Asn Leu Glu Thr Gln Glu Ser Thr Val
        115                 120                 125

Pro Gln Ser Ser Arg Ala Gln Thr Leu Ala Met Asn Val Thr Asn Phe
    130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
                165                 170                 175

Ile Arg Arg Thr Val Pro Pro Met Val Asn Val Thr Cys Ser Glu Val
            180                 185                 190

Ser Glu Gly Asn Ile Thr Val Thr Cys Arg Ala Ser Ser Phe Tyr Pro
        195                 200                 205

Arg Asn Ile Thr Leu Thr Trp Arg Gln Asp Gly Val Ser Leu Ser His
    210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Arg Phe
                245                 250                 255

Thr Cys Tyr Met Glu His Ser Gly Asn His Gly Thr His Pro Val Pro
            260                 265                 270
```

Ser

<210> SEQ ID NO 18
<211> LENGTH: 273
<212> TYPE: PRT
<213> ORGANISM: Homo sapiens

<400> SEQUENCE: 18

```
Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45

Ala Glu Asp Val Leu Gly Ala Lys Thr Trp Asp Thr Glu Thr Glu Asp
    50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asp
            100                 105                 110

Gly Glu Leu Phe Leu Ser Gln Asn Leu Glu Thr Gln Glu Ser Thr Val
        115                 120                 125

Pro Gln Ser Ser Arg Ala Gln Thr Leu Ala Met Asn Val Thr Asn Phe
    130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
                165                 170                 175

Ile Arg Arg Thr Val Pro Pro Met Val Asn Val Ile Cys Ser Glu Val
            180                 185                 190

Ser Glu Gly Asn Ile Thr Val Thr Cys Arg Ala Ser Ser Phe Tyr Pro
        195                 200                 205

Arg Asn Ile Thr Leu Thr Trp Arg Gln Asp Gly Val Ser Leu Ser His
    210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Arg Phe
                245                 250                 255

Thr Cys Tyr Met Glu His Ser Gly Asn His Gly Thr His Pro Val Pro
            260                 265                 270

Ser
```

<210> SEQ ID NO 19
<211> LENGTH: 273
<212> TYPE: PRT
<213> ORGANISM: Homo sapiens

<400> SEQUENCE: 19

```
Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
        35                  40                  45
```

Ala Glu Asn Val Leu Gly Ala Lys Thr Trp Asp Thr Glu Thr Glu Asp
            50                  55                  60

Leu Thr Glu Asn Gly Gln Asp Leu Arg Arg Thr Leu Thr His Ile Lys
 65                  70                  75                  80

Asp Gln Lys Gly Gly Leu His Ser Leu Gln Glu Ile Arg Val Cys Glu
                 85                  90                  95

Ile His Glu Asp Ser Ser Thr Arg Gly Ser Arg His Phe Tyr Tyr Asp
            100                 105                 110

Gly Glu Leu Phe Leu Ser Gln Asn Leu Glu Thr Gln Glu Ser Thr Val
            115                 120                 125

Pro Gln Ser Ser Arg Ala Gln Thr Leu Ala Met Asn Val Thr Asn Phe
130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
                165                 170                 175

Ile Arg Arg Thr Val Pro Pro Met Val Asn Val Thr Cys Ser Glu Val
            180                 185                 190

Ser Glu Gly Asn Ile Thr Val Thr Cys Arg Ala Ser Ser Phe Tyr Pro
            195                 200                 205

Arg Asn Ile Thr Leu Thr Trp Arg Gln Asp Gly Val Ser Leu Ser His
210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Arg Phe
                245                 250                 255

Thr Cys Tyr Met Glu His Ser Gly Asn His Gly Thr His Pro Val Pro
            260                 265                 270

Ser

<210> SEQ ID NO 20
<211> LENGTH: 273
<212> TYPE: PRT
<213> ORGANISM: Homo sapiens

<400> SEQUENCE: 20

Pro His Ser Leu Arg Tyr Asn Leu Met Val Leu Ser Gln Asp Gly Ser
 1               5                  10                  15

Val Gln Ser Gly Phe Leu Ala Glu Gly His Leu Asp Gly Gln Pro Phe
                 20                  25                  30

Leu Arg Tyr Asp Arg Gln Lys Arg Arg Ala Lys Pro Gln Gly Gln Trp
             35                  40                  45

Ala Glu Asp Val Leu Gly Ala Glu Thr Trp Asp Thr Glu Thr Glu Asp
            50                  55                  60

Leu Thr Glu Asn Gly Gln Asp Leu Arg Arg Thr Leu Thr His Ile Lys
 65                  70                  75                  80

Asp Gln Lys Gly Gly Leu His Ser Leu Gln Glu Ile Arg Val Cys Glu
                 85                  90                  95

Ile His Glu Asp Ser Ser Thr Arg Gly Ser Arg His Phe Tyr Tyr Asn
            100                 105                 110

Gly Glu Leu Phe Leu Ser Gln Asn Leu Glu Thr Gln Glu Ser Thr Val
            115                 120                 125

Pro Gln Ser Ser Arg Ala Gln Thr Leu Ala Met Asn Val Thr Asn Phe
130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
            165                 170                 175

Ile Arg Arg Thr Val Pro Pro Met Val Asn Val Thr Cys Ser Glu Val
            180                 185                 190

Ser Glu Gly Asn Ile Thr Val Thr Cys Arg Ala Ser Ser Phe Tyr Pro
            195                 200                 205

Arg Asn Ile Thr Leu Thr Trp Arg Gln Asp Gly Val Ser Leu Ser His
            210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Glu Gln Lys Phe
            245                 250                 255

Thr Cys Tyr Met Glu His Ser Gly Asn His Gly Thr His Pro Val Pro
            260                 265                 270

Ser

<210> SEQ ID NO 21
<211> LENGTH: 273
<212> TYPE: PRT
<213> ORGANISM: Homo sapiens

<400> SEQUENCE: 21

Pro His Ser Leu Arg Tyr Asn Leu Met Val Leu Ser Gln Asp Gly Ser
1               5                   10                  15

Val Gln Ser Gly Phe Leu Ala Glu Gly His Leu Asp Gly Gln Pro Phe
            20                  25                  30

Leu Arg Tyr Asp Arg Gln Lys Arg Arg Ala Lys Pro Gln Gly Gln Trp
            35                  40                  45

Ala Glu Asp Val Leu Gly Ala Glu Thr Trp Asp Thr Glu Thr Glu Asp
    50                  55                  60

Leu Thr Glu Asn Gly Gln Asp Leu Arg Arg Thr Leu Thr His Ile Lys
65                  70                  75                  80

Asp Gln Lys Gly Gly Leu His Ser Leu Gln Glu Ile Arg Val Cys Glu
                85                  90                  95

Ile His Glu Asp Ser Ser Thr Arg Gly Ser Arg His Phe Tyr Tyr Asn
            100                 105                 110

Gly Glu Leu Phe Leu Ser Gln Asn Leu Glu Thr Gln Glu Ser Thr Val
            115                 120                 125

Pro Gln Ser Ser Arg Ala Gln Thr Leu Ala Met Asn Val Thr Asn Phe
130                 135                 140

Trp Lys Glu Asp Ala Met Lys Thr Lys Thr His Tyr Arg Ala Met Gln
145                 150                 155                 160

Ala Asp Cys Leu Gln Lys Leu Gln Arg Tyr Leu Lys Ser Gly Val Ala
            165                 170                 175

Ile Arg Arg Thr Val Pro Pro Met Val Asn Val Thr Cys Ser Glu Val
            180                 185                 190

Ser Glu Gly Asn Ile Thr Val Thr Cys Arg Ala Ser Ser Phe Tyr Pro
            195                 200                 205

Arg Asn Ile Thr Leu Thr Trp Arg Gln Asp Gly Val Ser Leu Ser His
            210                 215                 220

Asn Thr Gln Gln Trp Gly Asp Val Leu Pro Asp Gly Asn Gly Thr Tyr
225                 230                 235                 240

Gln Thr Trp Val Ala Thr Arg Ile Arg Gln Gly Glu Gln Arg Phe
                245                 250                 255

Thr Cys Tyr Met Glu His Ser Gly Asn His Gly Thr His Pro Val Pro
            260                 265                 270

Ser

<210> SEQ ID NO 22
<211> LENGTH: 8
<212> TYPE: PRT
<213> ORGANISM: Homo sapiens

<400> SEQUENCE: 22

Gln Gln Trp Gly Asp Val Leu Pro
1               5

<210> SEQ ID NO 23
<211> LENGTH: 4
<212> TYPE: PRT
<213> ORGANISM: Homo sapiens

<400> SEQUENCE: 23

Gly Asp Val Leu
1

<210> SEQ ID NO 24
<211> LENGTH: 140
<212> TYPE: PRT
<213> ORGANISM: Artificial Sequence
<220> FEATURE:
<223> OTHER INFORMATION: variable light chain of antibody 5C9

<400> SEQUENCE: 24

Met Lys Leu Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
                20                  25                  30

Ser Leu Gly Asp Gln Ala Ser Ile Ser Cys Arg Ser Ser Gln Ser Ile
            35                  40                  45

Val His Ser Asn Gly Asn Thr Tyr Leu Glu Trp Tyr Leu Gln Lys Pro
        50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
                100                 105                 110

Phe Gln Gly Ser His Val Pro Phe Thr Phe Gly Ser Gly Thr Lys Leu
            115                 120                 125

Glu Ile Lys Arg Ala Asp Ala Ala Pro Thr Val Ser
        130                 135                 140

<210> SEQ ID NO 25
<211> LENGTH: 109
<212> TYPE: PRT
<213> ORGANISM: Artificial Sequence
<220> FEATURE:
<223> OTHER INFORMATION: variable light chain of antibody 5C9

<400> SEQUENCE: 25

Met Thr Gln Thr Pro Leu Ser Leu Pro Val Ser Leu Gly Asp Gln Ala

```
                1               5                   10                  15
Ser Ile Ser Cys Arg Ser Gln Ser Ile Val His Ser Asn Gly Asn
                20                  25                  30

Thr Tyr Leu Glu Trp Tyr Leu Gln Lys Pro Gly Gln Ser Pro Lys Leu
            35                  40                  45

Leu Ile Tyr Lys Val Ser Asn Arg Phe Ser Gly Val Pro Asp Arg Phe
            50                  55                  60

Ser Gly Ser Gly Ser Gly Thr Asp Phe Thr Leu Lys Ile Ser Arg Val
 65                 70                  75                  80

Glu Ala Glu Asp Leu Gly Val Tyr Tyr Cys Phe Gln Gly Ser His Val
                85                  90                  95

Pro Phe Thr Phe Gly Ser Gly Thr Lys Leu Glu Ile Lys
                100                 105
```

<210> SEQ ID NO 26
<211> LENGTH: 393
<212> TYPE: DNA
<213> ORGANISM: Artificial Sequence
<220> FEATURE:
<223> OTHER INFORMATION: variable light chain of antibody 5C9

<400> SEQUENCE: 26

```
atgaagttgc ctgttaggct gttggtgctg atgttctgga ttcctgcttc cagcagtgat      60
gttttgatga cccaaactcc actctccctg cctgtcagtc ttggagatca agcctccatc     120
tcttgcagat ctagtcagag cattgtacat agtaatggaa acacctattt agaatggtac     180
ctgcagaaac aggccagtc tccaaagctc ctgatctaca agtttccaa ccgattttct       240
ggggtcccag acaggttcag tggcagtgga tcagggacag atttcacact caagatcagc    300
agagtggagg ctgaggatct gggagtttat tactgctttc aaggttcaca tgttccattc    360
acgttcggct cggggacaaa gttggaaata aaa                                 393
```

<210> SEQ ID NO 27
<211> LENGTH: 327
<212> TYPE: DNA
<213> ORGANISM: Artificial Sequence
<220> FEATURE:
<223> OTHER INFORMATION: variable light chain of antibody 5C9

<400> SEQUENCE: 27

```
atgacccaaa ctccactctc cctgcctgtc agtcttggag atcaagcctc catctcttgc      60
agatctagtc agagcattgt acatagtaat ggaaacacct atttagaatg gtacctgcag    120
aaaccaggcc agtctccaaa gctcctgatc tacaaagttt ccaaccgatt ttctggggtc    180
ccagacaggt tcagtggcag tggatcaggg acagatttca cactcaagat cagcagagtg    240
gaggctgagg atctgggagt ttattactgc tttcaaggtt cacatgttcc attcacgttc    300
ggctcgggga caaagttgga aataaaa                                         327
```

<210> SEQ ID NO 28
<211> LENGTH: 160
<212> TYPE: PRT
<213> ORGANISM: Artificial Sequence
<220> FEATURE:
<223> OTHER INFORMATION: variable heavy chain of antibody 5C9

<400> SEQUENCE: 28

```
Met Glu Trp Ser Gly Val Phe Ile Phe Leu Leu Ser Val Thr Ala Gly
 1               5                  10                  15
```

Val His Ser Gln Val Gln Leu Gln Gln Ser Gly Ala Glu Leu Val Arg
            20                  25                  30

Pro Gly Thr Ser Val Lys Val Ser Cys Lys Ala Ser Gly Tyr Ala Phe
        35                  40                  45

Thr Asn Tyr Leu Ile Glu Trp Val Lys Gln Arg Pro Gly Gln Gly Leu
    50                  55                  60

Glu Trp Ile Gly Leu Ile Tyr Pro Gly Ser Gly Thr Asn Tyr Asn
65                  70                  75                  80

Glu Lys Phe Lys Gly Lys Ala Thr Leu Thr Ala Asp Lys Ser Ser Ser
                85                  90                  95

Thr Ala Tyr Met Gln Leu Ser Ser Leu Thr Ser Asp Asp Ser Ala Val
            100                 105                 110

Tyr Phe Cys Ala Arg Ile Tyr Tyr Gly Asn Arg Asp Tyr Gly Met Asp
        115                 120                 125

Tyr Trp Gly Gln Gly Thr Ser Val Thr Val Ser Ser Ala Lys Thr Thr
    130                 135                 140

Pro Pro Ser Val Tyr Pro Leu Ala Pro Gly Cys Gly Asp Thr Thr Gly
145                 150                 155                 160

<210> SEQ ID NO 29
<211> LENGTH: 123
<212> TYPE: PRT
<213> ORGANISM: Artificial Sequence
<220> FEATURE:
<223> OTHER INFORMATION: variable heavy chain of antibody 5C9

<400> SEQUENCE: 29

Gln Val Gln Leu Gln Gln Ser Gly Ala Glu Leu Val Arg Pro Gly Thr
1               5                   10                  15

Ser Val Lys Val Ser Cys Lys Ala Ser Gly Tyr Ala Phe Thr Asn Tyr
            20                  25                  30

Leu Ile Glu Trp Val Lys Gln Arg Pro Gly Gln Gly Leu Glu Trp Ile
        35                  40                  45

Gly Leu Ile Tyr Pro Gly Ser Gly Gly Thr Asn Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Ile Tyr Tyr Gly Asn Arg Asp Tyr Gly Met Asp Tyr Trp Gly
            100                 105                 110

Gln Gly Thr Ser Val Thr Val Ser Ser Ala Lys
        115                 120

<210> SEQ ID NO 30
<211> LENGTH: 426
<212> TYPE: DNA
<213> ORGANISM: Artificial Sequence
<220> FEATURE:
<223> OTHER INFORMATION: variable heavy chain of antibody 5C9

<400> SEQUENCE: 30
atggaatgga gcggagtctt tatctttctc ctgtcagtaa ctgcaggtgt tcactcccag      60
gtccagctgc agcagtctgg agctgagctg gtaaggcctg ggacttcagt gaaggtgtcc    120
tgcaaggctt ctggatacgc cttcactaat tacttgatag agtgggtaaa gcagaggcct    180
ggacagggcc ttgagtggat tggactgatt tatcctggaa gtggtggtac taactacaat    240

```
gagaaattca agggcaaggc aacactgact gcagacaaat cctccagcac tgcctacatg    300
cagctcagca gcctgacatc tgatgactct gcggtttatt tctgtgcaag aatctactat    360
ggtaacaggg actatggtat ggactactgg ggtcaaggaa cctcagtcac cgtctcctca    420
gccaaa                                                               426

<210> SEQ ID NO 31
<211> LENGTH: 369
<212> TYPE: DNA
<213> ORGANISM: Artificial Sequence
<220> FEATURE:
<223> OTHER INFORMATION: variable heavy chain of antibody 5C9

<400> SEQUENCE: 31
caggtccagc tgcagcagtc tggagctgag ctggtaaggc ctgggacttc agtgaaggtg     60
tcctgcaagg cttctggata cgccttcact aattacttga tagagtgggt aaagcagagg    120
cctggacagg gccttgagtg gattggactg atttatcctg gaagtggtgg tactaactac    180
aatgagaaat tcaagggcaa ggcaacactg actgcagaca atcctccag cactgcctac    240 atgcagctca gcagcctgac atctgatgac tctgcggttt atttctgtgc aagaatctac    300
tatggtaaca gggactatgg tatggactac tggggtcaag gaacctcagt caccgtctcc    360
tcagccaaa                                                            369

<210> SEQ ID NO 32
<211> LENGTH: 87
<212> TYPE: PRT
<213> ORGANISM: Artificial Sequence
<220> FEATURE:
<223> OTHER INFORMATION: Synthetic construct

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Trp Val
            20                  25                  30

Arg Gln Ala Pro Gly Gln Gly Leu Glu Trp Met Gly Arg Val Thr Ile
        35                  40                  45

Thr Ala Asp Thr Ser Thr Ser Thr Ala Tyr Met Glu Leu Ser Ser Leu
    50                  55                  60

Arg Ser Glu Asp Thr Ala Val Tyr Tyr Cys Ala Arg Trp Gly Gln Gly
65                  70                  75                  80

Thr Leu Val Thr Val Ser Ser
                85

<210> SEQ ID NO 33
<211> LENGTH: 87
<212> TYPE: PRT
<213> ORGANISM: Artificial Sequence
<220> FEATURE:
<223> OTHER INFORMATION: Synthetic construct

<400> SEQUENCE: 33

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Trp Ile
            20                  25                  30

Arg Gln Pro Pro Gly Lys Gly Leu Glu Trp Ile Gly Arg Val Thr Ile
        35                  40                  45
```

```
Ser Val Asp Thr Ser Lys Asn Gln Phe Ser Leu Lys Leu Ser Ser Val
 50                  55                  60

Thr Ala Ala Asp Thr Ala Val Tyr Tyr Cys Ala Arg Trp Gly Gln Gly
 65                  70                  75                  80

Thr Leu Val Thr Val Ser Ser
                 85

<210> SEQ ID NO 34
<211> LENGTH: 87
<212> TYPE: PRT
<213> ORGANISM: Artificial Sequence
<220> FEATURE:
<223> OTHER INFORMATION: Synthetic construct

<400> SEQUENCE: 34

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Trp Val
                 20                  25                  30

Arg Gln Ala Pro Gly Lys Gly Leu Glu Trp Val Ser Arg Phe Thr Ile
             35                  40                  45

Ser Arg Asp Asn Ser Lys Asn Thr Leu Tyr Leu Gln Met Asn Ser Leu
 50                  55                  60

Arg Ala Glu Asp Thr Ala Val Tyr Tyr Cys Ala Arg Trp Gly Gln Gly
 65                  70                  75                  80

Thr Leu Val Thr Val Ser Ser
                 85

<210> SEQ ID NO 35
<211> LENGTH: 87
<212> TYPE: PRT
<213> ORGANISM: Artificial Sequence
<220> FEATURE:
<223> OTHER INFORMATION: Synthetic construct

<400> SEQUENCE: 35

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Trp Val
                 20                  25                  30

Arg Gln Ala Pro Gly Gln Gly Leu Glu Trp Met Gly Arg Phe Val Phe
             35                  40                  45

Ser Leu Asp Thr Ser Val Ser Thr Ala Tyr Leu Gln Ile Ser Ser Leu
 50                  55                  60

Lys Ala Glu Asp Thr Ala Val Tyr Tyr Cys Ala Arg Trp Gly Gln Gly
 65                  70                  75                  80

Thr Ser Leu Thr Val Ser Ser
                 85

<210> SEQ ID NO 36
<211> LENGTH: 80
<212> TYPE: PRT
<213> ORGANISM: Artificial Sequence
<220> FEATURE:
<223> OTHER INFORMATION: Synthetic construct

<400> SEQUENCE: 36

Asp Ile Gln Met Thr Gln Ser Pro Ser Ser Leu Ser Ala Ser Val Gly
 1               5                  10                  15

Asp Arg Val Thr Ile Thr Cys Trp Tyr Gln Gln Lys Pro Gly Lys Ala
```

```
                    20                  25                  30

Pro Lys Leu Leu Ile Tyr Gly Val Pro Ser Arg Phe Ser Gly Ser Gly
            35                  40                  45

Ser Gly Thr Asp Phe Thr Leu Thr Ile Ser Ser Leu Gln Pro Glu Asp
        50                  55                  60

Phe Ala Thr Tyr Tyr Cys Phe Gly Gln Gly Thr Lys Val Glu Ile Lys
65                  70                  75                  80

<210> SEQ ID NO 37
<211> LENGTH: 80
<212> TYPE: PRT
<213> ORGANISM: Artificial Sequence
<220> FEATURE:
<223> OTHER INFORMATION: Synthetic construct

<400> SEQUENCE: 37

Asp Ile Val Met Thr Gln Ser Pro Leu Ser Leu Pro Val Thr Pro Gly
1               5                   10                  15

Glu Pro Ala Ser Ile Ser Cys Trp Tyr Leu Gln Lys Pro Gly Gln Ser
                20                  25                  30

Pro Gln Leu Leu Ile Tyr Gly Val Pro Asp Arg Phe Ser Gly Ser Gly
            35                  40                  45

Ser Gly Thr Asp Phe Thr Leu Lys Ile Ser Arg Val Glu Ala Glu Asp
        50                  55                  60

Val Gly Val Tyr Tyr Cys Phe Gly Gln Gly Thr Lys Val Glu Ile Lys
65                  70                  75                  80

<210> SEQ ID NO 38
<211> LENGTH: 80
<212> TYPE: PRT
<213> ORGANISM: Artificial Sequence
<220> FEATURE:
<223> OTHER INFORMATION: Synthetic construct

<400> SEQUENCE: 38

Glu Ile Val Leu Thr Gln Ser Pro Gly Thr Leu Ser Leu Ser Pro Gly
1               5                   10                  15

Glu Arg Ala Thr Leu Ser Cys Trp Tyr Gln Gln Lys Pro Gly Gln Ala
                20                  25                  30

Pro Arg Leu Leu Ile Tyr Gly Ile Pro Asp Arg Phe Ser Gly Ser Gly
            35                  40                  45

Ser Gly Thr Asp Phe Thr Leu Thr Ile Ser Arg Leu Glu Pro Glu Asp
        50                  55                  60

Phe Ala Val Tyr Tyr Cys Phe Gly Gln Gly Thr Lys Val Glu Ile Lys
65                  70                  75                  80

<210> SEQ ID NO 39
<211> LENGTH: 79
<212> TYPE: PRT
<213> ORGANISM: Artificial Sequence
<220> FEATURE:
<223> OTHER INFORMATION: Synthetic construct

<400> SEQUENCE: 39

Asp Ile Val Met Thr Gln Ser Pro Asp Ser Leu Ala Val Ser Leu Gly
1               5                   10                  15

Glu Arg Ala Thr Ile Asn Cys Trp Tyr Gln Gln Lys Pro Gly Gln Pro
                20                  25                  30

Pro Lys Leu Leu Ile Tyr Gly Val Pro Asp Arg Phe Ser Gly Ser Gly
            35                  40                  45
```

```
Ser Gly Thr Asp Phe Thr Leu Thr Ile Ser Ser Leu Gln Ala Glu Asp
        50                  55                  60

Val Ala Val Tyr Tyr Cys Phe Gly Gln Gly Thr Lys Val Glu Ile
 65                  70                  75

<210> SEQ ID NO 40
<211> LENGTH: 16
<212> TYPE: PRT
<213> ORGANISM: Artificial Sequence
<220> FEATURE:
<223> OTHER INFORMATION: CDR L1 of antibody 5C9

<400> SEQUENCE: 40

Arg Ser Ser Gln Ser Ile Val His Ser Asn Gly Asn Thr Tyr Leu Glu
  1               5                  10                  15

<210> SEQ ID NO 41
<211> LENGTH: 7
<212> TYPE: PRT
<213> ORGANISM: Artificial Sequence
<220> FEATURE:
<223> OTHER INFORMATION: CDR L2 of antibody 5C9

<400> SEQUENCE: 41

Lys Val Ser Asn Arg Phe Ser
  1               5

<210> SEQ ID NO 42
<211> LENGTH: 9
<212> TYPE: PRT
<213> ORGANISM: Artificial Sequence
<220> FEATURE:
<223> OTHER INFORMATION: CDR L3 of antibody 5C9

<400> SEQUENCE: 42

Phe Gln Gly Ser His Val Pro Phe Thr
  1               5

<210> SEQ ID NO 43
<211> LENGTH: 5
<212> TYPE: PRT
<213> ORGANISM: Artificial Sequence
<220> FEATURE:
<223> OTHER INFORMATION: CDR H1 of antibody 5C9

<400> SEQUENCE: 43

Asn Tyr Leu Ile Glu
  1               5

<210> SEQ ID NO 44
<211> LENGTH: 17
<212> TYPE: PRT
<213> ORGANISM: Artificial Sequence
<220> FEATURE:
<223> OTHER INFORMATION: CDR H2 of antibody 5C9

<400> SEQUENCE: 44

Leu Ile Tyr Pro Gly Ser Gly Gly Thr Asn Tyr Asn Glu Lys Phe Lys
  1               5                  10                  15

Gly

<210> SEQ ID NO 45
<211> LENGTH: 12
<212> TYPE: PRT
<213> ORGANISM: Artificial Sequence
```

<220> FEATURE:
<223> OTHER INFORMATION: CDR H3 of antibody 5C9

<400> SEQUENCE: 45

Ile Tyr Tyr Gly Asn Arg Asp Tyr Gly Met Asp Tyr
1               5                   10

<210> SEQ ID NO 46
<211> LENGTH: 109
<212> TYPE: PRT
<213> ORGANISM: Artificial Sequence
<220> FEATURE:
<223> OTHER INFORMATION: Synthetic construct

<400> SEQUENCE: 46

Met Glu Phe Val Pro Pro Met Val Asn Val Thr Arg Ser Glu Ala Ser
1               5                   10                  15

Glu Gly Asn Ile Thr Val Thr Cys Arg Ala Ser Gly Phe Tyr Pro Trp
            20                  25                  30

Asn Ile Thr Leu Ser Trp Arg Gln Asp Gly Val Ser Leu Ser His Asp
        35                  40                  45

Thr Gln Gln Trp Gly Asp Val Leu Pro Asp Gly Asn Gly Thr Tyr Gln
    50                  55                  60

Thr Trp Val Ala Thr Arg Ile Cys Gln Gly Glu Gln Arg Phe Thr
65                  70                  75                  80

Cys Tyr Met Glu His Ser Gly Asn His Ser Thr His Pro Val Pro Ser
                85                  90                  95

Glu Asn Leu Tyr Phe Gln Gly His His His His His
            100                 105

<210> SEQ ID NO 47
<211> LENGTH: 101
<212> TYPE: PRT
<213> ORGANISM: Artificial Sequence
<220> FEATURE:
<223> OTHER INFORMATION: Synthetic construct

<400> SEQUENCE: 47

Met Glu Phe Arg Ser Glu Ala Ser Glu Gly Asn Ile Thr Val Thr Cys
1               5                   10                  15

Arg Ala Ser Gly Phe Tyr Pro Trp Asn Ile Thr Leu Ser Trp Arg Gln
            20                  25                  30

Asp Gly Val Ser Leu Ser His Asp Thr Gln Gln Trp Gly Asp Val Leu
        35                  40                  45

Pro Asp Gly Asn Gly Thr Tyr Gln Thr Trp Val Ala Thr Arg Ile Cys
    50                  55                  60

Gln Gly Glu Gln Arg Phe Thr Cys Tyr Met Glu His Ser Gly Asn
65                  70                  75                  80

His Ser Thr His Pro Val Pro Ser Glu Asn Leu Tyr Phe Gln Gly His
                85                  90                  95

His His His His His
        100

<210> SEQ ID NO 48
<211> LENGTH: 97
<212> TYPE: PRT
<213> ORGANISM: Artificial Sequence
<220> FEATURE:
<223> OTHER INFORMATION: Synthetic construct

<400> SEQUENCE: 48

Met Glu Phe Arg Ser Glu Ala Ser Glu Gly Asn Ile Thr Val Thr Cys
1               5                   10                  15

Arg Ala Ser Gly Phe Tyr Pro Trp Asn Ile Thr Leu Ser Trp Arg Gln
            20                  25                  30

Asp Gly Val Ser Leu Ser His Asp Thr Gln Gln Trp Gly Asp Val Leu
            35                  40                  45

Pro Asp Gly Asn Gly Thr Tyr Gln Thr Trp Val Ala Thr Arg Ile Cys
50                  55                  60

Gln Gly Glu Glu Gln Arg Phe Thr Cys Tyr Met Glu His Ser Gly Asn
65                  70                  75                  80

His Ser Thr His Glu Asn Leu Tyr Phe Gln Gly His His His His His
            85                  90                  95

His

<210> SEQ ID NO 49
<211> LENGTH: 83
<212> TYPE: PRT
<213> ORGANISM: Artificial Sequence
<220> FEATURE:
<223> OTHER INFORMATION: Synthetic construct

<400> SEQUENCE: 49

Met Glu Phe Arg Ser Glu Ala Ser Glu Gly Asn Ile Thr Val Thr Cys
1               5                   10                  15

Arg Ala Ser Gly Phe Tyr Pro Trp Asn Ile Thr Leu Ser Trp Arg Gln
            20                  25                  30

Asp Gly Val Ser Leu Ser His Asp Thr Gln Gln Trp Gly Asp Val Leu
            35                  40                  45

Pro Asp Gly Asn Gly Thr Tyr Gln Thr Trp Val Ala Thr Arg Ile Cys
50                  55                  60

Gln Gly Glu Glu Gln Arg Glu Asn Leu Tyr Phe Gln Gly His His His
65                  70                  75                  80

His His His

<210> SEQ ID NO 50
<211> LENGTH: 109
<212> TYPE: PRT
<213> ORGANISM: Artificial Sequence
<220> FEATURE:
<223> OTHER INFORMATION: Synthetic construct

<400> SEQUENCE: 50

Met Glu Phe Val Pro Pro Met Val Asn Val Thr Cys Ser Glu Val Ser
1               5                   10                  15

Glu Gly Asn Ile Thr Val Thr Cys Arg Ala Ser Ser Phe Tyr Pro Arg
            20                  25                  30

Asn Ile Thr Leu Thr Trp Arg Gln Asp Gly Val Ser Leu Ser His Asn
            35                  40                  45

Thr Gln Gln Trp Gly Asp Val Leu Pro Asp Gly Asn Gly Thr Tyr Gln
50                  55                  60

Thr Trp Val Ala Thr Arg Ile Arg Gln Gly Glu Glu Gln Arg Phe Thr
65                  70                  75                  80

Cys Tyr Met Glu His Ser Gly Asn His Gly Thr His Pro Val Pro Ser
            85                  90                  95

Glu Asn Leu Tyr Phe Gln Gly His His His His His
                100                 105

<210> SEQ ID NO 51
<211> LENGTH: 101
<212> TYPE: PRT
<213> ORGANISM: Artificial Sequence
<220> FEATURE:
<223> OTHER INFORMATION: Synthetic construct

<400> SEQUENCE: 51

Met Glu Phe Cys Ser Glu Val Ser Glu Gly Asn Ile Thr Val Thr Cys
1               5                   10                  15

Arg Ala Ser Ser Phe Tyr Pro Arg Asn Ile Thr Leu Thr Trp Arg Gln
            20                  25                  30

Asp Gly Val Ser Leu Ser His Asn Thr Gln Gln Trp Gly Asp Val Leu
        35                  40                  45

Pro Asp Gly Asn Gly Thr Tyr Gln Thr Trp Val Ala Thr Arg Ile Arg
    50                  55                  60

Gln Gly Glu Glu Gln Arg Phe Thr Cys Tyr Met Glu His Ser Gly Asn
65                  70                  75                  80

His Gly Thr His Pro Val Pro Ser Glu Asn Leu Tyr Phe Gln Gly His
                85                  90                  95

His His His His His
            100

<210> SEQ ID NO 52
<211> LENGTH: 97
<212> TYPE: PRT
<213> ORGANISM: Artificial Sequence
<220> FEATURE:
<223> OTHER INFORMATION: Synthetic construct

<400> SEQUENCE: 52

Met Glu Phe Cys Ser Glu Val Ser Glu Gly Asn Ile Thr Val Thr Cys
1               5                   10                  15

Arg Ala Ser Ser Phe Tyr Pro Arg Asn Ile Thr Leu Thr Trp Arg Gln
            20                  25                  30

Asp Gly Val Ser Leu Ser His Asn Thr Gln Gln Trp Gly Asp Val Leu
        35                  40                  45

Pro Asp Gly Asn Gly Thr Tyr Gln Thr Trp Val Ala Thr Arg Ile Arg
    50                  55                  60

Gln Gly Glu Glu Gln Arg Phe Thr Cys Tyr Met Glu His Ser Gly Asn
65                  70                  75                  80

His Gly Thr His Glu Asn Leu Tyr Phe Gln Gly His His His His
                85                  90                  95

His

<210> SEQ ID NO 53
<211> LENGTH: 83
<212> TYPE: PRT
<213> ORGANISM: Artificial Sequence
<220> FEATURE:
<223> OTHER INFORMATION: Synthetic construct

<400> SEQUENCE: 53

Met Glu Phe Cys Ser Glu Val Ser Glu Gly Asn Ile Thr Val Thr Cys
1               5                   10                  15

Arg Ala Ser Ser Phe Tyr Pro Arg Asn Ile Thr Leu Thr Trp Arg Gln
            20                  25                  30

Asp Gly Val Ser Leu Ser His Asn Thr Gln Gln Trp Gly Asp Val Leu
        35                  40                  45

-continued

```
Pro Asp Gly Asn Gly Thr Tyr Gln Thr Trp Val Ala Thr Arg Ile Arg
    50                  55                  60

Gln Gly Glu Glu Gln Arg Glu Asn Leu Tyr Phe Gln Gly His His His
65                  70                  75                  80

His His His
```